(12) United States Patent
Rosen et al.

(10) Patent No.: US 7,514,079 B2
(45) Date of Patent: Apr. 7, 2009

(54) ANTIBODIES THAT SPECIFICALLY BIND TO NEUROKININ B

(75) Inventors: Craig A. Rosen, Laytonsville, MD (US); Steven M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 627 days.

(21) Appl. No.: 10/981,692

(22) Filed: Nov. 5, 2004

(65) Prior Publication Data

US 2005/0163777 A1    Jul. 28, 2005

Related U.S. Application Data

(63) Continuation-in-part of application No. PCT/US03/16802, filed on May 29, 2003.

(60) Provisional application No. 60/383,802, filed on May 30, 2002.

(51) Int. Cl.
*A61K 39/395*    (2006.01)
*G01N 33/53*    (2006.01)
*C07K 16/26*    (2006.01)

(52) U.S. Cl. ............ 424/133.1; 424/134.1; 424/135.1; 424/136.1; 424/139.1; 424/141.1; 424/145.1; 424/158.1; 424/181.1; 424/183.1; 424/800; 424/804; 424/806; 424/809; 435/7.1; 435/975; 530/387.1; 530/387.3; 530/387.9; 530/388.23; 530/389.2; 530/391.1; 530/391.7

(58) Field of Classification Search ............... None
See application file for complete search history.

(56) References Cited

FOREIGN PATENT DOCUMENTS

| WO | WO-92/01047 | 1/1992 |
|---|---|---|
| WO | WO-98/40483 A2 | 9/1998 |

OTHER PUBLICATIONS

Verena et al. Arch. Gyn. Obstet., vol. 276, 2007, pp. 151-157, Abstract Only.*
GenBank Accession No. AF216586, Page, et al. (Mar. 2001).
International Preliminary Examination Report for PCT Application No. PCT/US03/16802, mailed Aug. 2, 2007.
International Search Report for PCT Application No. PCT/US03/16802, mailed May 10, 2007.
Yunker, et al, "Neurokinin B- and substance P-like immunoreactivity are co-localized in enteric nerves of rat ileum," *Regulatory Peptides*, 80:67-74 (1999).

* cited by examiner

*Primary Examiner*—Jeffrey Stucker
*Assistant Examiner*—Stephen Gucker

(57) ABSTRACT

The present invention relates to antibodies and related molecules that specifically bind to neurokinin B. Such antibodies have uses, for example, in the prevention and treatment of cancer as well as immune system diseases and disorders including pre-eclampsia, hypertension, inflammation, asthma, gastrointestinal disorders, anxiety, depression, addiction, or pain. The invention also relates to nucleic acid molecules encoding anti-neurokinin B antibodies, vectors and host cells containing these nucleic acids, and methods for producing the same. The present invention relates to methods and compositions for preventing, detecting, diagnosing, treating or ameliorating a disease or disorder, especially pre-eclampsia, as well as hypertension, inflammation, asthma, gastrointestinal disorders, anxiety, depression, addiction, or pain, comprising administering to an animal, preferably a human, an effective amount of one or more antibodies or fragments or variants thereof, or related molecules, that specifically bind to neurokinin B.

27 Claims, No Drawings

ANTIBODIES THAT SPECIFICALLY BIND TO NEUROKININ B

CROSS-REFERENCE TO RELATED APPLICATIONS

This application is a continuation-in-part of International Application No. PCT/US03/16802, filed May 29, 2003, which claims benefit under 35 U.S.C. § 119(e) of U.S. Provisional Application No. 60/383,802, filed May 30, 2002, each of which is hereby incorporated by reference in its entirety.

FIELD OF THE INVENTION

The present invention relates to antibodies and related molecules that specifically bind to neurokinin B. Such antibodies have uses, for example, in the diagnosis, prevention, and treatment of pre-eclampsia, hypertension, inflammation, asthma, gastrointestinal disorders, anxiety, depression, addiction, and/or pain. The invention also relates to nucleic acid molecules encoding anti-neurokinin B antibodies, vectors and host cells containing these nucleic acids, and methods for producing the same. The present invention relates to methods and compositions for preventing, detecting, diagnosing, treating or ameliorating a disease or disorder including pre-eclampsia, hypertension, inflammation, asthma, gastrointestinal disorders, anxiety, depression, addiction, and/or pain, comprising administering to an animal, preferably a human, an effective amount of one or more antibodies or fragments or variants thereof, or related molecules, that specifically bind to neurokinin B.

BACKGROUND OF THE INVENTION

The tachykinins are an evolutionarily conserved family of amidated peptides. The family name tachykinin refers to the ability to induce fast, immediate contractile responses of smooth muscle preparations (as opposed to bradykinin, which elicits a slow contraction). The first family member to be isolated and characterized was substance P (Von Euler and Gaddum, *J. Physiology London* 72:74-86 (1931)), which caused peripheral vasodilation and stimulated intestinal muscle contractions. Other members of the tachykinin family include substance K (or neurokinin A; Nawa et al., *Life Sci.* 34:1153-1160 (1984)) and neuromedin K (or neurokinin B; Kangawa et al., *Biophys. Res. Commun.* 114:533-540 (1983)). Neuropeptide K and neuropeptide γ, which are N-terminally extended forms of neurokinin A, are also included in the family (Tatemoto et al., *Biophys. Res. Commun.* 128:947-953 (1985); Kage et al. *J. Neurochem.* 50:1412-1417 (1988)). All tachykinin peptides share the C-terminal pentapeptide—FXGLMa.

Substance P (SP), neurokinin A (NKA), and neurokinin B (NKB) are derived from two precursor-encoding genes (Nawa et al., *Nature* 312:729-734 (1984); Kotani et al., *Proc. Natl. Acad. Sci. USA* 83:7074-7078 (1986)). Preprotachykinin A (PPTA) codes for SP and NKA, while preprotachykinin B (PPTB) codes for NKB. As a consequence of alternative splicing, three distinct mRNAs are produced from the primary PPTA transcript (α-PPTA, β-PPTA, and γ-PPTA), all of which code for SP (Nawa et al., *Nature* 312:729-734 (1984)). Interestingly, α-PPTA does not include the sixth exon that codes for NKA, β-PPTA contains all exons, and γ-PPTA does not contain the fourth exon. As a result, cells that exclusively express α-PPTA mRNA only produce SP. When β-PPTA is expressed, SP, NKA, or neuropeptide K can be synthesized. γ-PPTA gives rise to SP, NKA, or neuropeptide γ. This alternative RNA and polypeptide precursor processing appears to be an important mechanism in creating structural diversity and tissue-specific differences in the expression of tachykinin neuropeptides. PPTB is cleaved at both the N- and C-terminus to yield the mature form of neurokinin B (amino acids 81 to 90 of SEQ ID NO:2).

The tachykinins exhibit a wide variety of functions. A hallmark feature is their ability to induce contractile responses in smooth muscle. Additional biologic roles include vasodilatation in hypotension, mucous and pancreatic secretion, pain transmission, neurogenic inflammation, and regulation of the immune system (Longmore et al., *Canadian J. Physiol. Pharmacol.* 75:612-621 (1997)). Tachykinins are normally restricted to the central nervous system and exert their effects peripherally by their release from nerve endings. Three membrane receptors that recognize the tachykinins have been identified as NK1R, NK2R, and NK3R. Their preferential endogenous ligands are substance P, neurokinin A, and neurokinin B, respectively. Differences at the amino terminal end of the tachykinins determine their receptor affinities. All three receptors interact with G proteins and have a structure consisting of seven hydrophobic transmembrane regions. Although many protease enzymes are active in degrading tachykinins, the in vivo stability is mainly regulated by angiotensin-converting enzyme (ACE) and neutral endopeptidase 24.11 (NEP; Skidgel et al. *Peptides* 5:769-776 (1984)).

Tachykinins have a large number of in vivo functions, as well as regulated expression patterns. Accordingly, promoting and inhibiting such peptides has wide therapeutic application. There is a clear need, therefore, for identification and characterization of compositions, such as antibodies, that influence the biological activity of tachykinins, both normally and in disease states. In particular, there is a need to isolate and characterize antibodies that modulate the biological activities of neurokinin B for the treatment of pre-eclampsia, hypertension, inflammation, asthma, gastrointestinal disorders, anxiety, depression, addiction, or pain.

SUMMARY OF THE INVENTION

The present invention encompasses antibodies (including molecules comprising, or alternatively consisting of, antibody fragments or variants thereof) that specifically bind to neurokinin B polypeptide (NKB; also known as neurokinin 3 (NK3), tachykinin 3 (TAC3), and neuromedin K; GenBank ID: AF216586; International Publication No. WO 98/40483, which is hereby incorporated by reference in its entirety) or a polypeptide fragment or variant of neurokinin B. In particular, the invention encompasses antibodies (including molecules comprising, or alternatively consisting of, antibody fragments or variants thereof) that specifically bind to a neurokinin B polypeptide (SEQ ID NO:2) or polypeptide fragment or variant of human neurokinin B. In highly preferred embodiments, antibodies of the invention bind a polypeptide consisting of amino acids 81 to 90 of SEQ ID NO:2.

The present invention relates to methods and compositions for preventing, treating or ameliorating a disease or disorder comprising administering to an animal, preferably a human, an effective amount of one or more antibodies or fragments or variants thereof, or related molecules, that specifically bind to neurokinin B or a fragment or variant thereof. In specific embodiments, the present invention relates to methods and compositions for preventing, treating or ameliorating a disease or disorder associated with aberrant neurokinin B function or expression, comprising administering to an animal, preferably a human, an effective amount of one or more antibodies or fragments or variants thereof, or related molecules, that specifically bind to neurokinin B or a fragment or variant thereof.

In highly preferred embodiments, the present invention encompasses methods for using the antibodies of the present invention to treat, prevent, diagnose and/or prognose preeclampsia and a symptom associated with pre-eclampsia including, but not limited to, hypertension, proteinuria, coagulopathy, renal failure, pulmonary edema, and cerebrovascular accident.

In additional preferred embodiments, the present invention encompasses methods for using antibodies of the invention to treat, prevent, diagnose and/or prognose an inflammatory disorder (e.g., inflammatory bowel syndrome, allergy, asthma, chronic cough, inflammatory pain, and chronic obstructive pulmonary disease).

In further preferred embodiments, the present invention relates to methods for using antibodies of the invention to prevent, treat or ameliorate a gastrointestinal disorder (e.g., inflammatory bowel syndrome and irritable bowel syndrome).

In an additional preferred embodiment, the present invention relates to methods for using antibodies of the invention to prevent, treat or ameliorate a neurological disorder (e.g., anxiety, depression, and addiction).

In other highly preferred embodiments, the invention encompasses methods for using the antibodies of the invention to inhibit vasoconstriction. In specific embodiments, the invention encompasses methods for using the antibodies of the present invention to inhibit vasocontriction of the mesenteric vascular bed. In specific embodiments, the invention encompasses methods for using the antibodies of the present invention to inhibit vasoconstriction of the hepatic portal vein.

In other preferred embodiments, the invention encompasses methods for using the antibodies of the invention to stimulate vasoconstriction.

Another embodiment of the present invention includes the use of the antibodies of the invention as a diagnostic tool to monitor the expression of neurokinin B.

The present invention encompasses single chain Fv's (scFvs) that specifically bind neurokinin B polypeptides (e.g., SEQ ID NOs:22-40). Thus, in certain embodiments, the invention encompasses these scFvs, listed in Table 1.

Further, the present invention encompasses the polynucleotides encoding the scFvs, as well as the amino acid sequences of the scFvs. Molecules comprising, or alternatively consisting of, fragments or variants of these scFvs (e.g., VH domains, VH CDRs, VL domains, or VL CDRs having an amino acid sequence of any one of the scFvs referred to in Table 1), that specifically bind to neurokinin B or fragments or variants thereof are also encompassed by the invention, as are nucleic acid molecules that encode these antibodies and/or molecules.

The present invention also provides anti-neurokinin B antibodies that are coupled to a detectable label, such as an enzyme, a fluorescent label, a luminescent label, or a bioluminescent label. The present invention also provides anti-neurokinin B antibodies that are coupled to a therapeutic or cytotoxic agent. The present invention also provides anti-neurokinin B antibodies which are coupled to a radioactive material.

The present invention also provides antibodies that bind neurokinin B polypeptides and that act as either neurokinin B agonists or neurokinin B antagonists. In preferred embodiments, the antibodies of the invention act as neurokinin B antagonists. In specific embodiments, the antibodies of the invention inhibit neurokinin B binding to the neurokinin 3 receptor (NK3R; GenBank ID: JQ1517). In other specific embodiments, the antibodies of the invention inhibit neurokinin B binding to the neurokinin 2 receptor (NK2R; GenBank ID: M57414) and/or the neurokinin 1 receptor (NK1R; GenBank ID: M81797).

In further embodiments, the antibodies of the invention have a dissociation constant ($K_D$) of $10^{-7}$ M or less. In preferred embodiments, the antibodies of the invention have a dissociation constant ($K_D$) of $10^{-9}$ M or less.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs). The present invention further provides mixtures of antibodies, wherein the mixture corresponds to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The present invention also provides for fusion proteins comprising an antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule(s), generally isolated, encoding an antibody (including molecules, such as scfvs, VH domains, or VL domains, that comprise, or alternatively consist of, an antibody fragment or variant thereof) of the invention. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

DETAILED DESCRIPTION OF THE INVENTION

Definitions

The term "antibody," as used herein, refers to immunoglobulin molecules and immunologically active portions of immunoglobulin molecules, i.e., molecules that contain an antigen binding site that specifically binds an antigen. As such, the term antibody encompasses not only whole antibody molecules, but also antibody multimers, antibody fragments as well as variants (including derivatives) of antibodies, antibody multimers and antibody fragments. Examples of molecules which are described by the term "antibody" herein include, but are not limited to: single chain Fvs (scFvs), Fab fragments, Fab' fragments, F(ab')$_2$, disulfide linked Fvs (sd-Fvs), Fvs, and fragments comprising or alternatively consisting of, either a VL or a VH domain. The term "single chain Fv" or "scFv" as used herein refers to a polypeptide comprising a VH domain of antibody linked to a VL domain of an antibody. Antibodies that specifically bind to neurokinin B may have cross-reactivity with other antigens. Preferably, antibodies that specifically bind to neurokinin B do not cross-react with other antigens (e.g., other members of the tachykinin family). Antibodies that specifically bind to neurokinin B can be identified, for example, by immunoassays or other techniques known to those of skill in the art.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass of immunoglobulin molecule. Preferably, an antibody of the invention comprises, or alternatively consists of, a VH domain, VH CDR, VL domain, or VL CDR having an amino acid sequence of any one of those referred to in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers within an antibody multimer may be identical or different, i.e., antibody mulitmers may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31. and Frigerio et al., (2000) Plant Physiology 123:1483-94., both of which are hereby incorporated by reference in their entireties.) ScFv dimers can also be formed through recombinant techniques known in the art; an example of the construction of scFv dimers is given in Goel et al., (2000) Cancer Research 60:6964-6971 which is hereby incorporated by reference in its entirety. Antibody multimers may be purified using any suitable method known in the art, including, but not limited to, size exclusion chromatography.

By "isolated antibody" is intended an antibody removed from its native environment. Thus, an antibody produced by, purified from and/or contained within a hybridoma and/or a recombinant host cell is considered isolated for purposes of the present invention.

Unless otherwise defined in the specification, specific binding or immunospecifc binding by an anti-neurokinin B antibody means that the anti-neurokinin B antibody binds neurokinin B but does not significantly bind to (i.e., cross-react with) proteins other than neurokinin B, such as other proteins in the same family of proteins). An antibody that binds neurokinin B protein and does not cross-react with other proteins is not necessarily an antibody that does not bind said other proteins in all conditions; rather, the neurokinin B-specific antibody of the invention preferentially binds neurokinin B compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that neurokinin B-specific antibodies bind to epitopes of neurokinin B, an antibody that specifically binds neurokinin B may or may not bind fragments of neurokinin B and/or variants of neurokinin B (e.g., proteins that are at least 90% identical to neurokinin B) depending on the presence or absence of the epitope bound by a given neurokinin B-specific antibody in the neurokinin B fragment or variant. Likewise, neurokinin B-specific antibodies of the invention may bind species orthologues of neurokinin B (including fragments thereof) depending on the presence or absence of the epitope recognized by the antibody in the orthologue. Additionally, neurokinin B-specific antibodies of the invention may bind modified forms of neurokinin B, for example, neurokinin B fusion proteins. In such a case when antibodies of the invention bind neurokinin B fusion proteins, the antibody must make binding contact with the neurokinin B moiety of the fusion protein in order for the binding to be specific. Antibodies that specifically bind to neurokinin B can be identified, for example, by immunoassays or other techniques known to those of skill in the art, e.g., the immunoassays described in the Examples below.

The term "variant" as used herein refers to a polypeptide that possesses a similar or identical amino acid sequence as a neurokinin B polypeptide, a fragment of a neurokinin B polypeptide, an anti-neurokinin B antibody or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a neurokinin B polypeptide, a fragment thereof, an anti-neurokinin B antibody or antibody fragment thereof (including a VH domain, VHCDR, VL domain, or VLCDR having an amino acid sequence of any one or more scFvs referred to in Table 1) described herein; (b) a polypeptide encoded by a nucleotide sequence, the complementary sequence of which hybridizes under stringent conditions to a nucleotide sequence encoding a neurokinin B polypeptide (e.g., SEQ ID NO:2), a fragment of a neurokinin B polypeptide (e.g., the mature form of neurokinin B (amino acids 81 to 90 of SEQ ID NO:2)), an anti-neurokinin B antibody or antibody fragment thereof (including a VH domain, VHCDR, VL domain, or VLCDR having an amino acid sequence of any one of those referred to in Table 1), described herein, of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%,. at least 80%, at least 85%, at least 90%, at least 95% or at least 99%, identical to the nucleotide sequence encoding a neurokinin B polypeptide, a fragment of a neurokinin B polypeptide, an anti-neurokinin B antibody or antibody fragment thereof (including a VH domain, VHCDR, VL domain, or VLCDR having an amino acid sequence of any one or more scFvs referred to in Table 1), described herein. A polypeptide with similar structure to a neurokinin B polypeptide, a fragment of a neurokinin B polypeptide, an anti-neurokinin B antibody or antibody fragment thereof, described herein refers to a polypeptide that has a similar secondary, tertiary or quaternary structure of a neurokinin B polypeptide, a fragment of a neurokinin B polypeptide, an anti-neurokinin B antibody, or antibody fragment thereof, described herein. The structure of a polypeptide can determined by methods known to those skilled in the art, including but not limited to, X-ray crystallography, nuclear magnetic resonance, and crystallographic electron microscopy. Preferably, a variant neurokinin B polypeptide, a variant fragment of a neurokinin B polypeptide, or a variant anti-neurokinin B antibody and/or antibody fragment possesses similar or identical function and/or structure as the reference neurokinin B polypeptide, the reference fragment of a neurokinin B polypeptide, or the reference anti-neurokinin B antibody and/or antibody fragment, respectively.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl. Acad. Sci. USA* 87:2264-2268 (1990), modified as in Karlin and Altschul *Proc. Natl. Acad. Sci. USA* 90:5873-5877 (1993). The BLASTn and BLASTx programs of Altschul, et al. *J. Mol. Biol.* 215:403-410 (1990) have incorporated such an alogrithm. BLAST nucleotide searches can be performed with the BLASTn program (score=100, wordlength=12) to obtain nucleotide sequences homologous to a nucleic acid molecules of the invention. BLAST protein searches can be performed with the BLASTx program (score=50, wordlength=3) to obtain amino acid sequences homologous to a protein molecules of the invention. To obtain gapped alignments for comparison purposes, Gapped BLAST can be utilized as described in Altschul et al. *Nucleic Acids Res.* 25:3589-3402 (1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used.

Another example of a mathematical algorithm utilized for the comparison of sequences is the algorithm of Myers and Miller, CABIOS (1989). The ALIGN program (version 2.0) which is part of the GCG sequence alignment software package has incorporated such an alogrithm. Other algorithms for sequence analysis known in the art include ADVANCE and ADAM as described in Torellis and Robotti *Comput. Appl. Biosci.,* 10:3-5(1994); and FASTA described in Pearson and Lipman *Proc. Natl. Acad. Sci.* 85:2444-8(1988). Within FASTA, ktup is a control option that sets the sensitivity and speed of the search.

The term "derivative" as used herein, refers to a variant polypeptide of the invention that comprises, or alternatively consists of, an amino acid sequence of a neurokinin B polypeptide, a fragment of a neurokinin B polypeptide, or an antibody of the invention that specifically binds to a neurokinin B polypeptide, which has been altered by the introduction of amino acid residue substitutions, deletions or additions. The term "derivative" as used herein also refers to a neurokinin B polypeptide, a fragment of a neurokinin B polypeptide, an antibody that specifically binds to a neurokinin B polypeptide which has been modified, e.g., by the covalent attachment of any type of molecule to the polypeptide. For example, but not by way of limitation, a neurokinin B polypeptide, a fragment of a neurokinin B polypeptide, or an anti-neurokinin B antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a neurokinin B polypeptide, a fragment of a neurokinin B polypeptide, or an anti-neurokinin B antibody, may be modified by chemical modifications using techniques known to those of skill in the art, including, but not limited to, specific chemical cleavage, acetylation, formylation, metabolic synthesis of tunicamycin, etc. Further, a derivative of a neurokinin B polypeptide, a fragment of a neurokinin B polypeptide, or an anti-neurokinin B antibody, may contain one or more non-classical amino acids. A polypeptide derivative possesses a similar or identical function as a neurokinin B polypeptide, a fragment of a neurokinin B polypeptide, or an anti-neurokinin B antibody, described herein.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino residues, at least 70 amino acid residues, at least 80 amino acid residues, at least 90 amino acid residues, at least 1000 amino acid residues, at least 110 amino acid residues, or at least 120 amino acid residues of the amino acid sequence of neurokinin B, or an anti-neurokinin B antibody (including molecules such as scFv's, that comprise, or alternatively consist of, antibody fragments or variants thereof) that specifically binds to neurokinin B.

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, 1gG, IgA, and IgE, respectively. See generally, *Fundamental Immunology* Ch. 7 (Paul, W., ed., 2nd ed. Raven Press, N.Y. (1989), incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hypervariable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk J *Mol. Biol.* 196: 901-917 (1987); Chothia et al. *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. J *Immunol.* 148:1547 1553 (1992). In addition, bispecific antibodies may be formed as "diabodies" (Holliger et al. "'Diabodies': small bivalent and bispecific antibody fragments" *PNAS USA* 90:6444-6448 (1993)) or "Janusins" (Traunecker et al. "Bispecific single chain molecules (Janusins) target cytotoxic lymphocytes on HIV infected cells" *EMBO J* 10:3655-3659 (1991) and Traunecker et al. "Janusin: new molecular design for bispecific reagents" *Int. J. Cancer Suppl.* 7:51-52 (1992)).

Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Anti-Neurokinin B Antibodies

Using phage display technology, single chain antibody molecules ("scFvs") have been identified that specifically bind to neurokinin B (or fragments or variants thereof). Molecules comprising, or alternatively consisting of, fragments or variants of these scFvs (e.g., including VH domains, VH CDRs, VL domains, or VL CDRs having an amino acid sequence of any one of those referred to in Table 1), that specifically bind to neurokinin B (or fragments or variants thereof) are also encompassed by the invention, as are nucleic acid molecules that encode these scFvs, and/or molecules.

In particular, the invention relates to scFvs comprising, or alternatively consisting of the amino acid of SEQ ID NOs: 22-40, referred to in Table 1 below. Molecules comprising, or alternatively consisting of, fragments or variants (e.g., including VH domains, VH CDRs, VL domains, or VL CDRs identified in Table 1) of the scFvs referred to in Table 1, that specifically bind to neurokinin B are also encompassed by the invention, as are nucleic acid molecules that encode these scFvs, and/or molecules (e.g., SEQ ID NOs:3-21).

ScFvs corresponding to SEQ ID NOs: 22-40 were selected for their ability to bind the mature form of the neurokinin B polypeptide (amino acids 81 to 90 of SEQ ID NO:2).

The present invention provides antibodies (including molecules comprising, or alternatively consisting of, antibody fragments or variants thereof) that specifically bind to a polypeptide or a polypeptide fragment of neurokinin B.

In particular, the invention provides antibodies corresponding to the scFvs referred to in Table 1, such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule, as described in more detail in Example 2 below.

Accordingly, in one embodiment, the invention provides antibodies that comprise the VH and VL domains of scFvs of the invention.

In a preferred embodiment, an antibody of the invention is an antibody expressed by any one of the cell lines disclosed in Table 1.

about 90 in SEQ ID NO:2); as well as polypeptides which are at least 80% identical, more preferably at least 90% or 95% identical, still more preferably at least 96%, 97%, 98% or 99% identical to the polypeptides described above (e.g., the polypeptide encoded by the deposited cDNA clones (the deposit having ATCC Accession Number 97922 and/or

TABLE 1 scFvs that Specifically Bind to Neurokinin B

| scFv | scFv DNA SEQ ID NO: | scFv Protein SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 |
|---|---|---|---|---|---|---|---|---|---|---|
| N024C01 | 3 | 22 | 1-124 | 31-40 | 55-71 | 104-113 | 140-250 | 162-174 | 190-196 | 229-239 |
| NO25B07 | 4 | 23 | 1-125 | 31-36 | 50-63 | 96-115 | 141-251 | 163-175 | 191-197 | 229-240 |
| N015E08 | 5 | 24 | 1-116 | 31-35 | 50-66 | 99-105 | 132-242 | 154-166 | 182-188 | 221-231 |
| NO15F10 | 6 | 25 | 1-121 | 31-35 | 50-66 | 99-110 | 138-248 | 160-172 | 188-194 | 227-237 |
| NO24D01 | 7 | 26 | 1-118 | 31-35 | 50-66 | 99-107 | 134-244 | 155-168 | 184-190 | 223-233 |
| NO15D08 | 8 | 27 | 1-121 | 31-35 | 50-66 | 99-110 | 137-247 | 159-171 | 187-193 | 226-236 |
| NO24B07 | 9 | 28 | 1-121 | 31-35 | 50-66 | 99-110 | 138-248 | 160-172 | 188-194 | 227-237 |
| NO24E07 | 10 | 29 | 1-117 | 31-35 | 50-66 | 99-106 | 133-243 | 155-167 | 183-189 | 222-232 |
| NO23F05 | 11 | 30 | 1-128 | 31-35 | 50-66 | 99-117 | 145-255 | 167-179 | 195-201 | 234-244 |
| NO24D08 | 12 | 31 | 1-119 | 31-35 | 50-66 | 99-108 | 135-245 | 157-169 | 185-191 | 224-234 |
| NO23B03 | 13 | 32 | 1-122 | 31-35 | 50-66 | 99-111 | 139-248 | 161-174 | 190-196 | 229-237 |
| NO23E01 | 14 | 33 | 1-117 | 31-35 | 50-66 | 99-106 | 133-243 | 155-167 | 183-189 | 222-232 |
| NO24C05 | 15 | 34 | 1-125 | 31-37 | 52-70 | 103-114 | 141-251 | 163-176 | 192-198 | 231-240 |
| NO25E05 | 16 | 35 | 1-119 | 31-35 | 50-66 | 99-108 | 136-245 | 158-170 | 186-192 | 225-234 |
| NO25C01 | 17 | 36 | 1-119 | 31-35 | 50-66 | 99-108 | 135-245 | 157-169 | 185-191 | 224-234 |
| NO24F09 | 18 | 37 | 1-121 | 31-35 | 50-66 | 99-110 | 137-247 | 159-171 | 187-193 | 226-236 |
| NO24B01 | 19 | 38 | 1-118 | 31-35 | 50-66 | 99-107 | 135-246 | 158-170 | 186-192 | 225-235 |
| NO24F07 | 20 | 39 | 1-122 | 31-35 | 50-66 | 99-111 | 138-248 | 160-172 | 188-194 | 227-237 |
| NO15D10 | 21 | 40 | 1-116 | 31-35 | 50-66 | 99-105 | 132-242 | 154-166 | 182-188 | 221-231 |

The present invention encompasses antibodies (including molecules comprising, or alternatively consisting of, antibody fragments or variants thereof) that specifically bind to a neurokinin B polypeptide or a fragment, variant, or fusion protein thereof A neurokinin B polypeptide includes, but is not limited to, neurokinin B (SEQ ID NO:2) or the polypeptide encoded by the cDNA contained in ATCC Deposit No. 97922 on Mar. 7, 1997 and/or ATCC Deposit No. 97375 on Dec. 8, 1995. Neurokinin B may be produced through recombinant expression of nucleic acids encoding the polypeptides of SEQ ID NO:2 (e.g., the cDNA in ATCC Deposit Number 97922 and/or ATCC Deposit No. 97375). Antibodies of the invention may specifically bind neurokinin B as well as fragments and variants thereof, and are described in more detail below.

Neurokinin B Polypeptides

In certain embodiments of the present invention, the antibodies of the present invention bind a neurokinin B polypeptide, or fragments or variants thereof. The following section describes the neurokinin B polypeptides, fragments and variants that may be bound by the antibodies of the invention in more detail.

The antibodies of the present invention also include antibodies that bind a polypeptide comprising, or alternatively, consisting of the polypeptide encoded by the deposited cDNAs (the deposit having ATCC Accession Number 97922 and/or ATCC Deposit No. 97375); a polypeptide comprising, or alternatively, consisting of the polypeptide of SEQ ID NO:2; a polypeptide comprising, or alternatively, consisting of the precursor polypeptide of SEQ ID NO:2 (predicted to constitute amino acid residues from about 17 to about 121 in SEQ ID NO:2); a polypeptide comprising, or alternatively, consisting of the mature polypeptide of SEQ ID NO:2 (predicted to constitute amino acid residues from about 81 to about 90 in SEQ ID NO:2); as well as polypeptides which are at least 80% identical, more preferably at least 90% or 95% identical, still more preferably at least 96%, 97%, 98% or 99% identical to the polypeptides described above (e.g., the polypeptide encoded by the deposited cDNA clones (the deposit having ATCC Accession Number 97922 and/or ATCC Deposit No. 97375), the polypeptide of SEQ ID NO:2, and portions of such polypeptides.

By a polypeptide having an amino acid sequence at least, for example, 95% "identical" to a reference amino acid sequence of a neurokinin B polypeptide is intended that the amino acid sequence of the polypeptide is identical to the reference sequence except that the polypeptide sequence may include up to one amino acid alterations per each 20 amino acids of the reference amino acid of the neurokinin B polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

In certain embodiments, the antibodies of the present invention specifically bind neurokinin B polypeptide. An antibody that specifically binds neurokinin B may, in some embodiments, bind fragments, variants (including species orthologs and allelic variants of neurokinin B), multimers, processed forms, subprocessed forms, or modified forms of neurokinin B. For example, an antibody specific for neurokinin B may bind the neurokinin B moiety of a fusion protein comprising all or a portion of neurokinin B.

Neurokinin B proteins may be found as monomers or multimers (i.e., dimers, trimers, tetramers, and higher multimers). Accordingly, the present invention relates to antibodies that bind neurokinin B proteins found as monomers or as part of multimers. In specific embodiments, antibodies of the invention bind neurokinin B monomers, dimers, trimers or tetramers. In additional embodiments, antibodies of the invention bind at least dimers, at least trimers, or at least tetramers containing one or more neurokinin B polypeptides.

Antibodies of the invention may bind neurokinin B homomers or heteromers. As used herein, the term homomer, refers to a multimer containing only neurokinin B proteins of the invention (including neurokinin B fragments, variants, and fusion proteins, as described herein). These homomers may contain neurokinin B proteins having identical or different polypeptide sequences. In a specific embodiment, a homomer of the invention is a multimer containing only neurokinin B proteins having an identical polypeptide sequence. In another specific embodiment, antibodies of the invention bind neurokinin B homomers containing neurokinin B proteins having different polypeptide sequences. In specific embodiments, antibodies of the invention bind a neurokinin B homodimer (e.g., containing neurokinin B proteins having identical or different polypeptide sequences) or a homotrimer (e.g., containing neurokinin B proteins having identical or different polypeptide sequences). In additional embodiments, antibodies of the invention bind at least a homodimer, at least a homotrimer, or at least a homotetramer of neurokinin B.

As used herein, the term heteromer refers to a multimer containing heterologous proteins (i.e., proteins containing polypeptide sequences that do not correspond to a polypeptide sequences encoded by a gene encoding neurokinin B) in addition to the neurokinin B proteins of the invention. In a specific embodiment, antibodies of the invention bind a heterodimer, a heterotrimer, or a heterotetramer. In additional embodiments, the antibodies of the invention bind at least a heterodimer, at least a heterotrimer, or at least a heterotetramer containing one or more neurokinin B polypeptides.

Antibodies of the invention bind neurokinin B multimers that are the result of hydrophobic, hydrophilic, ionic and/or covalent associations and/or may be indirectly linked, by for example, liposome formation. Thus, in one embodiment, antibodies of the invention may bind neurokinin B multimers, such as, for example, homodimers or homotrimers, that are formed when neurokinin B proteins contact one another in solution. In another embodiment, antibodies of the invention may bind neurokinin B heteromultimers, such as, for example, heterotrimers or heterotetramers, that are formed when proteins of the invention contact antibodies to the neurokinin B polypeptides (including antibodies to the heterologous polypeptide sequence in a fusion protein) in solution. In other embodiments, multimers that antibodies of the invention may bind are formed by covalent associations with and/or between the neurokinin B proteins of the invention. Such covalent associations may involve one or more amino acid residues contained in the polypeptide sequence of the protein (e.g., the polypeptide sequence recited in SEQ ID NO:2 or the polypeptide encoded by the deposited cDNA clone of ATCC Deposit 97922 and/or ATCC Deposit No. 97375). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a neurokinin B fusion protein. In one example, covalent associations are between the heterologous sequence contained in a fusion protein (see, e.g., U.S. Pat. No. 5,478,925). In a specific example, the covalent associations are between the heterologous sequence contained in a neurokinin B-Fc fusion protein (as described herein). In another specific example, covalent associations of fusion proteins are between heterologous polypeptide sequences from another tachykinin family ligand/receptor member, such as for example, substance P or neurokinin A.

Antibodies of the invention may bind neurokinin B multimers that were generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers that may be bound by one or more antibodies of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins that may be bound by one or more antibodies of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that antibodies of the invention may bind (see, e.g., U.S. Pat. No. 5,478,925, which is herein incorporated by reference in its entirety).

Alternatively, antibodies of the invention may bind neurokinin B multimers that were generated using genetic engineering techniques known in the art. In one embodiment, proteins contained in multimers that may be bound by one or more antibodies of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that may be bound by one or more antibodies of the invention are generated by ligating a polynucleotide sequence encoding a neurokinin B polypeptide to a sequence encoding a linker polypeptide and then further to a synthetic polynucleotide encoding the translated product of the polypeptide in the reverse orientation from the original C-terminus to the N-terminus (see, e.g., U.S. Pat. No. 5,478,925, which is herein incorporated by reference in its entirety). In another embodiment, recombinant techniques described herein or otherwise known in the art are applied to generate recombinant neurokinin B polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more neurokinin B polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple neurokinin B polypeptides separated by peptide linkers may be produced using conventional recombinant DNA technology. In specific embodiments, antibodies of the invention bind proteins comprising multiple neurokinin B polypeptides separated by peptide linkers.

Another method for preparing multimer neurokinin B polypeptides involves use of neurokinin B polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric neurokinin B proteins are those described in PCT application WO 94/10308, hereby incorporated by reference. Recombinant fusion proteins comprising a soluble neurokinin B polypeptide fused to a peptide that dimerizes or trimerizes in solution are expressed in suitable host cells, and the resulting soluble multimeric neurokinin B is recovered from the culture supernatant using techniques known in the art. In specific embodiments, antibodies of the invention bind neurokinin B-leucine zipper fusion protein monomers and/or neurokinin B-leucine zipper fusion protein multimers.

Antibodies that bind neurokinin B may bind them as isolated polypeptides or in their naturally occurring state. For, example antibodies of the present invention may bind recombinantly produced neurokinin B.

Antibodies that bind neurokinin B may bind selectively to any of the processed forms of neurokinin B (e.g., neurokinin B minus the signal sequence and the mature form of neurokinin B) and/or may alter processing of the precursor protein (PPTB) to a downstream form.

Antibodies of the present invention may also bind neurokinin B purified from a cell culture, wherein the cells (e.g., CHO and NSO) produce neurokinin B that is proteolytically and/or preproteolytically processed.

In a specific embodiment, antibodies of the present invention bind neurokinin B purified from a cell culture, wherein the neurokinin B polypeptide is encoded by a polynucleotide encoding amino acids 1 to 121 of SEQ ID NO:2 operably associated with a regulatory sequence that controls expression of said polynucleotide.

In a specific embodiment, antibodies of the present invention bind neurokinin B peptide purified from a cell culture, wherein the neurokinin B peptide is encoded by a polynucleotide encoding amino acids 81 to 90 of SEQ ID NO:2 operably associated with a regulatory sequence that controls expression of said polynucleotide.

In certain embodiments, antibodies of the present invention may also bind neurokinin B produced by chemical or semi-synthetic methodologies known in the art (see, Kelley et al. in *Genetic Engineering Principles and Methods*, Setlow, J. K., ed., Plenum Press, NY., vol. 12, pp. 1-19 (1990); Stewart et al., *Solid-Phase Peptide Synthesis*, W. H. Freeman Co., San Francisco (1989)). One advantage of these methodologies is that they allow for the incorporation of non-natural amino acid residues into the sequence of neurokinin B.

Antibodies of the present invention may bind neurokinin B polypeptide fragments comprising or alternatively, consisting of, an amino acid sequence contained in SEQ ID NO:2, encoded by the cDNA contained in ATCC deposit Number 97922 and/or ATCC Deposit No. 97375, or encoded by nucleic acids which hybridize (e.g., under stringent hybridization conditions) to the nucleotide sequence contained in ATCC deposit Number 97922 and/or ATCC Deposit No. 97375, or the complementary strand thereto. Protein fragments may be "free-standing," or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 16, 17 to 37, 38 to 58, 59 to 80, 81 to 90, 91 to 111 and/or 112 to 121 of SEQ ID NO:2. In this context "about" includes the particularly recited value, larger or smaller by several (5, 4, 3, 2, or 1) amino acids, at either extreme or at both extremes. Moreover, polypeptide fragments that antibodies of the invention may bind can be at least about 5, 10, 20, 30, 40, 50, 60, 70, 80, 90, 100, or 110 amino acids in length. In this context "about" includes the particularly recited value, larger or smaller by several (5, 4, 3, 2, or 1) amino acids, at either extreme or at both extremes.

Preferably, antibodies of the present invention bind a polypeptide comprising, or alternatively consisting of, a fragment of the predicted mature neurokinin B polypeptide (predicted to constitute amino acid residues from about 81 to about 90 in SEQ ID NO:2), wherein the fragment has a neurokinin B functional activity (e.g., antigenic activity or biological activity). Polynucleotides encoding these polypeptides are also encompassed by the invention.

In an additional embodiment, antibodies of the present invention may bind a polypeptide comprising, or alternatively consisting of, a fragment of the predicted neurokinin B precursor polypeptide (predicted to constitute amino acid residues from about 17 to about 121 in SEQ ID NO:2). Polynucleotides encoding these polypeptides are also encompassed by the invention. In a specific embodiment, binding of an antibody to the neurokinin B precursor polypeptide inhibits processing of the polypeptide to its mature form.

In highly preferred embodiments, the antibodies of the invention that bind neurokinin B prevent a neurokinin B receptor (e.g., NK3R) from binding to neurokinin B. In other highly preferred embodiments, the antibodies of the invention that bind neurokinin B antagonize or neutralize neurokinin B. In other highly preferred embodiments, the antibodies of the invention that bind neurokinin B inhibit vasoconstriction (e.g., of the hepatic portal vein, mesenteric vascular bed). In other embodiments, the antibodies of the invention that bind neurokinin B stimulate vasoconstriction (e.g., of the hepatic portal vein, mesenteric vascular bed).

In another aspect, the invention provides an antibody that binds a peptide or polypeptide comprising an epitope-bearing portion of a polypeptide described herein. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998- 4002 (1983).

As one of skill in the art will appreciate, neurokinin B polypeptides and the epitope-bearing fragments thereof described herein can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric neurokinin B protein or protein fragment alone (Fountoulakis et al., *J Biochem* 270:3958-3964 (1995)). Thus, antibodies of the invention may bind fusion proteins that comprise all or a portion of a neurokinin B polypeptide.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified neurokinin B polypeptides or neurokinin B polypeptide fragments or variants.

For instance, for many proteins, including the extracellular domain of a membrane associated protein or the mature form(s) of a secreted protein, it is known in the art that one or more amino acids may be deleted from the N-terminus or C-terminus without substantial loss of biological function, or loss of the ability to be bound by a specific antibody. For instance, Ron et al., *J. Biol. Chem.*, 268:2984-2988 (1993) reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other functional activities (e.g., biological activities, ability to bind a neurokinin B receptor (e.g., NK3R)) may still be retained. For example, the ability of shortened neurokinin B polypeptides to induce and/or bind to antibodies which recognize the complete or mature forms of the neurokinin B polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a neurokinin B polypeptide with deleted N-terminal amino acid residues may retain some biological or immunogenic activities. In fact, peptides composed of as few as six neurokinin B amino acid residues may often evoke an immune response.

Accordingly, the present invention further provides antibodies that bind polypeptides having one or more residues deleted from the amino terminus of the neurokinin B amino acid sequence of SEQ ID NO:2 up to the phenylalanine residue at position number 85 and polynucleotides encoding such polypeptides. In particular, the present invention provides antibodies that bind polypeptides comprising, or alternatively consisting of, the amino acid sequence of residues $n^1$-90 of SEQ ID NO:2, where $n^1$ is an integer from 1 to 85 corresponding to the position of the amino acid residue in SEQ ID NO:2.

More in particular, the invention provides antibodies that bind polypeptides comprising, or alternatively consisting of, the amino acid sequence of residues of M-1 to M-90; R-2 to M-90; I-3 to M-90; M-4 to M-90; L-5 to M-90; L-6 to M-90; F-7 to M-90; T-8 to M-90; A-9 to M-90; I-10 to M-90; L-11 to M-90; A-12 to M-90; F-13 to M-90; S-14 to M-90; L-15 to M-90; A-16 to M-90; Q-17 to M-90; S-18 to M-90; F-19 to M-90; G-20 to M-90; A-21 to M-90; V-22 to M-90; C-23 to M-90; K-24 to M-90; E-25 to M-90; P-26 to M-90; Q-27 to M-90; E-28 to M-90; E-29 to M-90; V-30 to M-90; V-31 to M-90; P-32 to M-90; G-33 to M-90; G-34 to M-90; G-35 to M-90; R-36 to M-90; S-37 to M-90; K-38 to M-90; R-39 to M-90; D-40 to M-90; P-41 to M-90; D-42 to M-90; L-43 to M-90; Y-44 to M-90; Q-45 to M-90; L-46 to M-90; L-47 to M-90; Q-48 to M-90; R-49 to M-90; L-50 to M-90; F-51 to M-90; K-52 to M-90; S-53 to M-90; H-54 to M-90; S-55 to M-90; S-56 to M-90; L-57 to M-90; E-58 to M-90; G-59 to M-90; L-60 to M-90; L-61 to M-90; K-62 to M-90; A-63 to M-90; L-64 to M-90; S-65 to M-90; Q-66 to M-90; A-67 to M-90; S-68 to M-90; T-69 to M-90; D-70 to M-90; P-71 to M-90; K-72 to M-90; E-73 to M-90; S-74 to M-90; T-75 to M-90; S-76 to M-90; P-77 to M-90; E-78 to M-90; K-79 to M-90; R-80 to M-90; D-81 to M-90; M-82 to M-90; H-83 to M-90; D-84 to M-90; F-85 to M-90 of the neurokinin B sequence of SEQ ID NO:2.

As mentioned above, even if deletion of one or more amino acids from the C-terminus of a protein results in modification or loss of one or more biological functions of the protein, other functional activities (e.g., biological activities, ability to bind a neurokinin B receptor (e.g., NK3R)) may still be retained. For example the ability of the shortened neurokinin B polypeptide to induce and/or bind to antibodies which recognize the complete or mature forms of the neurokinin B polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a neurokinin B polypeptide with a large number of deleted C-terminal amino acid residues may retain some biological or immunogenic activities. In fact, peptides composed of as few as six neurokinin B amino acid residues may often evoke an immune response.

In another embodiment, antibodies of the invention bind C-terminal deletions of the mature neurokinin B polypeptide that can be described by the general formula 81-$m^1$ where $m^1$ is a number from 86 to 89 corresponding to the amino acid sequence identified of SEQ ID NO:2. In specific embodiments, the invention provides antibodies that bind neurokinin B polypeptides comprising, or alternatively consisting of, the amino acid sequence of residues: D-81 to L-89; D-81 to G-88; D-81 to V-87; D-81 to F-86 of the neurokinin B sequence of SEQ ID NO:2.

In another embodiment, antibodies of the invention bind C-terminal deletions of the neurokinin B polypeptide that can be described by the general formula 1-$m^2$ where $m^2$ is a number from 6 to 120 corresponding to the amino acid sequence identified of SEQ ID NO:2. In specific embodiments, the invention provides antibodies that bind neurokinin B polypeptides comprising, or alternatively consisting of, the amino acid sequence of residues: M-1 to A-120; M-1 to R-119; M-1 to P-118; M-1 to P-117; M-1 to Y-116; M-1 to K-115; M-1 to L-114; M-1 to I-113; M-1 to G-112; M-1 to F-111; M-1 to S-110; M-1 to P-109; M-1 to V-108; M-1 to N-107; M-1 to E-106; M-1 to Q-105; M-1 to N-104; M-1 to V-103; M-1 to D-102; M-1 to T-101; M-1 to P-100; M-1 to S-99; M-1 to D-98; M-1 to P-97; M-1 to Q-96; M-1 to V-95; M-1 to S-94; M-1 to R-93; M-1 to K-92; M-1 to G-91; M-1 to M-90; M-1 to L-89; M-1 to G-88; M-1 to V-87; M-1 to F-86; M-1 to F-85; M-1 to D-84; M-1 to H-83; M-1 to M-82; M-1 to D-81; M-1 to R-80; M-1 to K-79; M-1 to E-78; M-1 to P-77; M-1 to S-76; M-1 to T-75; M-1 to S-74; M-1 to E-73; M-1 to K-72; M-1 to P-71; M-1 to D-70; M-1 to T-69; M-1 to S-68; M-1 to A-67; M-1 to Q-66; M-1 to S-65; M-1 to L-64; M-1 to A-63; M-1 to K-62; M-1 to L-61; M-1 to L-60; M-1 to G-59; M-1 to E-58; M-1 to L-57; M-1 to S-56; M-1 to S-55; M-1 to H-54; M-1 to S-53; M-1 to K-52; M-1 to F-51; M-1 to L-50; M-1 to R-49; M-1 to Q-48; M-1 to L-47; M-1 to L-46; M-1 to Q-45; M-1 to Y-44; M-1 to L-43; M-1 to D-42; M-1 to P-41; M-1 to D-40; M-1 to R-39; M-1 to K-38; M-1 to S-37; M-1 to R-36; M-1 to G-35; M-1 to G-34; M-1 to G-33; M-1 to P-32; M-1 to V-31; M-1 to V-30; M-1 to E-29; M-1 to E-28; M-1 to Q-27; M-1 to P-26; M-1 to E-25; M-1 to K-24; M-1 to C-23; M-1 to V-22; M-1 to A-21; M-1 to G-20; M-1 to F-19; M-1 to S-18; M-1 to Q-17; M-1 to A-16; M-1 to L-15; M-1 to S-14; M-1 to F-13; M-1 to A-12; M-1 to L-11; M-1 to I-10; M-1 to A-9; M-1 to T-8; M-1 to F-7; M-1 to L-6 of the neurokinin B sequence of SEQ ID NO:2.

The invention also provides antibodies that bind polypeptides having one or more amino acids deleted from both the amino and the carboxyl termini of a neurokinin B polypeptide, which may be described generally as having residues $n^1$-$m^1$ or $n^1$-$m^2$ of SEQ ID NO:2, where $n^1$, $m^1$, and $m^2$ are integers as described above.

The present application is also directed to antibodies that bind proteins containing polypeptides at least 90%, 95%, 96%, 97%, 98% or 99% identical to the neurokinin B polypeptide sequence set forth herein as $n^1$-$m^1$ or $n^1$-$m^2$. In preferred embodiments, the present invention encompasses antibodies that bind proteins containing polypeptides at least 90%, 95%, 96%, 97%, 98% or 99% identical to polypeptides having the amino acid sequence of the specific neurokinin B N- and/or C-terminal deletions recited herein.

In certain preferred embodiments, antibodies of the invention bind neurokinin B fusion proteins as described above wherein the neurokinin B portion of the fusion protein are those described as $n^1$-$m^1$ or $n^1$-$m^2$ herein.

Preferably, antibodies of the present invention bind fragments of neurokinin B comprising, or alternatively consisting of, the mature protein; i.e., residues 81-90 of SEQ ID NO:2.

It will be recognized in the art that some amino acid sequence of neurokinin B can be varied without significant effect of the structure or function of the protein. If such differences in sequence are contemplated, it should be remembered that there will be critical areas on the protein, which determine activity. Such areas will usually comprise residues which make up the ligand binding site or which form tertiary structures which affect these domains.

Thus, the invention further includes antibodies that bind variations of the neurokinin B protein which show substantial neurokinin B protein activity or which include regions of neurokinin B such as the protein fragments discussed below. Such mutants include deletions, insertions, inversions, repeats, and type substitution. Guidance concerning which amino acid changes are likely to be phenotypically silent can be found in Bowie, J. U. et al., *Science* 247:1306-1310 (1990).

Thus, antibodies of the present invention may bind a fragment, derivative, or analog of the polypeptide of SEQ ID NO:2, or that encoded by the cDNA in ATCC deposit 97922 and/or ATCC Deposit No. 97375. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the neurokinin B protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the antibodies of the present invention may bind a neurokinin B polypeptide that contains one or more amino acid substitutions, deletions or additions, either from natural mutations or human manipulation.

As indicated, changes are preferably of a minor nature, such as conservative amino acid substitutions that do not significantly affect the folding or activity of the protein (see Table 2).

TABLE 2

Conservative Amino Acid Substitutions.

| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of SEQ ID NO:2 and/or any of the polypeptide fragments described herein is 1-10, 5-10, 1-5, 1-3 or 1-2.

In specific embodiments, the antibodies of the invention bind neurokinin B polypeptides or fragments or variants thereof (especially a fragment comprising or alternatively consisting of, the mature form of neurokinin B), that contains any one or more of the following conservative mutations in neurokinin B: M1 replaced with A, G, I, L, S, T, or V; R2 replaced with H, or K; I3 replaced with A, G, L, S, T, M, or V; M4 replaced with A, G, I, L, S, T, or V; L5 replaced with A, G, I, S, T, M, or V; L6 replaced with A, G, I, S, T, M, or V; F7 replaced with W, or Y; T8 replaced with A, G, I, L, S, M, or V; A9 replaced with G, I, L, S, T, M, or V; I10 replaced with A, G, L, S, T, M, or V; L11 replaced with A, G, I, S, T, M, or V; A12 replaced with G, I, L, S, T, M, or V; F13 replaced with W, or Y; S14 replaced with A, G, I, L, T, M, or V; L15 replaced with A, G, I, S, T, M, or V; A16 replaced with G, I, L, S, T, M, or V; Q17 replaced with N; S18 replaced with A, G, I, L, T, M, or V; F19 replaced with W, or Y; G20 replaced with A, I, L, S, T, M, or V; A21 replaced with G, I, L, S, T, M, or V; V22 replaced with A, G, I, L, S, T, or M; K24 replaced with H, or R; E25 replaced with D; Q27 replaced with N; E28 replaced with D; E29 replaced with D; V30 replaced with A, G, I, L, S, T, or M; V31 replaced with A, G, I, L, S, T, or M; G33 replaced with A, I, L, S, T, M, or V; G34 replaced with A, I, L, S, T, M, or V; G35 replaced with A, I, L, S, T, M, or V; R36 replaced with H, or K; S37 replaced with A, G, I, L, T, M, or V; K38 replaced with H, or R; R39 replaced with H, or K; D40 replaced with E; D42 replaced with E; L43 replaced with A, G, I, S, T, M, or V; Y44 replaced with F, or W; Q45 replaced with N; L46 replaced with A, G, I, S, T, M, or V; L47 replaced with A, G, I, S, T, M, or V; Q48 replaced with N; R49 replaced with H, or K; L50 replaced with A, G, I, S, T, M, or V; F51 replaced with W, or Y; K52 replaced with H, or R; S53 replaced with A, G, I, L, T, M, or V; H54 replaced with K, or R; S55 replaced with A, G, I, L, T, M, or V; S56 replaced with A, G, I, L, T, M, or V; L57 replaced with A, G, I, S, T, M, or V; E58 replaced with D; G59 replaced with A, I, L, S, T, M, or V; L60 replaced with A, G, I, S, T, M, or V; L61 replaced with A, G, I, S, T, M, or V; K62 replaced with H, or R; A63 replaced with G, I, L, S, T, M, or V; L64 replaced with A, G, I, S, T, M, or V; S65 replaced with A, G, I, L, T, M, or V; Q66 replaced with N; A67 replaced with G, I, L, S, T, M, or V; S68 replaced with A, G, I, L, T, M, or V; T69 replaced with A, G, I, L, S, M, or V; D70 replaced with E; K72 replaced with H, or R; E73 replaced with D; S74 replaced with A, G, I, L, T, M, or V; T75 replaced with A, G, I, L, S, M, or V; S76 replaced with A, G, I, L, T, M, or V; E78 replaced with D; K79 replaced with H, or R; R80 replaced with H, or K; D81 replaced with E; M82 replaced with A, G, I, L, S, T, or V; H83 replaced with K, or R; D84 replaced with E; F85 replaced with W, or Y; F86 replaced with W, or Y; V87 replaced with A, G, I, L, S, T, or M; G88 replaced with A, I, L, S, T, M, or V; L89 replaced with A, G, I, S, T, M, or V; M90 replaced with A, G, I, L, S, T, or V; G91 replaced with A, I, L, S, T, M, or V; K92 replaced with H, or R; R93 replaced with H, or K; S94 replaced with A, G, I, L, T, M, or V; V95 replaced with A, G, I, L, S, T, or M; Q96 replaced with N; D98 replaced with E; S99 replaced with A, G, I, L, T, M, or V; T101 replaced with A, G, I, L, S, M, or V; D102 replaced with E; V103 replaced with A, G, I, L, S, T, or M; N104 replaced with Q; Q105 replaced with N; E106 replaced with D; N107 replaced with Q; V108 replaced with A, G, I, L, S, T, or M; S110 replaced with A, G, I, L, T, M, or V; F111 replaced with W, or Y; G112 replaced with A, I, L, S, T, M, or V; I113 replaced with A, G, L, S, T, M, or V; L114 replaced with A, G, I, S, T, M, or V; K115 replaced with H, or R; Y116 replaced with F, or W; R119 replaced with H, or K; A120 replaced with G, I, L, S, T, M, or V; E121 replaced with D of SEQ ID NO:2.

In specific embodiments, the antibodies of the invention bind neurokinin B polypeptides or fragments or variants thereof (especially a fragment comprising or alternatively consisting of, the mature form of neurokinin B), that contains any one or more of the following non-conservative mutations in neurokinin B: M1 replaced with D, E, H, K, R, N, Q, F, W, Y, P, or C; R2 replaced with D, E, A, G, I, L, S, T, M, V, N, Q, F, W, Y, P, or C; I3 replaced with D, E, H, K, R, N, Q, F, W, Y, P, or C; M4 replaced with D, E, H, K, R, N, Q, F, W, Y, P, or C; L5 replaced with D, E, H, K, R, N, Q, F, W, Y, P, or C; L6 replaced with D, E, H, K, R, N, Q, F, W, Y, P, or C; F7 replaced with D, E, H, K, R, N, Q, A, G, I, L, S, T, M, V, P, or C; T8 replaced with D, E, H, K, R, N, Q, F, W, Y, P, or C; A9 replaced with D, E, H, K, R, N, Q, F, W, Y, P, or C; I10 replaced with D, E, H, K, R, N, Q, F, W, Y, P, or C; L11 replaced with D, E, H, K, R, N, Q, F, W, Y, P, or C; A12 replaced with D, E, H, K, R, N, Q, F, W, Y, P, or C; F13 replaced with D, E, H, K, R, N, Q, A, G, I, L, S, T, M, V, P, or C; S14 replaced with D, E, H, K, R, N, Q, F, W, Y, P, or C; L15 replaced with D, E, H, K, R, N, Q, F, W, Y, P, or C; A16 replaced with D, E, H, K, R, N, Q, F, W, Y, P, or C; Q17 replaced with D, E, H, K, R, A, G, I, L, S, T, M, V, F, W, Y, P, or C; S18 replaced with D, E, H, K, R, N, Q, F, W, Y, P, or C; F19 replaced with D, E, H, K, R, N, Q, A, G, I, L, S, T, M, V, P, or C; G20 replaced with D, E, H, K, R, N, Q, F, W, Y, P, or C; A21 replaced with D, E, H, K, R, N, Q, F, W, Y, P, or C; V22 replaced with D, E, H, K, R, N, Q, F, W, Y, P, or C; C23 replaced with D, E, H, K, R, A, G, I, L, S, T, M, V, N, Q, F, W, Y, or P; K24 replaced with D, E, A, G, I, L, S, T, M, V, N, Q, F, W, Y, P, or C; E25 replaced with H, K, R, A, G, I, L, S, T, M, V, N, Q, F, W, Y, P, or C; P26 replaced with D, E, H, K, R, A, G, I, L, S, T, M, V, N, Q, F, W, Y, or C; Q27 replaced with D, E, H, K, R, A, G, I, L, S, T, M, V, F, W, Y, P, or C; E28 replaced with H, K, R, A, G, I, L, S, T, M, V, N, Q, F, W, Y, P, or C; E29 replaced with H, K, R, A, G, I, L, S, T, M, V, N, Q, F, W, Y, P, or C; V30 replaced with D, E, H, K, R, N, Q; F, W, Y, P, or C; V31 replaced with D, E, H, K, R, N, Q, F, W, Y, P, or C; P32 replaced with D, E, H, K, R, A, G, I, L, S, T, M, V, N, Q, F, W, Y, or C; G33 replaced with D, E, H, K, R, N, Q, F, W, Y, P, or C; G34 replaced with D, E, H, K, R, N, Q, F, W, Y, P. or C; G35 replaced with D, E, H, K, R, N, Q, F, W, Y, P, or C; R36 replaced with D, E, A, G, I, L, S, T, M, V, N, Q, F, W, Y, P, or C; S37 replaced with D, E, H, K, R, N, Q, F, W, Y, P, or C; K38 replaced with D, E, A, G, I, L, S, T, M, V, N, Q, F, W, Y, P, or C; R39 replaced with D, E, A, G, I, L, S, T, M, V, N, Q, F, W, Y, P, or C; D40 replaced with H, K, R, A, G, I, L, S, T, M, V, N, Q, F, W, Y, P, or C; P41 replaced with D, E, H, K, R, A, G, I, L, S, T, M, V, N, Q, F, W, Y, or C; D42 replaced with H, K, R, A, G, I, L, S, T, M, V, N, Q, F, W, Y, P, or C; L43 replaced with D, E, H, K, R, N, Q, F, W, Y, P, or C; Y44 replaced with D, E, H, K, R, N, Q, A, G, I, L, S, T, M, V, P, or C; Q45 replaced with D, E, H, K, R, A, G, I, L, S, T, M, V, F, W, Y, P, or C; L46 replaced with D, E, H, K, R, N, Q, F, W, Y, P, or C; L47 replaced with D, E, H, K, R, N, Q, F, W, Y, P, or C; Q48 replaced with D, E, H, K, R, A, G, I, L, S, T, M, V, F, W, Y, P, or C; R49 replaced with D, E, A, G, I, L, S, T, M, V, N, Q, F, W, Y, P, or C; L50 replaced with D, E, H, K, R, N, Q, F, W, Y, P, or C; F51 replaced with D, E, H, K, R, N, Q, A, G, I, L, S, T, M, V, P, or C; K52 replaced with D, E, A, G, I, L, S, T, M, V, N, Q, F, W, Y, P, or C; S53 replaced with D, E, H, K, R, N, Q, F, W, Y, P, or C; H54 replaced with D, E, A, G, I, L, S, T, M, V, N, Q, F, W, Y, P, or C; S55 replaced with D, E, H, K, R, N, Q, F, W, Y, P, or C; S56 replaced with D, E, H, K, R, N, Q, F, W, Y, P, or C; L57 replaced with D, E, H, K, R, N, Q, F, W, Y, P, or C; E58 replaced with H, K, R, A, G, I, L, S, T, M, V, N, Q, F, W, Y, P, or C; G59 replaced with D, E, H, K, R, N, Q, F, W, Y, P, or C; L60 replaced with D, E, H, K, R, N, Q, F, W, Y, P, or C; L61 replaced with D, E, H, K, R, N, Q, F, W, Y, P, or C; K62 replaced with D, E, A, G, I, L, S, T, M, V, N, Q, F, W, Y, P, or C; A63 replaced with D, E, H, K, R, N, Q, F, W, Y, P, or C; L64 replaced with D, E, H, K, R, N, Q, F, W, Y, P, or C; S65 replaced with D, E, H, K, R, N, Q, F, W, Y, P, or C; Q66 replaced with D, E, H, K, R, A, G, I, L, S, T, M, V, F, W, Y, P, or C; A67 replaced with D, E, H, K, R, N, Q, F, W, Y, P, or C; S68 replaced with D, E, H, K, R, N, Q, F, W, Y, P, or C; T69 replaced with D, E, H, K, R, N, Q, F, W, Y, P, or C; D70 replaced with H, K, R, A, G, I, L, S, T, M, V, N, Q, F, W, Y, P, or C; P71 replaced with D, E, H, K, R, A, G, I, L, S, T, M, V, N, Q, F, W, Y, or C; K72 replaced with D, E, A, G, I, L, S, T, M, V, N, Q, F, W, Y, P, or C; E73 replaced with H, K, R, A, G, I, L, S, T, M, V, N, Q, F, W, Y, P, or C; S74 replaced with D, E, H, K, R, N, Q, F, W, Y, P, or C; T75 replaced with D, E, H, K, R, N, Q, F, W, Y, P, or C; S76 replaced with D, E, H, K, R, N, Q, F, W, Y, P, or C; P77 replaced with D, E, H, K, R, A, G, I, L, S, T, M, V, N, Q, F, W, Y, or C; E78 replaced with H, K, R, A, G, I, L, S, T, M, V, N, Q, F, W, Y, P, or C; K79 replaced with D, E, A, G, I, L, S, T, M, V, N, Q, F, W, Y, P, or C; R80 replaced with D, E, A, G, I, L, S, T, M, V, N, Q, F, W, Y, P, or C; D81 replaced with H, K, R, A, G, I, L, S, T, M, V, N, Q, F, W, Y, P, or C; M82 replaced with D, E, H, K, R, N, Q, F, W, Y, P, or C; H83 replaced with D, E, A, G, I, L, S, T, M, V, N, Q, F, W, Y, P, or C; D84 replaced with H, K, R, A, G, I, L, S, T, M, V, N, Q, F, W, Y, P, or C; F85 replaced with D, E, H, K, R, N, Q, A, G, I, L, S, T, M, V, P, or C; F86 replaced with D, E, H, K, R, N, Q, A, G, I, L, S, T, M, V, P, or C; V87 replaced with D, E, H, K, R, N, Q, F, W, Y, P, or C; G88 replaced with D, E, H, K, R, N, Q, F, W, Y, P, or C; L89 replaced with D, E, H, K, R, N, Q, F, W, Y, P, or C; M90 replaced with D, E, H, K, R, N, Q, F, W, Y, P, or C; G91 replaced with D, E, H, K, R, N, Q, F, W, Y, P, or C; K92 replaced with D, E, A, G, I, L, S, T, M, V, N, Q, F, W, Y, P, or C; R93 replaced with D, E, A, G, I, L, S, T, M, V, N, Q, F, W, Y, P, or C; S94 replaced with D, E, H, K, R, N, Q, F, W, Y, P, or C; V95 replaced with D, E, H, K, R, N, Q, F, W, Y, P, or C; Q96 replaced with D, E, H, K, R, A, G, I, L, S, T, M, V, F, W, Y, P, or C; P97 replaced with D, E, H, K, R, A, G, I, L, S, T, M, V, N, Q, F, W, Y, or C; D98 replaced with H, K, R, A, G, I, L, S, T, M, V, N, Q, F, W, Y, P, or C; S99 replaced with D, E, H, K, R, N, Q, F, W, Y, P, or C; P100 replaced with D, E, H, K, R, A, G, I, L, S, T, M, V, N, Q, F, W, Y, or C; T101 replaced with D, E, H, K, R, N, Q, F, W, Y, P, or C; D102 replaced with H, K, R, A, G, I, L, S, T, M, V, N, Q, F, W, Y, P, or C; V103 replaced with D, E, H, K, R, N, Q, F, W, Y, P, or C; N104 replaced with D, E, H, K, R, A, G, I, L, S, T, M, V, F, W, Y, P, or C; Q105 replaced with D, E, H, K, R, A, G, I, L, S, T, M, V, F, W, Y, P, or C; E106 replaced with H, K, R, A, G, I, L, S, T, M, V, N, Q, F, W, Y, P, or C; N107 replaced with D, E, H, K, R, A, G, I, L, S, T, M, V, F, W, Y, P, or C; V108 replaced with D, E, H, K, R, N, Q, F, W, Y, P, or C; P109 replaced with D, E, H, K, R, A, G, I, L, S, T, M, V, N, Q, F, W, Y, or C; S110 replaced with D, E, H, K, R, N, Q, F, W, Y, P, or C; F111 replaced with D, E, H, K, R, N, Q, A, G, I, L, S, T, M, V, P, or C; G112 replaced with D, E, H, K, R, N, Q, F, W, Y, P, or C; I113 replaced with D, E, H, K, R, N, Q, F, W, Y, P, or C; L114 replaced with D, E, H, K, R, N, Q, F, W, Y, P, or C; K115 replaced with D, E, A, G, I, L, S, T, M, V, N, Q, F, W, Y, P, or C; Y116 replaced with D, E, H, K, R, N, Q, A, G, I, L, S, T, M, V, P, or C; P117 replaced with D, E, H, K, R, A, G, I, L, S, T, M, V, N, Q, F, W, Y, or C; P118 replaced with D, E, H, K, R, A, G, I, L, S, T, M, V, N, Q, F, W, Y, or C; R119 replaced with D, E, A, G, I, L, S, T, M, V, N, Q, F, W, Y, P, or C; A120 replaced with D, E, H, K, R, N, Q, F, W, Y, P, or C; E121 replaced with H, K, R, A, G, I, L, S, T, M, V, N, Q, F, W, Y, P, or C of SEQ ID NO:2.

Amino acids in the neurokinin B protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of neurokinin B that are essential for neurokinin B function. In other preferred embodiments, antibodies of the present invention bind regions of neurokinin B that are essential for neurokinin B function and inhibit or abolish neurokinin B function. In other preferred embodiments, antibodies of the present invention bind regions of neurokinin B that are essential for neurokinin B function and enhance neurokinin B function.

Additionally, protein engineering may be employed to improve or alter the characteristics of neurokinin B polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified neurokinin B polypeptides.

Non-naturally occurring variants of neurokinin B may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses antibodies that bind neurokinin B derivatives and analogs that have one or more amino acid residues deleted, added, and/or substituted to generate neurokinin B polypeptides that have better binding activity, better therapeutic activity, are expressed better, or are better suited to scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the neurokinin B polypeptides and/or an amino acid deletion at the second position of any one or more such recognition sequences will prevent glycosylation of the neurokinin B at the modified tripeptide sequence (see, e.g., Miyajimo et al., *EMBO J* 5(6): 1193-1197). Additionally, one or more of the amino acid residues of neurokinin B polypeptides (e.g., arginine and lysine residues) may be deleted or substituted with another residue to eliminate undesired processing by proteases such as, for example, furins or kexins.

Antibodies of the Invention May Bind Modified Neurokinin B Polypeptides

It is specifically contemplated that antibodies of the present invention may bind modified forms of neurokinin B protein.

In specific embodiments, antibodies of the present invention bind neurokinin B polypeptides (such as those described above) including, but not limited to naturally purified neurokinin B polypeptides, neurokinin B polypeptides produced by chemical synthetic procedures, and neurokinin B polypeptides produced by recombinant techniques from a prokaryotic or eukaryotic host, including, for example, bacterial, yeast, higher plant, insect and mammalian cells using, for example, the recombinant compositions and methods described above. Depending upon the host employed in a recombinant production procedure, the polypeptides may be glycosylated or non-glycosylated. In addition, neurokinin B polypeptides may also include an initial modified methionine residue, in some cases as a result of host-mediated processes.

In addition, neurokinin B proteins that antibodies of the present invention may bind can be chemically synthesized using techniques known in the art (e.g., see Creighton, Proteins: Structures and Molecular Principles, W.H. Freeman & Co., N.Y. (1983), and Hunkapiller, et al., *Nature* 310:105-111 (1984)). For example, a peptide corresponding to a fragment of a neurokinin B polypeptide can be synthesized by use of a peptide synthesizer. Furthermore, if desired, nonclassical amino acids or chemical amino acid analogs can be introduced as a substitution or addition into the neurokinin B polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally, encompasses antibodies that bind neurokinin B polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications to neurokinin B polypeptides include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are antibodies that bind chemically modified derivatives of neurokinin B polypeptide which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each neurokinin B polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

As mentioned the antibodies of the present invention may bind neurokinin B polypeptides that are modified by either natural processes, such as posttranslational processing, or by chemical modification techniques, which are well known in the art. It will be appreciated that the same type of modification may be present in the same or varying degrees at several sites in a given neurokinin B polypeptide. neurokinin B polypeptides may be branched, for example, as a result of ubiquitination, and they may be cyclic, with or without branching. Cyclic, branched, and branched cyclic neurokinin B polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

Antibodies that Specifically Bind Neurokinin B

In one embodiment, the invention provides antibodies (e.g., anti-neurokinin B antibodies comprising two heavy chains and two light chains linked together by disulfide bridges) that specifically bind a neurokinin B polypeptide (e.g., SEQ ID NO:2) or fragments or variants thereof, wherein the amino acid sequence of the heavy chain and the amino acid sequence of the light chain are the same as the amino acid sequence of a heavy chain and a light chain of an antibody expressed by one or more cell lines referred to in Table 1. In another embodiment, the invention provides antibodies (each consisting of two heavy chains and two light chains linked together by disulfide bridges to form an antibody) that specifically bind a neurokinin B polypeptide (e.g., SEQ ID NO:2) or fragments or variants thereof, wherein the amino acid sequence of the heavy chain or the amino acid sequence of the light chain are the same as the amino acid sequence of a heavy chain or a light chain of an antibody expressed by one or more cell lines referred to in Table 1. Specific binding to neurokinin B polypeptides may be determined by immunoassays known in the art or described herein for assaying specific antibody-antigen binding. Molecules comprising, or alternatively consisting of, fragments or variants of these antibodies that specifically bind to neurokinin B are also encompassed by the invention, as are nucleic acid molecules encoding these antibodies molecules, fragments and/or variants (e.g., SEQ ID NOs:3-21).

In one embodiment of the present invention, antibodies that specifically bind to neurokinin B or a fragment or variant thereof, comprise a polypeptide having the amino acid sequence a heavy chain of an antibody expressed by at least one of the cell lines referred to in Table 1 and/or a light chain of an antibody expressed by at least one of the cell lines referred to in Table 1.

In another embodiment of the present invention, antibodies that specifically bind to neurokinin B or a fragment or variant thereof, comprise a polypeptide having the amino acid sequence of any one of the VH domains of at least one of the scFvs referred to in Table 1 and/or any one of the VL domains of at least one of the scFvs referred to in Table 1. In preferred embodiments, antibodies of the present invention comprise the amino acid sequence of a VH domain and VL domain of the scFvs referred to in Table 1. Molecules comprising, or alternatively consisting of, antibody fragments or variants of the VH and/or VL domains of at least one of the scFvs referred to in Table 1 that specifically bind to neurokinin B are also encompassed by the invention, as are nucleic acid molecules encoding these VH and VL domains, molecules, fragments and/or variants.

The present invention also provides antibodies that specifically bind to a polypeptide, or polypeptide fragment or variant of neurokinin B, wherein said antibodies comprise, or alternatively consist of, a polypeptide having an amino acid sequence of any one, two, three, or more of the VH CDRs contained in a VH domain of one or more scFvs referred to in Table 1. In particular, the invention provides antibodies that specifically bind neurokinin B, comprising, or alternatively consisting of, a polypeptide having the amino acid sequence of a VH CDR1 contained in a VH domain of one or more scFvs referred to in Table 1. In another embodiment, antibodies that specifically bind neurokinin B, comprise, or alternatively consist of, a polypeptide having the amino acid sequence of a VH CDR2 contained in a VH domain of one or more scFvs referred to in Table 1. In a preferred embodiment, antibodies that specifically bind neurokinin B, comprise, or alternatively consist of a polypeptide having the amino acid sequence of a VH CDR3 contained in a VH domain of one or more scFvs referred to in Table 1. Molecules comprising, or alternatively consisting of, these antibodies, or antibody fragments or variants thereof, that specifically bind to neurokinin B or a neurokinin B fragment or variant thereof are also encompassed by the invention, as are nucleic acid molecules encoding these antibodies, molecules, fragments and/or variants (e.g., SEQ ID NOs:3-21).

The present invention also provides antibodies that specifically bind to a polypeptide, or polypeptide fragment or variant of neurokinin B, wherein said antibodies comprise, or alternatively consist of, a polypeptide having an amino acid sequence of any one, two, three, or more of the VL CDRs contained in a VL domain of one or more scFvs referred to in Table 1. In particular, the invention provides antibodies that specifically bind neurokinin B, comprising, or alternatively consisting of, a polypeptide having the amino acid sequence of a VL CDR1 contained in a VL domain of one or more scFvs referred to in Table 1. In another embodiment, antibodies that specifically bind neurokinin B, comprise, or alternatively consist of, a polypeptide having the amino acid sequence of a VL CDR2 contained in a VL domain of one or more scFvs referred to in Table 1. In a preferred embodiment, antibodies that specifically bind neurokinin B, comprise, or alternatively consist of a polypeptide having the amino acid sequence of a VL CDR3 contained in a VL domain of one or more scFvs referred to in Table 1. Molecules comprising, or alternatively consisting of, these antibodies, or antibody fragments or variants thereof, that specifically bind to neurokinin B or a neurokinin B fragment or variant thereof are also encompassed by the invention, as are nucleic acid molecules encoding these antibodies, molecules, fragments and/or variants (e.g., SEQ ID NOs:3-21).

The present invention also provides antibodies (including molecules comprising, or alternatively consisting of, antibody fragments or variants) that specifically bind to a neurokinin B polypeptide or polypeptide fragment or variant of neurokinin B, wherein said antibodies comprise, or alternatively consist of, one, two, three, or more VH CDRs and one, two, three or more VL CDRs, as contained in a VH domain or VL domain of one or more scFvs referred to in Table 1. In particular, the invention provides for antibodies that specifically bind to a polypeptide or polypeptide fragment or variant of neurokinin B, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a VH domain or VL domain of one or more scFvs referred to in Table 1. In a preferred embodiment, one or more of these combinations are from the same scFv as disclosed in Table 1. Molecules comprising, or alternatively consisting of, fragments or variants of these antibodies, that specifically bind to neurokinin B are also encompassed by the invention, as are nucleic acid molecules encoding these antibodies, molecules, fragments or variants (e.g., SEQ ID NOs:3-21).

In other preferred embodiments, the invention provides antibodies that competitively inhibit binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide. In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a Neurokinin B polypeptide by between 1% and 10% in a competitive inhibition assay. In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by between 1% and 10% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 10% and up to 20% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 20% and up to 30% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 30% and up to 40% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 40% and up to 50% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 50% and up to 60% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 60% and up to 70% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 70% and up to 80% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 80% and up to 90% in a competitive inhibition assay.

In preferred embodiments, the invention provides antibodies that which reduce the binding of an antibody comprising a fragment (e.g., VH domain, VL domain, VHCDR1, VHCDR2, VHCDR3, VLCDR1, VLCDR2, or VLCDR3) or variant of an scFv referred to in Table 1 to a neurokinin B polypeptide by at least 90% and up to 100% in a competitive inhibition assay.

Nucleic Acid Molecules Encoding Anti-Neurokinin B Antibodies

The present invention also provides for nucleic acid molecules, generally isolated, encoding an antibody of the invention (including molecules comprising, or alternatively consisting of, antibody fragments or variants thereof). In specific embodiments, the nucleic acid molecules encoding an antibody of the invention comprise, or alternatively consist of SEQ ID NOs:3-21 or fragments or variants thereof.

In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 and a VL domain having an amino acid sequence of VL domain of at least one of the scFvs referred to in Table 1. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 or a VL domain having an amino acid sequence of a VL domain of at least one of the scFvs referred to in Table 1.

The present invention also provides antibodies that comprise, or alternatively consist of, variants (including derivatives) of the antibody molecules (e.g., the VH domains and/or VL domains) described herein, which antibodies specifically bind to neurokinin B or fragment or variant. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind a neurokinin B receptor).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to specifically bind a neurokinin B receptor) can be determined using techniques described herein or by routinely modifying techniques known in the art.

In a specific embodiment, an antibody of the invention (including a molecule comprising, or alternatively consisting of, an antibody fragment or variant thereof), that specifically binds neurokinin B polypeptides or fragments or variants thereof, comprises, or alternatively consists of, an amino acid sequence encoded by a nucleotide sequence that hybridizes to a nucleotide sequence that is complementary to that encoding one of the VH or VL domains of one or more scFvs referred to in Table 1 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3). Nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that specifically binds to a neurokinin B polypeptide or fragments or variants of a neurokinin B polypeptide, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of at least one of the scFvs referred to in Table 1.

In another embodiment, an antibody (including a molecule comprising, or alternatively consisting of, an antibody fragment or variant thereof), that specifically binds to a neurokinin B polypeptide or fragments or variants of a neurokinin B polypeptide, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of at least one of the scFvs referred to in Table 1.

Methods of Producing Antibodies

Antibodies in accordance with the invention are preferably prepared utilizing a phage scFv display library. Technologies utilized for achieving the same are disclosed in the patents, applications, and references disclosed herein.

In phage display methods, functional antibody domains are displayed on the surface of phage particles, which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a neurokinin B polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280(1994); PCT application No. PCT/GB91/O1 134; PCT publications WO 90/02809; WO 91/10737; WO 92/01047; WO 92/18719; WO 93/11236; WO 95/15982; WO 95/20401; WO97/13844; and U.S. Pat. Nos. 5,698,426; 5,223,409; 5,403,484; 5,580,717; 5,427,908;

5,750,753; 5,821,047; 5,571,698; 5,427,908; 5,516,717; 5,780,225; 5,658,727; 5,735,743 and 5,969,108; each of which is incorporated herein by reference in its entirety.

For some uses, such as for in vitro affinity maturation of an antibody of the invention, it may be useful to express the VH and VL domains of one or more scFvs referred to in Table 1 as single chain antibodies or Fab fragments in a phage display library. For example, the cDNAs encoding the VH and VL domains of the scFvs referred to in Table 1 may be expressed in all possible combinations using a phage display library, allowing for the selection of VH/VL combinations that bind neurokinin B polypeptides with preferred binding characteristics such as improved affinity or improved off rates. Additionally, VH and VL domains—the CDR regions of the VH and VL domains of the scFvs referred to in Table 1, in particular, may be mutated in vitro. Expression of VH and VL domains with "mutant" CDRs in a phage display library allows for the selection of VH/VL combinations that bind neurokinin B polypeptides with preferred binding characteristics such as improved affinity or improved off rates.

Additional Methods of Producing Antibodies

Antibodies of the invention (including antibody fragments or variants) can be produced by any method known in the art. For example, it will be appreciated that antibodies in accordance with the present invention can be expressed in cell lines including, but not limited to, myeloma cell lines and hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains of the scFvs referred to in Table 1. In order to isolate the VH and VL domains from bacteria transfected with a vector containing the scFv, PCR primers complementary to VH or VL nucleotide sequences (See Example 2), may be used to amplify the VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art. Alternatively, the VH and VL domains may be amplified using vector specific primers designed to amplify the entire scFv, (i.e., the VH domain, linker and VL domain.)

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH or VL domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995), which are herein incorporated in their entireties by reference).

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. If the amino acid sequences of the VH domains, VL domains and CDRs thereof, are known, nucleotide sequences encoding these antibodies can be determined using methods well known in the art, i.e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly $A^+$ RNA, isolated from, any tissue or cells expressing the antibody, such as hybridoma cells or Epstein Barr virus transformed B cell lines that express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, VH and VL domains of one or more scFvs referred to in Table 1, or fragments or variants thereof, are inserted within antibody framework regions using recombinant DNA techniques known in the art. In a specific embodiment, one, two, three, four, five, six, or more of the CDRs of VH and/or VL domains of one or more scFvs referred to in Table 1, or fragments or variants thereof, is inserted within antibody framework regions using recombinant DNA techniques known in the art. The antibody framework regions may be naturally occurring or consensus antibody framework regions, and preferably human antibody framework regions (see, e.g., Chothia et al., J. Mol. Biol. 278: 457-479 (1998) for a listing of human antibody framework regions, the contents of which are hereby incorporated by reference in its entirety). Preferably, the polynucleotides generated by the combination of the antibody framework regions and CDRs encode an antibody (including molecules comprising, or alternatively consisting of, antibody fragments or variants thereof) that specifically binds to neurokinin B. Preferably, as discussed supra, polynucleotides encoding variants of antibodies or antibody fragments having one or more amino acid substitutions may be made within the framework regions, and, preferably, the amino acid substitutions do not significantly alter binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

Xenomouse™ Technology

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (Mabs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XenoMouse™ strains as published in 1994. See Green et al. Nature Genetics 7:13-21 (1994). The XenoMouse™ strains were engineered with yeast artificial chromosomes (YACS) containing 245 kb and 10 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. Nature Genetics 15:146-156 (1997), Green and Jakobovits J Exp. Med. 188: 483-495 (1998), Green, Journal of Immunological Methods 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, U.S. Ser. No. 07/710,515, filed Nov. 8, 1990, U.S. Ser. No. 07/919,297, filed Jul. 24, 1992, U.S. Ser. No. 07/922,649, filed Jul. 30, 1992, filed U.S. Ser. No. 08/031,801, filed Mar. 15, 1993, U.S. Ser. No. 08/112,848, filed Aug. 27, 1993, U.S. Ser. No. 08/234,145, filed Apr. 28, 1994, U.S. Ser. No. 08/376,279, filed Jan. 20, 1995, U.S. Ser. No. 08/430,938, Apr. 27, 1995, U.S. Ser. No. 0-8/464,584, filed Jun. 5, 1995, U.S. Ser. No. 08/464,582, filed Jun. 5, 1995, U.S. Ser. No. 08/471,191, filed Jun. 5, 1995, U.S. Ser. No. 08/462,837, filed Jun. 5, 1995, U.S. Ser. No. 08/486,853, filed Jun. 5, 1995, U.S. Ser. No. 08/486,857, filed Jun. 5, 1995, U.S. Ser. No. 08/486,859, filed Jun. 5, 1995, U.S. Ser. No. 08/462,513, filed Jun. 5, 1995, U.S. Ser. No. 08/724,752, filed Oct. 2, 1996, and U.S. Ser. No. 08/759,620, filed Dec. 3, 1996. See also Mendez et al. Nature Genetics 15:146-156 (1997) and Green and Jakobovits J Exp. Med. 188:483 495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against neurokinin B polypeptides in order to vitiate concerns and/or effects of HAMA or HACA responses.

Monoclonal antibodies specific for neurokinin B polypeptides may be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). Briefly, XenoMouse™ mice may be immunized with neurokinin B polypeptides. After immunization, the splenocytes of such mice may be extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones, which secrete antibodies capable of binding the neurokinin B polypeptides.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716,111; and PCT publications WO 98/46645, WO 98/50435, WO 98/24893, WO98/16654, WO 96/34096, WO 96/35735, and WO 91/10741, each of which is incorporated herein by reference in its entirety. In a specific embodiment, antibodies of the present invention comprise one or more VH and VL domains of the invention and constant regions from another immunoglobulin molecule, preferably a human immunoglobulin molecule. In a specific embodiment, antibodies of the present invention comprise one or more CDRs corresponding to the VH and VL domains of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the VH or VL domains of one or more scFvs referred to in Table 1, or fragments or variants thereof, and framework regions (and, optionally one or more CDRs not present in the antibodies expressed by scFvs referred to in Table 1) from a human immunoglobulin molecule. In a preferred embodiment, an antibody of the present invention comprises a VH CDR3, VL CDR3, or both, corresponding to the same scFv, or different scFvs selected from the scFvs referred to in Table 1, or fragments or variants thereof, and framework regions from a human immunoglobulin.

A chimeric antibody is a molecule in which different portions of the antibody are derived from different immunoglobulin molecules such as antibodies having a human variable region and a non-human (e.g., murine) immunoglobulin constant region or vice versa. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a murine, canine or feline immunoglobulin molecule) (or vice versa) can be produced using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352). In a preferred embodiment, chimeric antibodies comprise a human CDR3 having an amino acid sequence of any one of the VH CDR3s or VL CDR3s of a VH or VL domain of one or more of the scFvs referred to in Table 1, or a variant thereof, and non-human framework regions or human framework regions different from those of the frameworks in the corresponding scFv disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 352:323 (1988), which are incorporated herein by reference in their entireties.)

Intrabodies are antibodies, often scFvs, that are expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., Hum. Gene Ther. 5:595-601 (1994); Marasco, W. A., Gene Ther. 4:11-15 (1997); Rondon and Marasco, Annu. Rev. Microbiol. 51:257-283 (1997); Proba et al., J. Mol. Biol. 275:245-253 (1998); Cohen et al., Oncogene 17:2445-2456 (1998); Ohage and Steipe, J. Mol. Biol. 291:1119-1128 (1999); Ohage et al., J. Mol. Biol. 291:1129-1134 (1999); Wirtz and Steipe, Protein Sci. 8:2245-2250 (1999); Zhu et al., J. Immunol. Methods 231:207-222 (1999); and references cited therein.

Recombinant expression of an antibody of the invention (including antibody fragments or variants thereof (e.g., a heavy or light chain of an antibody of the invention), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods, which are well known to those skilled in the art, can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is(are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants teherof (single chain antibodies), microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990); Bebbington et al., Bio/Techniques 10:169 (1992); Keen and Hale, Cytotechnology 18:207 (1996)). These references are incorporated in their entireties by reference herein.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors, which direct the expression of high levels of fusion protein products that are readily purified, may be desirable. Such vectors include, but are not limited to, the *E. coli* expression vector pUR278 (Ruther et al., EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include, but are not limited to, CHO, VERY, BHK, Hela, COS, NSO, MDCK, 293, 3T3, W138, and in particular, breast cancer cell lines such as, for example, BT483, Hs578T, HTB2, BT2O and T47D, and normal mammary gland cell line such as, for example, CRL7O3O and HsS78Bst.

For long-term, high-yield production of recombinant proteins, stable expression is preferred. For example, cell lines, which stably express the antibody, may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" in *DNA Cloning, Vol.*3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors is the availability of cell lines (e.g., the murine myeloma cell line, NS0) that are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657, which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169(1992) and in Biblia and Robinson *Biotechnol. Prog.* 11:1 (1995), which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers that enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310: 105-111). For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, 213Bi, or other radioisotopes such as, for example, iodine (131I, 125I, 123I, 121I), carbon (14C), sulfur (35S), tritium (3H), indium (115mIn, 113mIn, 112In, 111In), and technetium (99Tc, 99mTc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin.

In specific embodiments, antibodies of the invention may be labeled with Europium. For example, antibodies of the invention may be labelled with Europium using the DELFIA Eu-labeling kit (catalog#1244-302, Perkin Elmer Life Sciences, Boston, Mass.) following manufacturer's instructions.

In specific embodiments, antibodies of the invention are attached to macrocyclic chelators useful for conjugating radiometal ions, including but not limited to, 111In, 177Lu, 90Y, 166Ho, 153Sm, 215Bi and 225Ac to polypeptides. In a preferred embodiment, the radiometal ion associated with the macrocyclic chelators attached to antibodies of the invention is 111In. In another preferred embodiment, the radiometal ion associated with the macrocyclic chelator attached to antibodies polypeptides of the invention is 90Y. In specific embodiments, the macrocyclic chelator is 1,4,7,10-tetraazacyclododecane-N,N',N'',N'''-tetraacetic acid (DOTA). In specific embodiments, the macrocyclic chelator is α-(5-isothiocyanato-2-methoxyphenyl)-1,4,7,10-tetraaza-cyclododecane-1,4,7,10-tetraacetic acid. In other specific embodiments, the DOTA is attached to the antibody of the invention via a linker molecule. Examples of linker molecules useful for conjugatinga macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

In one embodiment, antibodies of the invention are labeled with biotin. In other related embodiments, biotinylated antibodies of the invention may be used, for example, as an imaging agent or as a means of identifying one or more TRAIL receptor coreceptor or ligand molecules.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire antibodies chemically modified at the N-terminus of either the heavy chain or the light chain or both. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the antibodies of the invention may be accomplished by any number of means. For example, polyethylene glycol may be attached to the antibody either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of antibodies without an intervening linker employs tresylated MPEG, which is produced by the modification of monmethoxy polyethylene glycol (MPEG) using tresylchloride (ClSO2CH2CF3). Upon reaction of protein with tresylated MPEG, polyethylene glycol is directly attached to amine groups of the protein. Thus, the invention includes antibody-polyethylene glycol conjugates produced by reacting antibodies of the invention with a polyethylene glycol molecule having a 2,2,2-trifluoreothane sulphonyl group.

Polyethylene glycol can also be attached to antibodies using a number of different intervening linkers. For example, U.S. Pat. No. 5,612,460, the entire disclosure of which is incorporated herein by reference, discloses urethane linkers for connecting polyethylene glycol to proteins. Antibody-polyethylene glycol conjugates wherein the polyethylene glycol is attached to the antibody by a linker can also be produced by reaction of antibodies with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated antibody products produced using the reaction chemistries set out herein are included within the scope of the invention.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., Crit. Rev. Thera. Drug Carrier Sys. 9:249-304 (1992).

Characterization of Anti-Neurokinin B Antibodies

Antibodies of the present invention (including molecules comprising, or alternatively consisting of, antibody fragments or variants thereof) may also be described or specified in terms of their binding to neurokinin B polypeptides or fragments or variants of neurokinin B polypeptides. In specific embodiments, antibodies of the invention bind neurokinin B polypeptides, or fragments or variants thereof, with a dissociation constant or $K_D$ of less than or equal to $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, or $10^{-5}$ M. More preferably, antibodies of the invention bind neurokinin B polypeptides or fragments or variants thereof with a dissociation constant or $K_D$ less than or equal to $5 \times 10^{-6}$ M, $10^{-6}$ M, $5 \times 10^{-7}$ M, $10^{-7}$ M, $5 \times 10^{-8}$ M, or $10^{-8}$ M. Even more preferably, antibodies of the invention bind neurokinin B polypeptides or fragments or variants thereof with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times^{-13}$ M, $10^{-13}$ M, $5 \times 10^{-14}$ M, $10^{-4}$ M, $5 \times 10^{-15}$ M, or $10^{-15}$ M. The invention encompasses antibodies that bind neurokinin B polypeptides with a dissociation constant or $K_D$ that is within any one of the ranges that are between each of the individual recited values.

In specific embodiments, antibodies of the invention bind neurokinin B polypeptides or fragments or variants thereof with an off rate ($k_{off}$) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. More preferably, antibodies of the invention bind neurokinin B polypeptides or fragments or variants thereof with an off rate ($k_{off}$) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$ $5 \times 10^{-6}$ sec$^{-1}$, $10^{-6}$ sec$^{-1}$, $5 \times 10^{-7}$ sec$^{-1}$ or $10^{-7}$ sec$^{-1}$. The invention encompasses antibodies that bind neurokinin B polypeptides with an off rate ($k_{off}$) that is within any one of the ranges that are between each of the individual recited values.

In other embodiments, antibodies of the invention bind neurokinin B polypeptides or fragments or variants thereof with an on rate ($k_{on}$) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. More preferably, antibodies of the invention bind neurokinin B polypeptides or fragments or variants thereof with an on rate ($k_{on}$) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$. The invention encompasses antibodies that bind neurokinin B polypeptides with on rate ($k_{on}$) that is within any one of the ranges that are between each of the individual recited values.

The antibodies of the invention (including molecules comprising, or alternatively consisting of, antibody fragments or variants thereof) specifically bind to a polypeptide or polypeptide fragment or variant of human neurokinin B (e.g., SEQ ID NO:2). In another embodiment, the antibodies of the invention specifically bind to a polypeptide or polypeptide fragment or variant of simian neurokinin B polypeptides. In yet another embodiment, the antibodies of the invention specifically bind to a polypeptide or polypeptide fragment or variant of murine neurokinin B polypeptides. In one embodiment, the antibodies of the invention bind specifically to human and simian neurokinin B polypeptides. In another embodiment, the antibodies of the invention bind specifically to human neurokinin B polypeptides and murine neurokinin B polypeptides. More preferably, antibodies of the invention, preferentially bind to human neurokinin B polypeptides compared to murine neurokinin B polypeptides.

In preferred embodiments, the antibodies of the present invention (including molecules comprising, or alternatively consisting of, antibody fragments or variants thereof), specifically bind to neurokinin B polypeptides and do not cross-react with any other antigens. In preferred embodiments, the antibodies of the invention specifically bind to neurokinin B polypeptides (e.g., SEQ ID NO:2 or fragments or variants thereof) and do not cross-react with one or more additional members of the tachykinin family (e.g., substance P, neurokinin A).

In another embodiment, the antibodies of the present invention (including molecules comprising, or alternatively consisting of, antibody fragments or variants thereof), specifically bind to neurokinin B polypeptides and cross-react with other antigens. In other embodiments, the antibodies of the invention specifically bind to neurokinin B polypeptides (e.g., SEQ ID NO:2, or fragments or variants thereof) and cross-react with one or more additional members of the tachykinin family (e.g., substance P, neurokinin A).

By way of non-limiting example, an antibody may be considered to bind a first antigen preferentially if it binds said first antigen with a dissociation constant ($K_D$) that is less than the antibody's $K_D$ for the second antigen. In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to neurokinin B polypeptides, the ability to inhibit neurokinin B mediated biological activity (e.g., the ability to inhibit neurokinin B-mediated vasoconstriction of blood vessels or the ability to inhibit neurokinin B-mediated intracellular calcium flux (see Example 3)); or the ability to substantially block binding of neurokinin B, or a fragment, variant or fusion protein thereof, to a neurokinin receptor (e.g., NK3R; GenBank ID:JQ1517, NK2R; GenBank ID:M57414, or NK1R; GenBank ID:M81797). Other biological activities that antibodies against neurokinin B polypeptides may have, include, but are not limited to, the ability to stimulate neurokinin B mediated biological activity (e.g., to stimulate neurokinin B-mediated vasoconstriction of blood vessels). Optionally, the antibodies of the invention will bind to the same epitope as at least one of the antibodies specifically referred to herein e.g., any one of the antibodies expressed by the cell lines referred to in Table 1. Such epitope binding can be routinely determined using assays known in the art.

The present invention also provides for antibodies (including molecules comprising, or alternatively consisting of, antibody fragments or variants thereof), that inhibit binding of a neurokinin B polypeptide ot a neurokinin receptor (e.g., NK3R, NK1R, NK2R). In one embodiment, an antibody that inhibits binding of neurokinin B polypeptides to a neurokinin receptor comprises, or alternatively consists of a VH and/or a VL domain of at least one of the scFvs referred to in Table 1, or fragment or variant thereof. In a specific embodiment, an antibody that inhibits binding of neurokinin B polypeptides to a neurokinin receptor comprises, or alternatively consists of, a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof), that inhibit one or more neurokinin B polypeptide mediated biological activities. In one embodiment, an antibody that inhibits one or more neurokinin B polypeptide mediated biological activities comprises, or alternatively consists of a VH and/or a VL domain of at least one of the scFvs referred to in Table 1, or fragment or variant thereof. In a specific embodiment, an antibody that inhibits one or more neurokinin B polypeptide mediated biological activities comprises, or alternatively consists of a VH and a VL domain of any one of the scFvs referred to in Table 1, or fragment or variant thereof. Nucleic acid molecules encoding these antibodies are also encompassed by the invention.

The present invention also provides for antibodies (including molecules comprising, or alternatively consisting of, antibody fragments or variants thereof) that inhibit neurokinin B-mediated vasoconstriction of blood vessels (e.g., hepatic portal vein, mesenteric vascular bed, and placental blood vessels). In one embodiment, an antibody that inhibits neurokinin B-mediated vasoconstriction of blood vessels comprises, or alternatively consists of a VH and/or a VL domain of at least one of the scFvs referred to in Table 1, or fragment or variant thereof. In a specific embodiment, an antibody that inhibits neurokinin B-mediated vasoconstriction of blood vessels comprises, or alternatively consists of a VH and a VL domain of any one of the scFvs referred to in Table 1, or fragment or variant thereof. Nucleic acid molecules encoding these antibodies. are also encompassed by the invention.

The present invention also provides for antibodies (including molecules comprising, or alternatively consisting of, antibody fragments or variants thereof), that stimulate neurokinin B-mediated vasoconstriction of blood vessels (e.g., hepatic portal vein, mesenteric vascular bed, and placental blood vessels). In one embodiment, an antibody that stimulates neurokinin B-mediated vasoconstriction of blood vessels comprises, or alternatively consists of a VH and/or a VL domain of at least one of the scFvs referred to in Table 1, or fragment or variant thereof. In a specific embodiment, an antibody that stimulates neurokinin B-mediated vasoconstriction of blood vessels comprises, or alternatively consists of a VH and a VL domain of any one of the scFvs referred to in Table 1, or fragment or variant thereof. Nucleic acid molecules encoding these antibodies are also encompassed by the invention.

Antibodies of the present invention (including antibody fragments or variants thereof) may be characterized in a variety of ways. In particular, antibodies and related molecules of the invention may be assayed for the ability to specifically bind to neurokinin B polypeptides or a fragment or variant of neurokinin B polypeptides using techniques described herein or routinely modifying techniques known in the art. Assays for the ability of the antibodies of the invention to specifically bind neurokinin B polypeptides or a fragment of neurokinin B polypeptides may be performed in solution (e.g., Houghten, Bio/Techniques 13:412-421(1992)), on beads (e.g., Lam, Nature 354:82-84 (1991)), on chips (e.g., Fodor, Nature 364: 555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249: 404-406 (1990); Cwirla et al., Proc. Natl. Acad. Sci. USA 87:7178-7182 (1990); and Felici, J. Mol. Biol. 222:301-310 (1991)) (each of these references is incorporated herein in its entirety by reference). Antibodies that have been identified to specifically bind to neurokinin B polypeptides or a fragment or variant of neurokinin B polypeptides can then be assayed for their specificity and affinity for neurokinin B polypeptides or a fragment or variant of a neurokinin B polypeptide using or routinely modifying techniques described herein or otherwise known in the art.

The antibodies of the invention may be assayed for specific binding to neurokinin B polypeptides and cross-reactivity with other antigens by any method known in the art. Immunoassays which can be used to analyze specific binding and cross-reactivity include, but are not limited to, competitive and non-competitive assay systems using techniques such as BIAcore analysis, FACS (fluorescence activated cell sorter) analysis, immunofluorescence, immunocytochemistry, radioimmunoassays, ELISA (enzyme linked immunosorbent assay), "sandwich" immunoassays, immunoprecipitation assays, western blots, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs, the antibody of interest does not have to be conjugated to a detectable compound; instead, a second antibody (which recognizes the antibody of interest) conjugated to a detectable compound may be added to the well. Alternatively, the antigen need not be directly coated to the well; instead the ELISA plates may be coated with an anti-Ig Fc antibody, and the antigen in the form of a neurokinin B-Fc fusion protein, may be bound to the anti-Ig Fc coated to the plate. This may be desirable so as to maintain the antigen protein (e.g., the neurokinin B polypeptides) in a more native conformation than it may have when it is directly coated to a plate. In another alternative, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., antigen labeled with $^3$H or $^{125}$I), or fragment or variant thereof with the antibody of interest in the presence of increasing amounts of unlabeled antigen, and the detection of the antibody bound to the labeled antigen. The affinity of the antibody of the present invention for neurokinin B and the binding off-rates can be determined from the data by Scatchard plot analysis. Competition with a second antibody can also be determined using radioimmunoassays. In this case, neurokinin B polypeptide is incubated with an antibody of the present invention conjugated to a labeled compound (e.g., compound labeled with $^3$H or $^{125}$I) in the presence of increasing amounts of an unlabeled second anti-neurokinin B antibody. This kind of competitive assay between two antibodies, may also be used to determine if two antibodies bind the same, closely associated (e.g., overlapping) or different epitopes.

In a preferred embodiment, BIAcore kinetic analysis is used to determine the binding on and off rates of antibodies (including antibody fragments or variants thereof) to neurokinin B, or fragments of neurokinin B. BIAcore kinetic analysis comprises analyzing the binding and dissociation of antibodies from chips with immobilized neurokinin B on their surface.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

Antibody Conjugates

The present invention encompasses antibodies (including antibody fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types (e.g., cancer cells), either in vitro or in vivo, by fusing or conjugating the heterologous polypeptides to antibodies of the invention that are specific for particular cell surface antigens or which bind antigens that bind particular cell surface receptors. Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention. Such fusion proteins may, for example, facilitate purification and may increase half-life in vivo. Antibodies fused or conjugated to heterologous polypeptides may also be used in in vitro immunoassays and purification methods using methods known in the art. See e.g., Harbor et al., supra, and PCT publication WO 93/2 1232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab)$_2$ fragment, or a portion thereof. Methods for fusing or conjugating polypeptides to antibody portions are known in the art. See, e.g., U.S. Pat. Nos. 5,356,603; 5,622,929; 5,359,046; 5,349,053; 5,447,851; 5,112,946; EP 307,434; EP 367,166; PCT publications WO 96/04388; WO 9 1/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11357- 11341 (1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830, 721; 5,834,252; and 5,837,458, and Patten et al., Curr. Opinion Biotechnol. 8:724-35 (1997); Harayama, Trends Biotechnol. 16(2):76-82 (1998); Hansson, et al., J. Mol. Biol. 287:

265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions specifically bind to neurokinin B may be recombined with one or more components, motifs, sections, parts, domains, fragments, etc. of one or more heterologous molecules.

Moreover, the antibodies of the present invention (including antibody fragments or variants thereof), can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the FLAG® tag (Stratagene, La Jolla, Calif.).

The present invention further encompasses antibodies (including antibody fragments or variants thereof), conjugated to a diagnostic or therapeutic agent. The antibodies can be used diagnostically to, for example, monitor or prognose the development or progression of a tumor as part of a clinical testing procedure to, e.g., determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions that can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin; and examples of suitable radioactive material include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$PM, $^{140}$La, 175Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody of the invention (including an scFv or other molecule comprising, or alternatively consisting of, antibody fragments or variants thereof), may be coupled or conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{135}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al., Nucl. Med. Biol. 26(8):943-50, 1999, which are hereby incorporated by reference in their entirety.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label antibodies of the invention. Such techniques include, but are not limited to, the use of bifunctional conjugating agents (see e.g., U.S. Pat. Nos. 5,756,065; 5,714,711; 5,696,239; 5,652,371; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention that are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/35899), Fas Ligand (Takahashi et al., *Int. Immunol.*, 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Antibodies of the invention (including antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an other molecules comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Uses of Antibodies of the Invention

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of neurokinin B polypeptides (e.g., the mature form of neurokinin B) in biological samples. See, e.g., Harlow et al., Antibodies: A Laboratory Manual, (Cold Spring Harbor Laboratory Press, 2nd ed. 1988) (incorporated by reference herein in its entirety).

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types, such as neurons. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

Epitope Mapping

The present invention provides antibodies (including antibody fragments or variants thereof) that can be used to identify epitopes of a neurokinin B polypeptide. In particular, the antibodies of the present invention can be used to identify epitopes of a human neurokinin B polypeptide (e.g., SEQ ID NO:2); a murine neurokinin B; a rat neurokinin B polypeptide; or a monkey neurokinin B polypeptide, using techniques described herein or otherwise known in the art. Fragments which function as epitopes may be produced by any conventional means. (See, e.g., Houghten, Proc. Natl. Acad. Sci. USA 82:5131-5135 (1985), further described in U.S. Pat. No. 4,711,211.) Identified epitopes of antibodies of the present invention may, for example, be used as vaccine candidates, i.e., to immunize an individual to elicit antibodies against the naturally occurring forms of neurokinin B polypeptides.

Diagnostic Uses of Antibodies

Labeled antibodies of the invention (including molecules comprising, or alternatively consisting of, antibody fragments or variants thereof) that specifically bind to a neurokinin B polypeptide can be used for diagnostic purposes to detect, diagnose, prognose, or monitor diseases and/or disorders. In specific embodiments, labeled antibodies of the invention (including molecules comprising, or alternatively consisting of, antibody fragments or variants thereof) that specifically bind to a neurokinin B polypeptide can be used for diagnostic purposes to detect, diagnose, prognose, or monitor diseases and/or disorders associated with the aberrant expression and/or activity of a neurokinin B polypeptide. In a specific embodiment, labeled antibodies of the invention that specifically bind to a neurokinin B polypeptide can be used for diagnostic purposes to detect, diagnose, prognose, or monitor pre-eclampsia.

The invention provides for the detection of expression of a neurokinin B polypeptide comprising: (a) assaying the expression of a neurokinin B polypeptide in a biological sample from an individual using one or more antibodies of the invention that specifically binds to a neurokinin B polypeptide; and (b) comparing the level of a neurokinin B polypeptide with a standard level of a neurokinin B polypeptide, (e.g., the level in normal biological samples).

The invention provides for the detection of aberrant expression of a neurokinin B polypeptide comprising: (a) assaying the expression of a neurokinin B polypeptide in a biological sample from an individual using one or more antibodies of the invention that specifically binds to a neurokinin B polypeptide; and (b) comparing the level of a neurokinin B polypeptide with a standard level of a neurokinin B polypeptide, e.g., in normal biological samples, whereby an increase or decrease in the assayed level of a neurokinin B polypeptide compared to the standard level of a neurokinin B polypeptide is indicative of aberrant expression.

By "biological sample" is intended any fluids and/or cells obtained from an individual, body fluid, body tissue, body cell, cell line, tissue culture, or other source which may contain a neurokinin B polypeptide protein or mRNA. Body fluids include, but are not limited to, sera, plasma, urine, synovial fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

One aspect of the invention is the detection and diagnosis of a disease or disorder associated with aberrant expression of a neurokinin B polypeptide or a neurokinin B polypeptide receptor (e.g., NK3R) in an animal, preferably a mammal and most preferably a human. In one embodiment, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that specifically binds to a neurokinin B polypeptide; b) waiting for a time interval following the administering for permitting the labeled antibody to preferentially concentrate at sites in the subject where neurokinin B polypeptide is expressed (and for unbound labeled molecule to be cleared to background level); c) determining background level; and d) detecting the labeled antibody in the subject, such that detection of labeled antibody or fragment thereof above the background level and above or below the level observed in a person without the disease or disorder indicates that the subject has a particular disease or disorder associated with aberrant expression of a neurokinin B polypeptide or a neurokinin B polypeptide receptor. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells that contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of the disease or disorder is carried out by repeating the method for diagnosing the disease or disorder, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

In specific embodiments, antibodies of the present invention may be used to detect elevated levels of neurokinin B during pregnancy. Excessive concentrations of neurokinin B were detected in plasma during pregnancy-induced hypertension and pre-eclampsia (Page et al. *Nature* 405:797-800 (2000)). Thus, elevated levels of neurokinin B in early pregnancy may be an indicator of pregnancy-induced hypertension and pre-eclampsia.

In specific embodiments, antibodies of the present invention may be used in the diagnosis, prevention, and treatment of hypertension, inflammation, asthma, gastrointestinal disorders, anxiety, depression, addiction, or pain particularly those diseases and/or disorders described in the "Therapeutic Uses of Antibodies" sections below.

Therapeutic Uses of Antibodies

One or more antibodies of the present invention (including molecules comprising, or alternatively consisting of, antibody fragments or variants thereof) that specifically bind to neurokinin B may be used locally or systemically in the body as a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for preventing or treating one or more of the disclosed diseases, disorders, or conditions. Therapeutic compounds of the invention include, but are not limited to, antibodies of the invention and nucleic acids encoding antibodies (and anti-idiotypic antibodies) of the invention as described herein. In one embodiment, the antibodies of the invention can be used to treat, ameliorate or prevent diseases, disorders or conditions, including, but not limited to, any one or more of the diseases, disorders, or conditions described herein. The treatment and/or prevention of diseases, disorders, or conditions includes, but is not limited to, alleviating symptoms associated with those diseases, disorders or conditions. Antibodies of the invention may be provided in pharmaceutically acceptable compositions as known in the art or as described herein.

Therapeutic Uses of Antibodies for Treating Vascular Disorders

In highly preferred embodiments, antibodies of the present invention are used to treat, prevent, and/or diagnose pre-eclampsia.

In highly preferred embodiments, antibodies of the present invention are used to treat, prevent, diagnose, and/or prognose hypertension.

In additional embodiments, antibodies of the present invention may be used to treat, prevent, diagnose, and/or prognose hypotension.

Other cardiovascular disorders that are treated, prevented, or diagnosed with antibodies of the present invention include, but are not limited to, heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Other cardiovascular disorders that are treated, prevented, or diagnosed with antibodies of the present invention include, but are not limited to, vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Other cardiovascular disorders that are treated, prevented, or diagnosed with antibodies of the present invention include, but are not limited to, carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Therapeutic Uses of Antibodies for Treating Inflammatory Disorders

In highly preferred embodiments, antibodies and antibody compositions of the invention are useful for treating, diagnosing, preventing, and/or detecting inflammatory diseases, such as irritable bowel syndrome and/or inflammatory bowel disease.

In highly preferred embodiments, antibodies and antibody compositions of the invention are useful for treating, diagnosing, preventing, and/or detecting allergy and/or asthma.

In other preferred embodiments, antibodies and antibody compositions of the invention are useful in the diagnosis and treatment or prevention of immune diseases and disorders including, but not limited to, inflammation associated with infection (e.g., septic shock, sepsis, or systemic inflammatory response syndrome), ischemia-reperfusion injury, endotoxin lethality, complement-mediated hyperacute rejection, nephritis, cytokine or chemokine induced lung injury, inflammatory bowel disease, Crohn's disease, over production of cytokines (e.g., TNF or IL-1.), respiratory disorders (e.g., asthma and allergy); gastrointestinal disorders (e.g., inflammatory bowel disease); cancers (e.g., gastric, ovarian, lung, bladder, liver, and breast); CNS disorders (e.g., multiple sclerosis; ischemic brain injury and/or stroke, traumatic brain injury, neurodegenerative disorders (e.g., Parkinson's disease and Alzheimer's disease); AIDS-related dementia; and prion disease); cardiovascular disorders (e.g., atherosclerosis, myocarditis, cardiovascular disease, and cardiopulmonary bypass complications); as well as many additional diseases, conditions, and disorders that are characterized by inflammation (e.g., hepatitis, rheumatoid arthritis, gout, trauma, pancreatitis, sarcoidosis, dermatitis, renal ischemia-reperfusion injury, Grave's disease, systemic lupus erythematosus, diabetes mellitus, and allogenic transplant rejection).

Because inflammation is a fundamental defense mechanism, inflammatory disorders can affect virtually any tissue of the body. Accordingly, antibodies of the invention have uses in the treatment of tissue-specific inflammatory disorders, including, but not limited to, adrenalitis, alveolitis, angiocholecystitis, appendicitis, balanitis, blepharitis, bronchitis, bursitis, carditis, cellulitis, cervicitis, cholecystitis, chorditis, cochlitis, colitis, conjunctivitis, cystitis, dermatitis, diverticulitis, encephalitis, endocarditis, esophagitis, eustachitis, fibrositis, folliculitis, gastritis, gastroenteritis, gingivitis, glossitis, hepatosplenitis, keratitis, labyrinthitis, laryngitis, lymphangitis, mastitis, media otitis, meningitis, metritis, mucitis, myocarditis, myositis, myringitis, nephritis, neuritis, orchitis, osteochondritis, otitis, pericarditis, peritendonitis, peritonitis, pharyngitis, phlebitis, poliomyelitis, prostatitis, pulpitis, retinitis, rhinitis, salpingitis, scleritis, sclerochoroiditis, scrotitis, sinusitis, spondylitis, steatitis, stomatitis, synovitis, syringitis, tendonitis, tonsillitis, urethritis, and vaginitis.

In another highly preferred embodiment, antibodies and antibody compositions of the invention are used as an adjuvant to enhance immune responsiveness to specific antigens, such as in anti-viral immune responses.

More generally, antibodies and antibody compositions of the invention are useful in regulating (i.e., elevating or reducing) immune response. For example, antibodies and antibody compositions of the invention may be useful in preparation or recovery from surgery, trauma, radiation therapy, chemotherapy, and transplantation, or may be used to boost immune response and/or recovery in the elderly and immunocompromised individuals. Alternatively, antibodies and antibody compositions of the invention are useful as immunosuppressive agents, for example in the treatment or prevention of autoimmune disorders. In specific embodiments, antibodies and antibody compositions of the invention are used to treat or prevent chronic inflammatory, allergic or autoimmune conditions, such as those described herein or are otherwise known in the art.

Therapeutic and Diagnostic Uses of Antibodies for Treating Gastrointestinal Disorders Antibodies of the present invention are used to treat, prevent, diagnose, and/or prognose gastrointestinal disorders, including inflammatory diseases (irritable bowel syndrome, inflammatory bowel disorder) and/or conditions, infections, cancers, and ulcers, such as peptic ulcers.

Other gastrointestinal disorders that are treated, prevented, or diagnosed with antibodies of the present invention include, but are not limited to, dysphagia, odynophagia, inflammation of the esophagus, peptic esophagitis, gastric reflux, submucosal fibrosis and stricturing, Mallory-Weiss lesions, leiomyomas, lipomas, epidermal cancers, adeoncarcinomas, gastric retention disorders, gastroenteritis, gastric atrophy, gastric/stomach cancers, polyps of the stomach, autoimmune disorders such as pernicious anemia, pyloric stenosis, gastritis (bacterial, viral, eosinophilic, stress-induced, chronic erosive, atrophic, plasma cell, and Ménétrier's), and peritoneal diseases (e.g., chyloperitoneum, hemoperitoneum, mesenteric cyst, mesenteric lymphadenitis, mesenteric vascular occlusion, panniculitis, neoplasms, peritonitis, pneumoperitoneum, and bubphrenic abscess).

Other gastrointestinal disorders that are treated, prevented, or diagnosed with antibodies of the present invention include, but are not limited to, disorders associated with the small intestine, such as malabsorption syndromes, distension, irritable bowel syndrome, sugar intolerance, celiac disease, duodenal ulcers, duodenitis, tropical sprue, Whipple's disease, intestinal lymphangiectasia, Crohn's disease, appendicitis, obstructions of the ileum, Meckel's diverticulum, multiple diverticula, failure of complete rotation of the small and large intestine, lymphoma, and bacterial and parasitic diseases (such as Traveler's diarrhea, typhoid and paratyphoid, cholera, infection by Roundworms (*Ascariasis lumbricoides*), Hookworms (*Ancylostoma duodenale*), Threadworms (*Enterobius vermicularis*), Tapeworms (*Taenia saginata, Echinococcus granulosus, Diphyllobothrium* spp., and *T. solium*).

Other gastrointestinal disorders that are treated, prevented, or diagnosed with antibodies of the present invention include, but are not limited to, liver diseases and/or disorders include intrahepatic cholestasis (alagille syndrome, biliary liver cirrhosis), fatty liver (alcoholic fatty liver, reye syndrome), hepatic vein thrombosis, hepatolentricular degeneration, hepatomegaly, hepatopulmonary syndrome, hepatorenal syndrome, portal hypertension (esophageal and gastric varices), liver abscess (amebic liver abscess), liver cirrhosis (alcoholic, biliary and experimental), alcoholic liver diseases (fatty liver, hepatitis, cirrhosis), parasitic (hepatic echinococcosis, fascioliasis, amebic liver abscess), jaundice (hemolytic, hepatocellular, and cholestatic), cholestasis, portal hypertension, liver enlargement, ascites, hepatitis (alcoholic hepatitis, animal hepatitis, chronic hepatitis (autoimmune, hepatitis B, hepatitis C, hepatitis D, drug induced), toxic hepatitis, viral human hepatitis (hepatitis A, hepatitis B, hepatitis C, hepatitis D, hepatitis E), Wilson's disease, granulomatous hepatitis, secondary biliary cirrhosis, hepatic encephalopathy, portal hypertension, varices, hepatic encephalopathy, primary biliary cirrhosis, primary sclerosing cholangitis, hepatocellular adenoma, hemangiomas, bile stones, liver failure (hepatic encephalopathy, acute liver failure), and liver neoplasms (angiomyolipoma, calcified liver metastases, cystic liver metastases, epithelial tumors, fibrolamellar hepatocarcinoma, focal nodular hyperplasia, hepatic adenoma, hepatobiliary cystadenoma, hepatoblastoma, hepatocellular carcinoma, hepatoma, liver cancer, liver hemangioendothelioma, mesenchymal hamartoma, mesenchymal tumors of liver, nodular regenerative hyperplasia, benign liver tumors (Hepatic cysts [Simple cysts, Polycystic liver disease, Hepatobiliary cystadenoma, Choledochal cyst], Mesenchymal tumors [Mesenchymal hamartoma, Infantile hemangioendothelioma, Hemangioma, Peliosis hepatis, Lipomas, Inflammatory pseudotumor, Miscellaneous], Epithelial tumors [Bile duct epithelium (Bile duct hamartoma, Bile duct adenoma), Hepatocyte (Adenoma, Focal nodular hyperplasia, Nodular regenerative hyperplasia)], malignant liver tumors [hepatocellular, hepatoblastoma, hepatocellular carcinoma, cholangiocellular, cholangiocarcinoma, cystadenocarcinoma, tumors of blood vessels, angiosarcoma, Karposi's sarcoma, hemangioendothelioma, other tumors, embryonal sarcoma, fibrosarcoma, leiomyosarcoma, rhabdomyosarcoma, carcinosarcoma, teratoma, carcinoid, squamous carcinoma, primary lymphoma]), peliosis hepatis, erythrohepatic porphyria, hepatic porphyria (acute intermittent porphyria, porphyria cutanea tarda), Zellweger syndrome).

Other gastrointestinal disorders that are treated, prevented, or diagnosed with antibodies of the present invention include, but are not limited to, pancreatic diseases and/or disorders include acute pancreatitis, chronic pancreatitis (acute necrotizing pancreatitis, alcoholic pancreatitis), neoplasms (adenocarcinoma of the pancreas, cystadenocarcinoma, insulinoma, gastrinoma, and glucagonoma, cystic neoplasms, islet-cell tumors, pancreoblastoma), and other pancreatic diseases (e.g., cystic fibrosis, cyst (pancreatic pseudocyst, pancreatic fistula, insufficiency)).

Other gastrointestinal disorders that are treated, prevented, or diagnosed with antibodies of the present invention include, but are not limited to, gallbladder diseases include gallstones (cholelithiasis and choledocholithiasis), postcholecystectomy syndrome, diverticulosis of the gallbladder, acute cholecystitis, chronic cholecystitis, bile duct tumors, and mucocele.

Other gastrointestinal disorders that are treated, prevented, or diagnosed with antibodies of the present invention include, but are not limited to, diseases and/or disorders of the large intestine include antibiotic-associated colitis, diverticulitis, ulcerative colitis, acquired megacolon, abscesses, fungal and bacterial infections, anorectal disorders (e.g., fissures, hemorrhoids), colonic diseases (colitis, colonic neoplasms [colon cancer, adenomatous colon polyps (e.g., villous adenoma), colon carcinoma, colorectal cancer], colonic diverticulitis, colonic diverticulosis, megacolon [Hirschsprung disease, toxic megacolon]; sigmoid diseases [proctocolitis, sigmoin neoplasms]), constipation, Crohn's disease, diarrhea (infantile diarrhea, dysentery), duodenal diseases (duodenal neoplasms, duodenal obstruction, duodenal ulcer, duodenitis), enteritis (enterocolitis), HIV enteropathy, ileal diseases (ileal neoplasms, ileitis), immunoproliferative small intestinal disease, inflammatory bowel disease (ulcerative colitis, Crohn's disease), intestinal atresia, parasitic diseases (anisakiasis, balantidiasis, blastocystis infections, cryptosporidiosis, dientamoebiasis, amebic dysentery, giardiasis), intestinal fistula (rectal fistula), intestinal neoplasms (cecal neoplasms, colonic neoplasms, duodenal neoplasms, ileal neoplasms, intestinal polyps, jejunal neoplasms, rectal neoplasms), intestinal obstruction (afferent loop syndrome, duodenal obstruction, impacted feces, intestinal pseudo-obstruction [cecal volvulus], intussusception), intestinal perforation, intestinal polyps (colonic polyps, gardner syndrome, peutz-jeghers syndrome), jejunal diseases (jejunal neoplasms), malabsorption syndromes (blind loop syndrome, celiac disease, lactose intolerance, short bowl syndrome, tropical sprue, whipple's disease), mesenteric vascular occlusion, pneumatosis cystoides intestinalis, protein-losing enteropathies (intestinal lymphagiectasis), rectal diseases (anus diseases, fecal incontinence, hemorrhoids, proctitis, rectal fistula, rectal prolapse, rectocele), peptic ulcer (duodenal ulcer, peptic esophagitis, hemorrhage, perforation, stomach ulcer, Zollinger-Ellison syndrome), postgastrectomy syndromes (dumping syndrome), stomach diseases (e.g., achlorhydria, duodenogastric reflux (bile reflux), gastric antral vascular ectasia, gastric fistula, gastric outlet obstruction, gastritis (atrophic or hypertrophic), gastroparesis, stomach dilatation, stomach diverticulum, stomach neoplasms (gastric cancer, gastric polyps, gastric adenocarcinoma, hyperplastic gastric polyp), stomach rupture, stomach ulcer, stomach volvulus), tuberculosis, visceroptosis, vomiting (e.g., hematemesis, hyperemesis gravidarum, postoperative nausea and vomiting) and hemorrhagic colitis.

Other gastrointestinal disorders that are treated, prevented, or diagnosed with antibodies of the present invention include, but are not limited to, biliary tract diseases, such as, gastroschisis, fistula (e.g., biliary fistula, esophageal fistula, gastric fistula, intestinal fistula, pancreatic fistula), neoplasms (e.g., biliary tract neoplasms, esophageal neoplasms, such as adenocarcinoma of the esophagus, esophageal squamous cell carcinoma, gastrointestinal neoplasms, pancreatic neoplasms, such as adenocarcinoma of the pancreas, mucinous cystic neoplasm of the pancreas, pancreatic cystic neoplasms, pancreatoblastoma, and peritoneal neoplasms), esophageal disease (e.g., bullous diseases, candidiasis, glycogenic acanthosis, ulceration, barrett esophagus varices, atresia, cyst, diverticulum (e.g., Zenker's diverticulum), fistula (e.g., tracheoesophageal fistula), motility disorders (e.g., CREST syndrome, deglutition disorders, achalasia, spasm, gastroesophageal reflux), neoplasms, perforation (e.g., Boerhaave syndrome, Mallory-Weiss syndrome), stenosis, esophagitis, diaphragmatic hernia (e.g., hiatal hernia); gastrointestinal diseases, such as, gastroenteritis (e.g., cholera morbus, norwalk virus infection), hemorrhage (e.g., hematemesis, melena, peptic ulcer hemorrhage), stomach neoplasms (gastric cancer, gastric polyps, gastric adenocarcinoma, stomach cancer)), hernia (e.g., congenital diaphragmatic hernia, femoral hernia, inguinal hernia, obturator hernia, umbilical hernia, ventral hernia), and intestinal diseases (e.g., cecal diseases (appendicitis, cecal neoplasms)).

Therapeutic Uses of Antibodies for Treating Neurological Disorders

In preferred embodiments antibodies and/or antibody compositions are used to treat, detect, diagnose, and/or ameliorate neurologic diseases such as pain, depression, anxiety, and addiction.

Additional neurologic disdorders that are treated, detected, diagnosed, and/or ameliorated with antibodies of the invention include hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Horner's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, ophthalmoplegia such as Duane's Syndrome, Horner's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, and Diabetic neuropathies such as diabetic foot.

Additional neurologic diseases that are treated or detected with antibodies of the present invention include cerebrovascular disorders (such as carotid artery diseases which include carotid artery thrombosis, carotid stenosis and Moyamoya Disease), cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache and migraine.

The antibodies and/or antibody compositions of the invention are also useful in the treatment or prevention of neurodegenerative disease states and/or behavioural disorders. Such neurodegenerative disease states and/or behavioral disorders include, but are not limited to, Alzheimer's Disease, Parkinson's Disease, Huntington's Disease, Tourette Syndrome, schizophrenia, mania, dementia, paranoia, obsessive compulsive disorder, panic disorder, learning disabilities, ALS, psychoses, autism, and altered behaviors, including disorders in feeding, sleep patterns, balance, and perception.

Additional Therapeutic Uses of Antibodies

The antibodies of the invention are used to diagnose, treat, ameliorate or prevent diseases, disorders or conditions associated with aberrant expression and/or activity of neurokinin B, including, but not limited to, any one or more of the diseases, disorders, or conditions described herein. The treatment and/or prevention of diseases, disorders, or conditions associated with aberrant neurokinin B expression and/or activity includes, but is not limited to, alleviating symptoms associated with those diseases, disorders or conditions. Antibodies of the invention may be provided in pharmaceutically acceptable compositions as known in the art or as described herein.

Antibodies of the present invention (including molecules comprising, or alternatively consisting of, antibody fragments or variants thereof) that function as agonists or antagonists of a neurokinin B, preferably of neurokinin B signal transduction, can be administered to an animal to diagnose, treat, prevent or ameliorate a disease or disorder associated aberrant neurokinin B expression, function, or aberrant neurokinin B receptor expression or function. For example, antibodies of the invention which mimic the action of neurokinin B binding to the neurokinin B receptor, in full or in part, (e.g., antibodies that act as neurokinin B agonists), may be administered to an animal to diagnose, treat, prevent or ameliorate a disease or disorder with associated aberrant neurokinin B expression and/or function or aberrant neurokinin B receptor expression and/or function. As an alternative example, antibodies of the invention which disrupt or prevent the interaction between neurokinin B and its receptor or inhibit, reduce, or prevent signal transduction through one or more neurokinin B receptors, may be administered to an animal to diagnose, treat, prevent or ameliorate a disease or disorder associated with associated aberrant neurokinin B expression and/or function or aberrant neurokinin B receptor expression and/or function. Antibodies of the invention which do not prevent neurokinin B from binding its ligand but inhibit or downregulate neurokinin B signal transduction can be administered to an animal to diagnose, treat, prevent or ameliorate a disease or disorder associated with aberrant neurokinin B expression, lack of neurokinin B function, aberrant neurokinin B receptor expression, or lack of neurokinin B receptor function. The ability of an antibody of the invention to enhance, inhibit, upregulate or downregulate neurokinin B signal transduction may be determined by techniques described herein or otherwise known in the art. For example, neurokinin B-induced receptor activation and the activation of signaling molecules can be determined by detecting the association of adaptor proteins with the neurokinin B receptors, by immunoprecipitation followed by western blot analysis (for example, as described herein).

Further, antibodies of the present invention (including molecules comprising, or alternatively consisting of, antibody fragments or variants thereof) which inhibit neurokinin B-mediated biological activities (e.g., neurokinin B-mediated vasoconstriction of blood vessels) can be administered to an animal to diagnose, treat, prevent or ameliorate a disease or disorder described herein, particularly pre-eclampsia, hypertension, and other vascular disorders. These antibodies may inhibit or abolish either all or a subset of the biological activities of neurokinin B, for example, by inducing a conformational change in neurokinin B. In a specific embodiment, an antibody of the present invention that decreases neurokinin B activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to neurokinin B activity in absence of the antibody is administered to an animal to diagnose, treat, prevent or ameliorate a disease or disorder. In another embodiment, a combination of antibodies, a combination of antibody fragments, a combination of antibody variants, or a combination of antibodies, antibody fragments and/or antibody variants that decrease neurokinin B activity by at least 95%, at least 90%, at least 85%, at least 80%, at least 75%, at least 70%, at least 65%, at least 60%, at least 55%, at least 50%, at least 45%, at least 40%, at least 45%, at least 35%, at least 30%, at least 25%, at least 20%, or at least 10% relative to neurokinin B activity in absence of the said antibodies or antibody fragments and/or antibody variants is administered to an animal to diagnose, treat, prevent or ameliorate a disease or disorder.

In a specific embodiment, an antibody of the present invention (including molecules comprising, or alternatively consisting of, antibody fragments or variants thereof) that stimulates or upregulates, in full or in part, neurokinin B activity (e.g., neurokinin B-mediated vasoconstriction of blood vessels) by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to neurokinin B activity in absence of the antibody is administered to an animal to diagnose, treat, prevent or ameliorate a disease or disorder associated with associated aberrant neurokinin B expression and/or function or aberrant neurokinin B receptor expression and/or function. In another embodiment, a combination of antibodies, a combination of antibody fragments, a combination of antibody variants, or a combination of antibodies, antibody fragments, and/or variants that stimulate or upregulate neurokinin B activity by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99%, at least two-fold, at least three-fold, at least four fold, at least five fold, at least ten-fold, at least twenty-fold, at least fifty-fold, or at least one hundred-fold relative to neurokinin B activity in absence of said antibodies, antibody fragments, and/or antibody variants are administered to an animal to diagnose, treat, prevent or ameliorate a disease or disorder associated with associated aberrant neurokinin B expression and/or finction or aberrant neurokinin B receptor expression and/or function.

Suitable agents, which also block binding of neurokinin B to a neurokinin B receptor (e.g., NK3R) that may be administered with the antibodies of the present invention include, but are not limited to, soluble neurokinin B receptor polypeptides; multimeric forms of soluble neurokinin B receptor polypeptides; anti-neurokinin B antibodies that bind the neurokinin B without transducing the biological signal that results in vasoconstrction; anti-neurokinin B antibodies that block binding of neurokinin B to one or more neurokinin B receptors; and muteins of neurokinin B that bind neurokinin B receptors but do not transduce the biological signal that results in vasoconstriction.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer an antibody of the invention or a fragment or variant thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1535 (1990); Treat et al., in Liposomes in the Therapy of Infectious Disease and Cancer, Lopez-Berestein and Fidler (eds.), Liss, New York, pp. 353- 365 (1989); Lopez-Berestein, ibid., pp. 3 17-327; see generally ibid.).

In yet another embodiment, the composition can be delivered in a controlled release system. In one embodiment, a pump may be used (see Langer, supra; Sefton, CRC Crit. Ref. Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:71 (1983); see also Levy et al., Science 228: 190 (1985); During et al., Ann. Neurol. 25:35 1 (1989); Howard et al., J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1535 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent in vivo inhibiting and/or neutralizing antibodies of the invention (including molecules comprising, or alternatively consisting of, antibody fragments or variants thereof) that specifically bind to neurokinin B polypeptides, or polynucleotides encoding antibodies that specifically bind to neurokinin B polypeptides, for both immunoassays and therapy of disorders related to neurokinin B polynucleotides or polypeptides, including fragments thereof. Such antibodies will preferably have an affinity for neurokinin B polypeptides and/or neurokinin B polypeptide fragments. Preferred binding affinities include those with a dissociation constant or $K_D$ of less than or equal to $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, or $10^{-5}$ M. More preferably, antibodies of the invention bind neurokinin B polypeptides or fragments or variants thereof with a dissociation constant or $K_D$ less than or equal to $5 \times 10^{-6}$ M, $10^{-6}$ M, $5 \times 10^{-7}$ M, $10^{-7}$ M, $5 \times 10^{-8}$ M, or $10^{-8}$ M. Even more preferably, antibodies of the invention bind neurokinin B polypeptides or fragments or variants thereof with a dissociation constant or $K_D$ less than or equal to $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In a preferred embodiment, antibodies of the invention inhibit vasoconstriction of blood vessels (e.g., hepatic portal vein, mesenteric vascular bed). In an additional preferred embodiment, antibodies of the invention induce vasoconstriction of blood vessels (e.g., hepatic portal vein, mesenteric vascular bed).

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibody and antibody compositions of the invention may be administered alone or in combination with other therapeutic agents, including but not limited to chemotherapeutic agents, antibiotics, antivirals, anti-retroviral agents, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Combination Therapies with Anti-Neurokinin B Antibodies, Immunomodulatory Agents, Neurokinin B, and/or Anti-Hypertensives Anti-neurokinin B antibodies may be administered in combination with other anti-neurokinin B antibodies, immunomodulatory agents, neurokinin B, and/or anti-hypertensives.

In specific embodiments, an antibody of the invention that specifically binds neurokinin B is used or administered in combination with a second antibody that specifically binds neurokinin B. In another embodiment, the antibodies specific for neurokinin B are antagonistic antibodies that inhibit neurokinin B-mediated vasoconstriction of blood vessels. In a specific embodiment, the combination of anti-neurokinin B treatment inhibits more vasoconstriction of blood vessels than either anti-neurokinin B antibody treatment alone. In additional embodiments, anti-neurokinin B antibodies are administered with agents that block the function of other tachykinins such as neutralizing anti-SP, anti-NKA, antagonistic NK1R, and/or antagonistic NK2R antibodies or soluble forms of NK1R, NK2R, and/or NK3R. The anti-neurokinin B antibodies and/or agents that block the function of other tachykinins may be administered either simultaneously, sequentially, or a combination of simultaneous or sequential administration throughout the dosage regimen.

In another specific embodiment anti-neurokinin B antibodies are used or administered in combination with an anti-hypertensive, antipsychotic, immunomodulatory, and/or treatment for gastrointestinal disorders. In a particular embodiment, the inhibition and/or stimulation of vasoconstriction of blood vessels resulting from anti-neurokinin B antibody treatment, is more evident or more pronounced when the anti-neurokinin B antibodies are used or administered in combination with an anti-hypertensive, antipsychotic, immunomodulatory agent, treatment for gastrointestinal disorder, and/or a cross-linking reagent.

In a highly preferred embodiment, compositions of the invention are administered in combination with an anti-hypertensive agent. Anti-hypertensive agents that may be administered with the compositions of the invention include, but are not limited to diuretic agents, such as carbonic anhydrase-inhibiting agents (e.g., acetazolamide, dichlorphenamide, and methazolamide), osmotic diuretics (e.g., glycerin, isosorbide, mannitol, and urea), diuretics that inhibit $Na^+$—$K^+$-$2Cl^-$ symport (e.g., furosemide, bumetanide, azosemide, piretanide, tripamide, ethacrynic acid, muzolimine, and torsemide), thiazide and thiazide-like diuretics (e.g., bendroflumethiazide, benzthiazide, chlorothiazide, hydrochlorothiazide, hydroflumethiazide, methyclothiazide, polythiazide, trichormethiazide, chlorthalidone, indapamide, metolazone, and quinethazone), potassium sparing diuretics (e.g., amiloride and triamterene), mineralcorticoid receptor antagonists (e.g., spironolactone, canrenone, and potassium canrenoate), adrenergic blockers (e.g., acebutolol, atenolol, betaxolol, bisoprolol, carteolol, labetalol, metoprolol, nadolol, oxprenolol, penbutolol, pindolol, propranolol, sotalol, and timolol), angiotensin Converting Enzyme (ACE) inhibitors (e.g., papaverine, isoxsuprine, benazepril, captopril, cilazapril, enalapril, enalaprilat, fosinopril, lisinopril, moexipril, perindopril, quinapril, ramipril, spirapril, trandolapril, and nylidrin), nitrates (e.g., isosorbide dinitrate, isosorbide mononitrate, and nitroglycerin), and calcium channel blocking agents (e.g., amlodipine, bepridil, diltiazem, felodipine, flunarizine, isradipine, nicardipine, nifedipine, nimodipine, and verapamil).

In an additional embodiment, the antibody and antibody compositions of the invention are administered alone or in combination with an anti-inflammatory agent. Anti-inflammatory agents that may be administered with the antibody and antibody compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In certain embodiments, the antibodies of the present invention are administered in combination with agents used to treat psychiatric disorders. Psychiatric drugs that may be administered include, but are not limited to, antipsychotic agents (e.g., chlorpromazine, chlorprothixene, clozapine, fluphenazine, haloperidol, loxapine, mesoridazine, molindone, olanzapine, perphenazine, pimozide, quetiapine, risperidone, thioridazine, thiothixene, trifluoperazine, and triflupromazine), antimanic agents (e.g., carbamazepine, divalproex sodium, lithium carbonate, and lithium citrate), antidepressants (e.g., amitriptyline, amoxapine, bupropion, citalopram, clomipramine, desipramine, doxepin, fluvoxamine, fluoxetine, imipramine, isocarboxazid, maprotiline, mirtazapine, nefazodone, nortriptyline, paroxetine, phenelzine, protriptyline, sertraline, tranylcypromine, trazodone, trimipramine, and venlafaxine), antianxiety agents (e.g., alprazolam, buspirone, chlordiazepoxide, clorazepate, diazepam, halazepam, lorazepam, oxazepam, and prazepam), stimulants (e.g., d-amphetamine, methylphenidate, and pemoline), antiepileptic agents (e.g., carbamazepine, clonazepam, ethosuximide, phenobarbital, phenytoin, primidone, valproic acid, divalproex sodium, felbamate, gabapentin, lamotrigine, levetiracetam, oxcarbazepine, tiagabine, topiramate, zonisamide, diazepam, lorazepam, and clonazepam), antiparkinsonian agents (e.g., levodopa/carbidopa, selegiline, amantidine, bromocriptine, pergolide, ropinirole, pramipexole, benztropine; biperiden; ethopropazine; procyclidine; trihexyphenidyl, tolcapone), and ALS therapeutics (e.g., riluzole).

In certain embodiments, the antibodies of the invention are administered in combination with treatments for gastrointestinal disorders. Treatments for gastrointestinal disorders that may be administered include, but are not limited to, $H_2$ histamine receptor antagonists (e.g., TAGAMET™ (cimetidine), ZANTAC™ (ranitidine), PEPCID™ (famotidine), and AXID™ (nizatidine)); inhibitors of $H^+$, $K^+$ ATPase (e.g., PREVACID™ (lansoprazole) and PRILOSEC™ (omeprazole)); Bismuth compounds (e.g., PEPTO-BISMOL™ (bismuth subsalicylate) and DE-NOL™ (bismuth subcitrate)); various antacids; sucralfate; prostaglandin analogs (e.g., CYTOTEC™ (misoprostol)); muscarinic cholinergic antagonists; laxatives (e.g., surfactant laxatives, stimulant laxatives, saline and osmotic laxatives); antidiarrheal agents (e.g., LOMOTIL™ (diphenoxylate), MOTOFEN™ (diphenoxin), and IMODIUM™ (loperamide hydrochloride)), synthetic analogs of somatostatin such as SANDOSTATIN™ (octreotide), antiemetic agents (e.g., ZOFRAN™ (ondansetron), KYTRIL™ (granisetron hydrochloride), tropisetron, dolasetron, metoclopramide, chlorpromazine, perphenazine, prochlorperazine, promethazine, thiethylperazine, triflupromazine, domperidone, haloperidol, droperidol, trimethobenzamide, dexamethasone, methylprednisolone, dronabinol, and nabilone); D2 antagonists (e.g., metoclopramide, trimethobenzamide and chlorpromazine); bile salts; chenodeoxycholic acid; ursodeoxycholic acid; and pancreatic enzyme preparations such as pancreatin and pancrelipase.

In specific embodiments, an antibody of the invention that specifically binds neurokinin B is used or administered in combination with a second antibody that specifically binds neurokinin B. In another embodiment, the antibodies specific for neurokinin B are agonistic antibodies that stimulate neurokinin B-mediated vasoconstriction of blood vessels. In a specific embodiment, the combination of anti-neurokinin B treatment stimulates more vasoconstriction of blood vessels than either anti-neurokinin B antibody treatment alone.

In additional embodiments, anti-neurokinin B antibodies of the present invention may be administered in combination with a soluble form of other tachykinins which include, but are not limited to, neurokinin A and/or substance P.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans.

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

Antibodies or compositions of the invention can be tested for their ability to reduce vasoconstriction of blood vessels in in vitro, ex vivo and in vivo assays. Antibodies or compositions of the invention can also be tested for their ability to inhibit inflammation in in vitro and in vivo assays. Antibodies or compositions of the invention can also be tested for their ability to alleviate of one or more symptoms associated with pre-eclampsia, an inflamatory disorder, a neurological disorder or a gastrointestinal disease. Antibodies or compositions of the invention can also be tested for their ability to decrease the time course of an inflammatory disease. Further, antibodies or compositions of the invention can be tested for their ability to increase the survival period of animals suffering from disease or disorder, including pre-eclampsia, an inflammatory disorder, a neurological disorder or a gastrointestinal disease. Techniques known to those of skill in the art can be used to analyze the function of the antibodies or compositions of the invention in vivo.

Efficacy in treating or preventing hypertension may be demonstrated by detecting the ability of an antibody or composition of the invention to inhibit the vasoconstriction of blood vessels, to inhibit an increase in blood pressure, or to prevent, ameliorate or alleviate the symptoms of disease progression. The treatment is considered therapeutic if there is, for example, a reduction in blood pressure, amelioration of one or more symptoms, or a decrease in mortality and/or morbidity following administration of an antibody or composition of the invention.

Antibodies or compositions of the invention can be tested for their ability to modulate the biological activity of immune cells by contacting immune cells, preferably human immune cells (e.g., T cells, B-cells, and Natural Killer cells), with an antibody or composition of the invention or a control compound and determining the ability of the antibody or composition of the invention to modulate (i.e., increase or decrease) the biological activity of immune cells. The ability of an antibody or composition of the invention to modulate the biological activity of immune cells can be assessed by detecting the expression of antigens, detecting the proliferation of immune cells (i.e., T-cell proliferation), detecting the activation of signaling molecules, detecting the effector function of immune cells, or detecting the differentiation of immune cells. Techniques known to those of skill in the art can be used for measuring these activities. In specific embodiments, the ability of an antibody or composition of the invention to modulate the biological activity of immune cells can be assessed by detecting the localization or migration of immune cells. For example, cellular proliferation can be assayed by $^3$H-thymidine incorporation assays and trypan blue cell counts. Antigen expression can be assayed, for example, by immunoassays including, but not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Panels/Mixtures

The present invention also provides for mixtures of antibodies (including scFvs and other molecules comprising, or alternatively consisting of, antibody fragments or variants thereof) that specifically bind to neurokinin B or a fragment or variant thereof, wherein the mixture has at least one, two, three, four, five or more different antibodies of the invention. In specific embodiments, the invention provides mixtures of at least 2, preferably at least 4, at least 6, at least 8, at least 10, at least 12, at least 15, at least 20, or at least 25 different antibodies that specifically bind to neurokinin B or fragments or variants thereof, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that specifically bind to neurokinin B or a fragment or variant thereof, wherein the panel has at least one, two, three, four, five or more different antibodies of the invention. In specific embodiments, the invention provides for panels of antibodies that have different affinities for neurokinin B, different specificities for neurokinin B, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000 antibodies. Panels of antibodies can be used, for example, in 96 well plates for assays such as ELISAs.

The present invention further provides for compositions comprising, one or more antibodies (including molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains of a one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s of a VH domain of one or more of the scFvs referred to in Table 1, or a variant thereof. In another embodiment, a composition of the present invention comprises, one, two, three, four, five or more antibodies that comprise, or alternatively consist of, a polypeptide having an amino acid sequence of any one or more of the VH CDR2s of a VH domain of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s as of a VH domain of one or more of the scFvs referred to in Table 1, or a variant thereof.

Other embodiments of the present invention providing for compositions comprising, one or more antibodies (including molecules comprising, or alternatively consisting of antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s domains of one or more of the scFvs referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s of one or more of the scFvs referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s domains of one or more of the scFvs referred to in Table 1, or a variant thereof.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alterative embodiment, a kit comprises an antibody fragment that specifically binds to neurokinin B polypeptides or fragments or variants thereof. In a specific embodiment, the kits of the present invention contain a substantially isolated neurokinin B polypeptide or fragment or variant thereof as a control. Preferably, the kits of the present invention further comprise a control antibody that does not react with any, some or all neurokinin B. In another specific embodiment, the kits of the present invention contain a means for detecting the binding of an antibody to neurokinin B polypeptides (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized neurokinin B. The neurokinin B provided in the kit may also be attached to a solid support. In a more specific embodiment the detecting means of the above-described kit includes a solid support to which neurokinin B is attached. Such a kit may also include a non-attached reporter-labeled anti-human antibody. In this embodiment, binding of the antibody to neurokinin B can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with neurokinin B, and means for detecting the binding of neurokinin B polypeptides to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having surface-bound neurokinin B obtained by the methods of the present invention. After neurokinin B polypeptides bind to a specific antibody, the unbound serum components are removed by washing, reporter-labeled anti-human antibody is added, unbound anti-human antibody is removed by washing, and a reagent is reacted with reporter-labeled anti-human antibody to bind reporter to the reagent in proportion to the amount of bound anti-neurokinin B antibody on the solid support. Typically, the reporter is an enzyme that is detected by incubating the solid phase in the presence of a suitable fluorometric, luminescent or colorimetric substrate.

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant neurokinin B, and a reporter-labeled anti-human antibody for detecting surface-bound anti-neurokinin B antibody.

Gene Therapy

In a specific embodiment, nucleic acids comprising sequences encoding antibodies or functional derivatives thereof, are administered to diagnose, treat, inhibit or prevent a disease or disorder associated with aberrant expression and/or activity of neurokinin B and/or its receptors (e.g., NK3R), by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 1 1(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06 180; WO 92/22715; W092/203 16; W093/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651(1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication W094/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma. Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Having generally described the invention, the same will be more readily understood by reference to the following examples, which are provided by way of illustration and are not intended as limiting.

EXAMPLES

Example 1

Generation of Anti-neurokinin B Antibodies

General Methods

Rescue of the Library.

A library of scFvs is constructed from the RNA of human PBLs as described in WO92/01047 (which is hereby incorporated by reference in its entirety). To rescue phage displaying antibody fragments, approximately 109 *E. coli* harboring the phagemid are used to inoculate 50 ml of 2×TY containing 1% glucose and 100 micrograms/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see WO92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 micrograms/ml ampicillin and 50 micrograms/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells were spun down (IEC-Centra 8, 4000 revs/min for 10 min), resuspended in 300 ml 2×TY broth containing 100 micrograms ampicillin/ml and 25 micrograms kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 micrometer filter (Minisart NML; Sartorius) to give a final concentration of approximately $10^{13}$ transducing units/ml (ampicillin-resistant clones).

Panning the Library.

Immunotubes (Nunc) are coated overnight in PBS with 4 ml of either 100 micrograms/ml or 10 micrograms/ml of a TR2 receptor polypeptide. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 micrograms/ml ampicillin. The resulting bacterial library is then rescued with delta gene 3 helper phage as described above to prepare phage for a subsequent round of selection. This process is usually repeated for a total of 2-4 rounds of affinity purification.

Characterization of Binders.

Eluted phage from the final rounds of selection are used to infect *E. coli* HB 2151 and soluble scFv is produced (Marks, et al., 1991) from single colonies for assay. ELISAs are performed with microtiter plates coated with either 10 picograms/ml of the polypeptide of the present invention in 50 mM bicarbonate pH 9.6. Clones positive in ELISA are further characterized by PCR fingerprinting (see e.g., WO92/01047) and then by sequencing.

Example 2

Identification and Cloning of VH and VL Domains

One method to identify and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the cell lines. Cells may lysed in the TRIzol® reagent (Life Technologies, Rockville. Md.) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Following washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can be determined using optical density measurements.

cDNA may be synthesized, according to methods well-known in the art, from 1.5-2.5 micrograms of RNA using reverse transcriptase and random hexamer primers. cDNA is then used as a template for PCR amplification of VH and VL domains. Alternatively, DNA encoding an scFv, e.g., a vector containing the scFv expression construct, may be used as template material for the following PCR reaction. Primers used to amplify VH and VL genes are shown in Table 3. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1× PCR buffer, 2 mM of each dNTP, 0.7 units of High Fidelity Taq polymerase, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 3

Primer Sequences Used to Amplify VH and VL domains.

| Primer name | SEQ ID NO | Primer Sequence (5'-3') |
|---|---|---|
| VH Primers | | |
| Hu VH1-5' | 41 | CAGGTGCAGCTGGTGCAGTCTGG |
| Hu VH2-5' | 42 | CAGGTCAACTTAAGGGAGTCTGG |
| Hu VH3-5' | 43 | GAGGTGCAGCTGGTGGAGTCTGG |
| Hu VH4-5' | 44 | CAGGTGCAGCTGGAGGAGTCGGG |
| Hu VH5-5' | 45 | GAGGTGCAGCTGTTGCAGTCTGC |
| Hu VH6-5' | 46 | CAGGTACAGCTGCAGCAGTCAGG |
| Hu JH1,2-5' | 47 | TGAGGAGACGGTGACCAGGGTGCC |
| Hu JH3-5' | 48 | TGAAGAGACGGTGACCATTGTCCC |
| Hu JH4,5-5' | 49 | TGAGGAGACGGTGACCAGGGTTCC |
| Hu JH6-5' | 50 | TGAGGAGACGGTGACCGTGGTCCC |
| VL Primers | | |
| Hu Vkappa1-5' | 51 | GACATCCAGATGACCCAGTCTCC |
| Hu Vkappa2a-5' | 52 | GATGTTGTGATGACTCAGTCTCC |
| Hu Vkappa2b-5' | 53 | GATATTGTGATGACTCAGTCTCC |
| Hu Vkappa3-5' | 54 | GAAATTGTGTTGACGGAGTCTCC |
| Hu Vkappa4-5' | 55 | GACATCGTGATGACCCAGTCTCC |
| Hu Vkappa5-5' | 56 | GAAACGACACTCACGCAGTCTCC |
| Hu Vkappa6-5' | 57 | GAAATTGTGCTGACTCAGTCTCC |
| Hu Vlambda1-5' | 58 | CAGTCTGTGTTGACGCAGCCGCC |
| Hu Vlambda2-5' | 59 | CAGTCTGCCCTGACTCAGCCTGC |
| Hu Vlambda3-5' | 60 | TCCTATGTGCTGACTCAGCCACC |
| Hu Vlambda3b-5' | 61 | TCTTGTGAGCTGACTCAGGACCC |
| Hu Vlambda4-5' | 62 | CACGTTATACTGACTCAACCGCC |
| Hu Vlambda5-5' | 63 | CAGGCTGTGCTCACTCAGCCGTC |
| Hu Vlambda6-5' | 64 | AATTTTATGCTGACTCAGCCCCA |
| Hu Jkappa1-3' | 65 | ACGTTTGATTTCCACCTTGGTCCC |
| Hu Jkappa2-3' | 66 | ACGTTTGATCTCCAGCTTGGTCCC |
| Hu Jkappa3-3' | 67 | ACGTTTGATATCCACTTTGGTCCC |
| Hu Jkappa4-3' | 68 | ACGTTTGATCTCCACCTTGGTCCC |
| Hu Jkappa5-3' | 69 | ACGTTAATCTCCAGTCGTGTCCC |
| Hu Jlambda1-3' | 70 | CAGTCTGTGTTGACGCAGCCGCC |
| Hu Jlambda2-3' | 71 | CAGTCTGCCGTGACTCAGCCTGC |
| Hu Jlambda3--3' | 72 | TCCTATGTGCTGACTCAGCCACC |
| Hu Jlambda3b-3' | 73 | TCTTCTGAGCTGACTCAGGACCC |
| Hu Jlambda4-3' | 74 | CACGTTATACTGACTCAACCGCC |
| Hu Jlambda5-3' | 75 | CAGGCTGTGCTCACTCAGCGGTC |
| Hu Jlambda6-3' | 76 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of *E. coli* and blue/white color selection. Cloned PCR products may then be sequenced using methods commonly known in the art.

Example 3

Detecting Inhibition of Intracellular Calcium Flux Using Anti-Neurokinin B Antibodies General Methods Binding of Neurokinin B to its receptor (e.g., NK3R), may alter intracellular levels of calcium. These alterations can be measured in an assay using Fluorometric Imaging Plate Reader ("FLIPR"; Molecular Probes) to measure changes in fluorescent molecules that bind small molecules. Clearly, any fluorescent molecule detecting a small molecule can be used instead of the calcium fluorescent molecule, fluo-4 (Molecular Probes, Inc.; catalog no. F-14202), used here.

For adherent cells transfected with a Neurokinin B receptor, seed the cells at $1-2 \times 10^5$ cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid in DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells transfected with a Neurokinin B receptor, the cells are spun down from culture media. Cells are re-suspended to $2-5 \times 10^6$ cells/ml with HBSS in a 50-ml conical tube. Four microliters of 1 mg/ml fluo-4 solution in 10% pluronic acid DMSO is added to each ml of cell suspension. The tube is then placed in a 37 degrees C. water bath for 30-60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley Cell Wash with 200 ul of HBSS, followed by an aspiration step to 100 ul final volume.

To measure the fluorescence of intracellular calcium, the FLIPR is set for the following parameters: (1) System gain is 300-800 mW; (2) Exposure time is 0.4 second; (3) Camera F/stop is F/2; (4) Excitation is 488 nm; and (5) Emission is 530 nm. The first sample addition consists of 4 ul of Buffer only or a solution of Buffer and anti-Neurokinin B. The second addition consists of 6 ul of Neurokinin B. Appropriate concentrations of Neurokinin B and Neurokinin B antisera can be determined by one of ordinary skill in the art. Increased emission at 530 nm indicates an extracellular signaling event caused by Neurokinin B or a molecule induced by Neurokinin B, which has resulted in an increase in the intracellular $Ca^{++}$ concentration.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety.

The entire disclosures (including the specification, sequence listing, and drawings) of International Application No. PCT/US03/16802 filed May 29, 2003 and of U.S. Provisional Application No. 60/383,802 filed May 30, 2002 are herein incorporated by reference in their entireties.

What is claimed is:

1. An isolated antibody or fragment thereof comprising the amino acid sequence of the VH and VL domains of SEQ ID NO:22, wherein said antibody or fragment thereof specifically binds neurokinin B.

2. The antibody or fragment thereof of claim 1 that binds neurokinin B purified from a cell culture wherein said neurokinin B is encoded by a polynucleotide encoding amino acids 1 to 121 of SEQ ID NO:2.

3. An isolated antibody or fragment thereof comprising the amino acid sequence of the VHCDR1, VHCDR2, VHCDR3, VLCDR1, VLCDR2, and VLCDR3 of the scFv of SEQ ID NO:22, wherein said antibody or fragment thereof specifically binds neurokinin B.

4. The antibody or fragment thereof of claim 3 wherein the antibody or fragment thereof is a whole immunoglobulin molecule, an scFv, a Fab fragment, a Fab' fragment, a F(ab')2, an Fv, or a disulfide linked Fv.

5. The antibody or fragment thereof of claim 3 wherein the antibody or fragment thereof is monoclonal, human, chimeric, or humanized.

6. The antibody or fragment thereof of claim 3 which comprises a heavy chain immunoglobulin constant domain selected from the group consisting of:
    (a) a human IgM constant domain;
    (b) a human IgG1 constant domain;
    (c) a human IgG2 constant domain;
    (d) a human IgG3 constant domain;
    (e) a human IgG4 constant domain; and
    (f) a human IgA constant domain.

7. The antibody or fragment thereof of claim 3 which comprises a light chain immunoglobulin constant domain selected from the group consisting of:
    (a) a human Ig kappa constant domain; and
    (b) a human Ig lambda constant domain.

8. The antibody or fragment thereof of claim 3 wherein the antibody or fragment thereof has a dissociation constant ($K_D$) of less than or equal to $10^{-9}$M.

9. The antibody or fragment thereof of claim 3 wherein the antibody or fragment thereof is conjugated to a detectable label.

10. The antibody or fragment thereof of claim 9, wherein the detectable label is a radiolabel.

11. The antibody or fragment thereof of claim 10, wherein the radiolabel is $^{125}$I, $^{131}$I, $^{111}$In, $^{90}$Y, $^{99}$Tc, $^{177}$Lu, $^{166}$Ho, or $^{153}$Sm.

12. The antibody or fragment thereof of claim 9, wherein the detectable label is an enzyme, a fluorescent label, a luminescent label, or a bioluminescent label.

13. The antibody or fragment thereof of claim 3 wherein the antibody or fragment thereof is biotinylated.

14. The antibody or fragment thereof of claim 3 wherein the antibody or fragment thereof is conjugated to a therapeutic or cytotoxic agent.

15. The antibody or fragment thereof of claim 14, wherein the therapeutic or cytotoxic agent is an anti-metabolite, an alkylating agent, an antibiotic, a growth factor, a cytokine, an antiangiogenic agent, an anti-mitotic agent, an anthracycline, a toxin, or an apoptotic agent.

16. The antibody or fragment thereof of claim 3 wherein the antibody or fragment thereof is attached to a solid support.

17. The antibody or fragment thereof of claim 3 wherein the antibody or fragment thereof specifically binds neurokinin B in a Western blot.

18. The antibody or fragment thereof of claim 3 wherein the antibody or fragment thereof specifically binds neurokinin B in an ELISA.

19. The antibody or fragment thereof of claim 3 wherein the antibody or fragment thereof inhibits the activity of neurokinin B or a fragment thereof.

20. The antibody or fragment thereof of claim 19 wherein the antibody or fragment thereof diminishes or abolishes the ability of neurokinin B or a fragment thereof to bind to its receptor.

21. The antibody or fragment thereof of claim 20, wherein said receptor is NK3R, NK1R, or NK2R.

22. The antibody or fragment thereof of claim 19 wherein the antibody or fragment thereof inhibits neurokinin B-mediated vasoconstriction of blood vessels.

23. A method of detecting neurokinin B in a biological sample comprising:
    (a) contacting the biological sample with the antibody or fragment thereof of claim 3; and
    (b) detecting said antibody specifically bound to said neurokinin B.

24. A kit comprising the antibody or fragment thereof of claim 3.

25. The kit of claim 24 comprising a control antibody.

26. The kit of claim 24, wherein the antibody or fragment thereof is coupled or conjugated to a detectable label.

27. The antibody or fragment thereof of claim 3 that binds neurokinin B purified from a cell culture wherein said neurokinin B is encoded by a polynucleotide encoding amino acids 1 to 121 of SEQ ID NO:2.

* * * * *

SEQUENCE LISTING

```
<160> NUMBER OF SEQ ID NOS: 76

<210> SEQ ID NO 1
<211> LENGTH: 832
<212> TYPE: DNA
<213> ORGANISM: Homo sapiens
<220> FEATURE:
<221> NAME/KEY: CDS
<222> LOCATION: (141)..(503)
<223> OTHER INFORMATION:
<220> FEATURE:
<221> NAME/KEY: misc_feature
<222> LOCATION: (821)..(821)
<223> OTHER INFORMATION: n equal any a, t g or c
<220> FEATURE:
<221> NAME/KEY: misc_feature
<222> LOCATION: (825)..(825)
<223> OTHER INFORMATION: n equal any a, t g or c

<400> SEQUENCE: 1
ggcacgagct ccactcggtt tctctctttg caggagcacc ggcagcacca gtgtgtgagg      60
ggagcaggca gcggtcctag ccagttcctt gatcctgcca gaccacccag ccctggcac     120 agagctgctc cacaggcacc atg agg atc atg ctg cta ttc aca gcc atc ctg    173
                      Met Arg Ile Met Leu Leu Phe Thr Ala Ile Leu
                        1               5                      10 gcc ttc agc cta gct cag agc ttt ggg gct gtc tgt aag gag cca cag      221
Ala Phe Ser Leu Ala Gln Ser Phe Gly Ala Val Cys Lys Glu Pro Gln
             15                  20                  25 gag gag gtg gtt cct ggc ggg ggc cgc agc aag agg gat cca gat ctc      269
Glu Glu Val Val Pro Gly Gly Gly Arg Ser Lys Arg Asp Pro Asp Leu
         30                  35                  40 tac cag ctg ctc cag aga ctc ttc aaa agc cac tca tct ctg gag gga      317
Tyr Gln Leu Leu Gln Arg Leu Phe Lys Ser His Ser Ser Leu Glu Gly
     45                  50                  55 ttg ctc aaa gcc ctg agc cag gct agc aca gat cct aag gaa tca aca      365
Leu Leu Lys Ala Leu Ser Gln Ala Ser Thr Asp Pro Lys Glu Ser Thr
 60                  65                  70                  75 tct ccc gag aaa cgt gac atg cat gac ttc ttt gtg gga ctt atg ggc      413
Ser Pro Glu Lys Arg Asp Met His Asp Phe Phe Val Gly Leu Met Gly
                 80                  85                  90 aag agg agc gtc cag cca gac tct cct acg gat gtg aat caa gag aac      461
Lys Arg Ser Val Gln Pro Asp Ser Pro Thr Asp Val Asn Gln Glu Asn
             95                 100                 105 gtc ccc agc ttt ggc atc ctc aag tat ccc ccg aga gca gaa taggtac      510
Val Pro Ser Phe Gly Ile Leu Lys Tyr Pro Pro Arg Ala Glu
        110                 115                 120
```

```
tccacttccg gactcctgga ctgcattagg aagacctctt tccctgtccc aatccccagg    570
tgcgcacgct cctgttaccc tttctcttcc ctgttcttgt aacattcttg tgctttgact    630
ccttctccat cttttctacc tgaccctggt gtggaaactg catagtgaat atccccaacc    690
ccaatgggca ttgactgtag aatacccctag agttcctgta gtgtcctaca ttaaaaatat   750
aatgtctctc tctattcctc aacaataaag gattttttgca tatgaaaaaa aaaaaaaaa   810 aaaaaaaaaa naaanaaaaa aa                                            832
```

```
<210> SEQ ID NO 2
<211> LENGTH: 121
<212> TYPE: PRT
<213> ORGANISM: Homo sapiens

<400> SEQUENCE: 2

Met Arg Ile Met Leu Leu Phe Thr Ala Ile Leu Ala Phe Ser Leu Ala
1               5                   10                  15

Gln Ser Phe Gly Ala Val Cys Lys Glu Pro Gln Glu Glu Val Val Pro
            20                  25                  30

Gly Gly Gly Arg Ser Lys Arg Asp Pro Asp Leu Tyr Gln Leu Leu Gln
        35                  40                  45

Arg Leu Phe Lys Ser His Ser Ser Leu Glu Gly Leu Leu Lys Ala Leu
    50                  55                  60

Ser Gln Ala Ser Thr Asp Pro Lys Glu Ser Thr Ser Pro Glu Lys Arg
65                  70                  75                  80

Asp Met His Asp Phe Phe Val Gly Leu Met Gly Lys Arg Ser Val Gln
                85                  90                  95

Pro Asp Ser Pro Thr Asp Val Asn Gln Glu Asn Val Pro Ser Phe Gly
            100                 105                 110

Ile Leu Lys Tyr Pro Pro Arg Ala Glu
        115                 120
```

```
<210> SEQ ID NO 3
<211> LENGTH: 750
<212> TYPE: DNA
<213> ORGANISM: Artificial sequence
<220> FEATURE:
<223> OTHER INFORMATION: DNA encoding N024C01 scFv

<400> SEQUENCE: 3
caggtacagc tgcagcagtc aggagctgag gtgaagaacc ctgggtcctc ggtgaaggtc    60
tcctgcaagc cttctagaga caccctcagt ggagacaact tcagcagctc tgtcttcagt   120
tgggtccgac aggcccctgg acaagggctt gagtggatgg gagggatcat tcctatcttt   180
ggtgtagcaa actacgcaca gaaattccag cccagagtca ccattagcgc ggacatgtcc   240
acgaacacag cctacatgga gctgagcagc ctgagatctg aggacacggc cgtgtattac   300
tgtgctagca cttgggagct gcgcaatgct tttgatatct ggggcaaggg caccctggtc   360
accgtctcga gtggtggagg cggttcaggc ggaggtggca gcggcggtgg cggatcgcag   420
tctgtgttga cgcagccgcc ctcagtgtct gcggccccag acagaaggt caccatttcc   480 tgctctggaa gcacctccaa cattgggaat aattatgtct cctggtacca acagcaccca   540
ggcaaagccc ccaaactcat gatttatgat gtcagtaagc ggccctcagg ggtccctgac   600
cgattctctg gctccaagtc tggcaactca gcctcctgg acatcagtgg gctccagtct   660
gaggatgagg ctgattatta ctgtgcagca tgggatgaca gcctgagtga atttctcttc   720
ggaactggga ccaagctgac cgtcctaggt                                    750
```

<210> SEQ ID NO 4
<211> LENGTH: 762
<212> TYPE: DNA
<213> ORGANISM: Artificial Sequence
<220> FEATURE:
<223> OTHER INFORMATION: DNA encoding N025B07 scFv

<400> SEQUENCE: 4

```
gaggtgcagc tggtgcagtc tggggctgag gtgaagaagc ctggggcctc agtgagggtt      60
tcctgcaagg catctggata cagcttcacc aacttctata tgcattggct ccgacaggcc     120
cctggtcgag ggcctgagtg gatgggaata attgacccca gtaataatta tacatattac     180
gcacagaagt tccagggcag agtcaccgtg accagggaca cgtccacgag cacagtctac     240
atggagctga gcagcctgag atctgaggac acggccatat attactgtgc tagacccgtc     300
tattactatg atagtagtgg ttattactac ggtcttaatg cttttgatat ctggggccga     360
gggacaatgg tcaccgtctc gagtggtgga ggcggttcag gcggaggtgg cagcggcggt     420
ggcggatcgc agtctgtgtt gacgcagccg ccctcagtgt ctgcggcccc aggacagaag     480
gtcaccattt cctgctctgg aagcacctcc aacattggga ataattatgt ctcctggtac     540
caacagcacc caggcaaagc ccccaaactc atgatttatg atgtcagtaa gcggccctca     600
ggggtccctg accgattctc tggctccaag tctggcaact cagcctccct ggacatcagt     660
gggctccagt ctgaggatga ggctgattat tactgtgcag catgggatga cagcctgagt     720
gaatttctct cggaactggg accaagctg accgtcctag gt                         762
```

<210> SEQ ID NO 5
<211> LENGTH: 726
<212> TYPE: DNA
<213> ORGANISM: Artificial Sequence
<220> FEATURE:
<223> OTHER INFORMATION: DNA encoding N015E08 scFv

<400> SEQUENCE: 5

```
cagatgcagc tgcaggagtc gggggctgag gtgaaaaagc ctgggtcctc ggtgaaggtc      60
tcctgcaagg cttctggaga cacttttcgc agctatatta tcagctgggt gcgacaggcc     120
cctggacaag gacttgagtg gatgggaggg atcatcccta tgtttggcac aacaaactat     180
gcacagcaat tccagggcaa agtcaccatt accgcggacg actccacgag tacttcttat     240
atggagctga ggagcctgag atctgacgac acggccgtgt attactgtgc gagaggaact     300
aactacatgg acgtctgggg gcaggggacc acggtcaccg tctcctcagg tggaggcggt     360
tcaggcggag gtggcagcgg cggtggcgga tcgcagtctg tgttgacgca gccgccctca     420
gtgtctgcgg ccccaggaca gaaggtcacc atttcctgct ctggaagcac ctccaacatt     480
gggaataatt atgtctcctg gtaccaacag cacccaggca aagcccccaa actcatgatt     540
tatgatgtca gtaagcggcc ctcaggggtc cctgaccgat tctctggctc caagtctggc     600
aactcagcct ccctggacat cagtgggctc cagtctgagg atgaggctga ttattactgt     660
gcagcatggg atgacagcct gagtgaattt ctcttcggaa ctgggaccaa gctgaccgtc     720
ctaggt                                                                726
```

<210> SEQ ID NO 6
<211> LENGTH: 744
<212> TYPE: DNA
<213> ORGANISM: Artificial Sequence
<220> FEATURE:

<223> OTHER INFORMATION: DNA encoding N015F10 scFv

<400> SEQUENCE: 6

| | | |
|---|---|---|
| caggtacagc tgcagcagtc aggggctgag gtgaagaagc ctgggtcgtc ggtgaaggtc | 60 |
| tcctgcaagg cttctggagg caccttcagc agctatgcta tcagctgggt gcgccaggcc | 120 |
| cctggacaag gcttgagtg gatgggaggg agcatcccta aatttcgtac agcaaactac | 180 |
| gcaaagaagt tccagggcag agtcacgatt accgctgacg aatccacgag cacagcctac | 240 |
| atggagctga gcagcctgag atctgatgac acggccgtgt attactgtgc gagagggagt | 300 |
| gcctacaata tacggaacgc ttttgatatc tggggcagg gaccacggt caccgtctcg | 360 |
| agtggaggcg gcggttcagg cggaggtggc tctggcggtg gcggaagtgc acagtctgtc | 420 |
| gtgacgcagc cgccctcagt gtctgcgccc caggacaga gggtcaccat ctcctgctct | 480 |
| ggaagcagct ccaacattgc gaataattat gtgtcctggt accagcagct cccaggaaca | 540 |
| gccccccaaac tcctcattta tgacaataat aagcgaccct cagggattcc tgaccgattc | 600 |
| tctggctcca gtctggcac gtcagccacc ctgggcatca ccggactcca gactggggac | 660 |
| gaggccgatt attactgcgg aacatgggat agcagcctga gtgcttatgt cttcggaact | 720 |
| gggaccaagg tcaccgtcct aggt | 744 |

<210> SEQ ID NO 7
<211> LENGTH: 732
<212> TYPE: DNA
<213> ORGANISM: Artificial Sequence
<220> FEATURE:
<223> OTHER INFORMATION: DNA encoding N024D01 scFv

<400> SEQUENCE: 7

| | | |
|---|---|---|
| caggtacagc tgcagcagtc aggggggaggc gtggtccagc ctgggaggtc cctgagactc | 60 |
| tcctgtgcag cgtctggatt caccttgat gattatgcca tgcactgggt ccggcaagct | 120 |
| ccagggaagg gcctggagtg ggtctcaggt attagttgga atagtggtag cataggctat | 180 |
| gcggactctg tgaagggccg attcaccatc tccagagaca cgccaagaa ctccctgtat | 240 |
| ctgcaaatga acagtctgag agctgaggac acggccttgt attactgtgc aaaaacgggc | 300 |
| ggtggtaact tcttgacta ctggggccga ggaaccctgg tcaccgtctc ctcaggtgga | 360 |
| ggcggttcag gcggaggtgg cagcggcggt ggcggatcgc agtctgtgtt gacgcagccg | 420 |
| ccctcagtgt ctgcggcccc aggacagaag gtcaccattt cctgctctgg aagcacctcc | 480 |
| aacattggga ataattatgt ctcctggtac caacagcacc caggcaaagc ccccaaactc | 540 |
| atgatttatg atgtcagtaa gcggccctca ggggtccctg accgattctc tggctccaag | 600 |
| tctggcaact cagcctccct ggacatcagt gggctccagt ctgaggatga ggctgattat | 660 |
| tactgtcag catgggatga cagcctgagt gaatttctct tcggaactgg gaccaagctg | 720 |
| accgtcctag gt | 732 |

<210> SEQ ID NO 8
<211> LENGTH: 741
<212> TYPE: DNA
<213> ORGANISM: Artificial Sequence
<220> FEATURE:
<223> OTHER INFORMATION: DNA encoding N015D08 scFv

<400> SEQUENCE: 8

| | | |
|---|---|---|
| caggtgcagc tgttgcagtc tgcgcctgag gtgaagaagc ctgggtcctc ggttagggtc | 60 |
| tcctgcaaga cttctggagg caccttcagc agccaactta tcaactgggt gcgacagccc | 120 |

-continued

```
cctggacaag ggcctgaatg gatgggaggg atcatcccta tctttggtac agcaaactac      180
gcacagaagt tccagggcag agtcacgatt accgcggacg aatccacgag cacagcctac      240
atggagctga gcagcctgag atctgaggac acggccgtgt attactgtgc gagagatctg      300
actgccggac gttttgatgc ttttcatatc tggggcagag gcaccctggt caccgtctcc      360
tcaggtggag gcggttcagg cggaggtggc agcggcggtg gcggatcgca gtctgtgttg      420
acgcagccgc cctcagtgtc tgcggcccca ggacagaagg tcaccatttc ctgctctgga      480
agcacctcca acattgggaa taattatgtc tcctggtacc aacagcaccc aggcaaagcc      540
cccaaactca tgatttatga tgtcagtaag cggccctcag gggtccctga ccgattctct      600
ggctccaagt ctggcaactc agcctccctg acatcagtg gctccagtc tgaggatgag      660 gctgattatt actgtgcagc atgggatgac agcctgagtg aatttctctt cggaactggg      720
accaagctga ccgtcctagg t                                                741
```

<210> SEQ ID NO 9
<211> LENGTH: 744
<212> TYPE: DNA
<213> ORGANISM: Artificial Sequence
<220> FEATURE:
<223> OTHER INFORMATION: DNA encoding N024B07 scFv

<400> SEQUENCE: 9

```
caggtacagc tgcagcagtc aggggctgag gtgaagaagc ctgggtcgtc ggtgaaggtc       60
tcctgcaagg cttctggagg caccttcagc agctatgcta tcagctgggt gcgccaggcc      120
cctggacaag ggcttgagtg gatgggaggg agcatcccta aatttcgtac agcaaactac      180
gcaaagaagt tccagggcag agtcacgatt accgctgacg aatccacgag cacagcctac      240
atggagctga gcagcctgag atctgatgac acggccgtgt attactgtgc gagagggagt      300
acctacaatc tacggaacgc ttttgatatc tggggcaagg gcaccctggt caccgtctcg      360
agtggaggcg gcggttcagg cggaggtggc tctggcggtg gcggaagtgc acagtctgtc      420
gtgacgcagc cgccctcagc gtctgggacc cccgggcaga gggtcaccat ctcttgttct      480
ggaggcagct ccaacatcgg aaggaatact gttaactggt accagcaggt cccaggaacg      540 gccccccaaac tcctcatcta tactaataat cagcggccct caggggtccc tgaccgattc      600
tctggctcca agtctggcac ctcagcctcc ctggccatca gtggactcca gtctgaggat      660
gaggctgatt attactgtgc agcatgggat gacagcctga tgatgtgga attcggcgga      720 gggaccaagc tgaccgtcct aggt                                             744
```

<210> SEQ ID NO 10
<211> LENGTH: 729
<212> TYPE: DNA
<213> ORGANISM: Artificial Sequence
<220> FEATURE:
<223> OTHER INFORMATION: DNA encoding N024E07 scFv

<400> SEQUENCE: 10

```
caggtgcagc tgcaggagtc gggggggaggc ttggaacagc ctggcaggtc cctgagactc       60
tcctgtacag cctctggatt caccttttgat gattatccca tgcactgggt ccggcaagct      120
ccagggaagg gcctggagtg ggtctcaggt attagtggga atagtgatag aatagcctat      180
gcggactctg tgaagggccg attcaccatc tccagagaca actccaagaa cacgctgtgg      240
ctgcaaatga acagcctgag agctgaagac acggccatat attactgtgc gagagcagcg      300
```

```
cggaactggt tcgacccctg gggccaagga accctggtca ccgtctcgag tggtggaggc    360
ggctcaggcg gaggtggcag cggcggtggc ggatcgcagt ctgtgttgac gcagccgccc    420
tcagtgtctg cggccccagg acagaaggtc accatttcct gctctggaag cacctccaac    480
attgggaata attatgtctc ctggtaccaa cagcacccag caaagcccca caaactcatg    540
atttatgatg tcagtaagcg gccctcaggg gtccctgacc gattctctgg ctccaagtct    600
ggcaactcag cctccctgga catcagtggg ctccagtctg aggatgaggc tgattattac    660
tgtgcagcat gggatgacag cctgagtgaa tttctcttcg gaactgggac caagctgacc    720
gtcctaggt                                                            729

<210> SEQ ID NO 11
<211> LENGTH: 765
<212> TYPE: DNA
<213> ORGANISM: Artificial Sequence
<220> FEATURE:
<223> OTHER INFORMATION: DNA encoding N023F05 scFv

<400> SEQUENCE: 11
caggtccagc tggtgcagtc tggggctgag gtgaagaagc ctgggttctc ggtgaaggtc     60
tcctgtaagg cttctggagg cagcttcagc aactatgtta ttagctggct gcgacaggcc    120
cctggacagg gctggagtg atgggaggc atcatgccta tctttggtaa tgcaaattac    180
gcacagaagt tccaggacag agtcacgatc accgcggaca atccacgag cacagcctac    240 atggaactga gcagcctgag atctgacgac acggccgtat attactgtgc gagagaccaa    300
attgtcgtag acccagtgac taagggtgcc tattacagcg gtttggacgt ctggggcaga    360
gggacaatgg tcaccgtctc gagtggaggc ggcggttcag gcggaggtgg ctctggcggt    420
ggcggaagtg cacagtctgt gctgactcag ccaccctcag cgtctgggac ccccgggcag    480
agggtcacca tctcttgttc tggaggcagc tccaacatcg gagctaatgc tataacctgg    540
ttccagcagc tcccaggaac ggcccccaaa ctcctcatct atcataataa tcaacgaccc    600
tcaggggtcc ctgaccgatt ctctggctcc aagtctggca cctcaggctc cctggccatc    660
agtgggctcc agtctgagga tgaggctgat tattactgtg cagtatggga taacagcctg    720
aatgctatgt tattcggcgg agggaccaag ctgaccgtcc taggt                    765

<210> SEQ ID NO 12
<211> LENGTH: 735
<212> TYPE: DNA
<213> ORGANISM: Artificial Sequence
<220> FEATURE:
<223> OTHER INFORMATION: DNA encoding N024D08 scFv

<400> SEQUENCE: 12
gaggtccagc tggtgcagtc tggggctgag gtgaagaggc cggggggcctc agtcaagatc     60 tcctgcagga cgtctggata caccttcacc agttactata cactgggt gcgacaggcc    120 cctggacaag gccttgagtg gctggcgata atcaacccta ctgctggcaa cacatactac    180
acacaggact tccaggacag agtcaccgtg accagagaca cgtccacgag cacagtgtac    240
atggagctga ggggactgaa ctcagaggac acggccgtgt attactgtgc gagcccgtac    300
ggtgtccgaa atgcttttga tgtctgggc caagggacaa tggtcaccgt ctcctcaggt    360
ggaggcggtt caggcggagg tggcagcggc ggtggcggat cgcagtctgt gttgacgcag    420 ccgcccctcag tgtctgcggc cccaggacag aaggtcacca tttcctgctc tggaagcacc    480
tccaacattg gaataatta tgtctcctgg taccaacagc acccaggcaa agccccaaa    540
```

```
ctcatgattt atgatgtcag taagcggccc tcaggggtcc ctgaccgatt ctctggctcc    600
aagtctggca actcagcctc cctggacatc agtgggctcc agtctgagga tgaggctgat    660
tattactgtg cagcatggga tgacagcctg agtgaatttc tcttcggaac tgggaccaag    720
ctgaccgtcc taggt                                                     735
```

<210> SEQ ID NO 13
<211> LENGTH: 744
<212> TYPE: DNA
<213> ORGANISM: Artificial Sequence
<220> FEATURE:
<223> OTHER INFORMATION: DNA encoding N023B03 scFv
<400> SEQUENCE: 13

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagacaggga    300
agtgggagct atcctccccc cgcttttgac tcctggggcc agggacaat ggtcaccgtc    360 tcgagtggag gcggcggttc aggcggaggt ggctctggcg gtggcggaag tgcacaggct    420
gtggtgatcc aggagccctc actgactgtg tccccaggag gacagtcac tctcacctgt    480 gctttcaact ctggacaagt caccagtggt ttctatccaa actggttcca gcagaaacct    540
ggacaaccac cccggtcact gatctataat acagacaaca acattcctg accctgcc       600 cgcttctcag gctccctcct tggggcaaa gctgccttga cactgtccgg tgtgcagcct    660
gacgacgagg ctgactatta ctgccttctc tattatgatc gtagtctggt gttcggcgga    720
gggaccaagc tgaccgtcct aggt                                           744
```

<210> SEQ ID NO 14
<211> LENGTH: 729
<212> TYPE: DNA
<213> ORGANISM: Artificial Sequence
<220> FEATURE:
<223> OTHER INFORMATION: DNA encoding N023E01 scFv
<400> SEQUENCE: 14

```
caggtgcagc tggtgcagtc tgggggaggc ttggtacagc ctgcaggtc cctgagactc      60 tcttgtgcag cctctggatt cacctttgat gattatgcca tgcactgggt ccggcaagct    120
ccagggaagg gcctggagtg gtctcaggt attagttgga atagtgccag cataggttat    180
gcggactctg tgaagggccg attcaccatc tccagagaca cgccaagaa ctccctgtat    240 ctgcaaatga acagtctgag aggtgaggac acggccttat attactgtgc aaaaggagcc    300
cgtgatgctt tggatatctg gggcaaggga accctgctca ccgtctcctc aggtggaggc    360
ggttcaggcg gaggtggcag cggcggtggc ggatcgcagt ctgtgttgac gcagccgccc    420
tcagtgtctg cggccccagg acagaaggtc accatttcct gctctggaag cacctccaac    480
attgggaata attatgtctc ctggtaccaa cagcacccag gcaaagcccc caaactcatg    540
atttatgatg tcagtaagcg gccctcaggg gtccctgacc gattctctgg ctccaagtct    600
ggcaactcag cctccctgga catcagtggg ctccagtctg aggatgaggc tgattattac    660
tgtgcagcat gggatgacag cctgagtgaa tttctcttcg gaactgggac caagctgacc    720
```

<210> SEQ ID NO 15
<211> LENGTH: 753
<212> TYPE: DNA
<213> ORGANISM: Artificial Sequence
<220> FEATURE:
<223> OTHER INFORMATION: DNA encoding N024C05 scFv

<400> SEQUENCE: 15

| | | |
|---|---|---|
| caggtacagc tgcagcagtc aggtccagga ctggtgaagc cctcgcagac cctctcactc | 60 |
| acctgtgcca tctccgggga cagtgtctct agcaacactg ctgcctggag ctggatcagg | 120 |
| cagtccccat cgagaggcct tgagtggctg gaaggacat actacagcag gtccaagtgg | 180 |
| tataaagatt atgcagtatc tgtgaaaagt cgaataacca tcaatccaga cacatccaag | 240 |
| aaccagttct ccctgcagct ggactctgtg actcccgagg acacggctgt gtattattgt | 300 |
| acaagagagg gctactatga ttatagtggt gtcgttgact actggggca ggggaccacg | 360 |
| gtcatcgtct cgagtggtgg aggcggttca ggcggaggtg gcagcggcgg tggcggatcg | 420 |
| cagtctgtgc tgactcagcc tcctccgcg tccgggtctc ctggacagtc agtcaccatc | 480 |
| tcctgcactg gaaccagcag tgatgttggt ggttataact atgtctcctg gtaccaacag | 540 |
| cacccaggca agccccccaa attcatgatt tatgatgtca gtaagcggcc ctcaggggtt | 600 |
| tctaatcgct tctctggctc caagtctggc aacacggcgt ccctgaccat ctctggggtc | 660 |
| caggctgagg acgaggctga ttattactgc agctcatata aagcgccag cactgtgata | 720 |
| ttcggcggag ggaccaagct gaccgtccta ggt | 753 |

<210> SEQ ID NO 16
<211> LENGTH: 735
<212> TYPE: DNA
<213> ORGANISM: Artificial Sequence
<220> FEATURE:
<223> OTHER INFORMATION: DNA encoding N025E05 scFv

<400> SEQUENCE: 16

| | | |
|---|---|---|
| caggtacagc tgcagcagtc aggggctgag gtgaagaagc ctgggtcctc ggtgaaggtc | 60 |
| tcctgcaagg cttctggaga caccttcagt agcaatacta tcagctgggt acgacaggcc | 120 |
| cctggacaag ggcttgagtg gatgggaggg atcatcccta tcattggaac accacactac | 180 |
| gcacagaaat tccagggcag agtcacaata accgctgaca gatccacgag cacagcctac | 240 |
| atggagctga ccaacctgag atctgaggac acggccgtat atttctgtgc gagaaaccga | 300 |
| gtggggacta gcagctttga cttctggggc caggggacaa tggtcaccgt ctcgagtgga | 360 |
| ggcggcggtt caggcggagg tggctctggc ggtggcggaa gtgcactgcc tgtgctgact | 420 |
| cagccaccct cagcgtctgg gaccccgggg cagagggtca ccatctcttg ttctggaagc | 480 |
| agctccaaca tcggaagtaa tactgtaaac tggtaccagc agctcccagg aacgccccc | 540 |
| aaactcttca tctatagtaa taatcagcgg ccctcagggg tccctgaccg attctctggc | 600 |
| tccaagtctg gcacctcagc ctccctggcc atcagtgggc tccagtctga agatgaggct | 660 |
| gattattact gttcatcatg ggatgacagc ctgaatttga tattcggcgg ggggaccaag | 720 |
| gtcaccgtcc taggt | 735 |

<210> SEQ ID NO 17
<211> LENGTH: 735
<212> TYPE: DNA
<213> ORGANISM: Artificial Sequence
<220> FEATURE:
<223> OTHER INFORMATION: DNA encoding N025C01 scFv

<400> SEQUENCE: 17

| | | | | | |
|---|---|---|---|---|---|
| caggtgcagc | tggtgcagtc | tggggctgag | gtgaagaagc | tgggacctc | ggtgaaggtc | 60 |
| tcctgcaagg | ctgctggaga | cactttccgc | agctatatta | tcagctgggt | gcgacaggcc | 120 |
| cctggacaag | gacttgagtg | gatgggaggg | atcatcccta | tgtttggcac | atcaaactac | 180 |
| gcacagaagt | tccagggcag | agtcacgatt | accgcggacg | attccacgag | cacagcctac | 240 |
| atggagctga | gcagcctgag | atctgaggac | acggccgtgt | attactgtgc | gaggacggcc | 300 |
| caggggggga | gctactacaa | ctactgggc | caaggaaccc | cggtcaccgt | ctcgagtggt | 360 |
| ggaggcggtt | caggcggagg | tggcagcggc | ggtggcggat | cgcagtctgt | gttgacgcag | 420 |
| ccgccctcag | tgtctgcggc | cccaggacag | aaggtcacca | tttcctgctc | tggaagcacc | 480 |
| tccaacattg | gaataatta | tgtctcctgg | taccaacagc | acccaggcaa | agccccccaaa | 540 |
| ctcatgattt | atgatgtcag | taagcggccc | tcaggggtcc | ctgaccgatt | ctctggctcc | 600 |
| aagtctggca | actcagcctc | cctggacatc | agtgggctcc | agtctgagga | tgaggctgat | 660 |
| tattactgtg | cagcatggga | tgacggcctg | agtgaattc | cttcggaac | tgggaccaag | 720 |
| ctgaccgtcc | taggt | | | | | 735 |

<210> SEQ ID NO 18
<211> LENGTH: 741
<212> TYPE: DNA
<213> ORGANISM: Artificial Sequence
<220> FEATURE:
<223> OTHER INFORMATION: DNA encoding N024F09 scFv

<400> SEQUENCE: 18

| | | | | | |
|---|---|---|---|---|---|
| caggtacagc | tgcagcagtc | aggggctgag | gtgaagaagc | tggggcctc | agtgaaggtc | 60 |
| tcctgcaagg | cttctggata | caccttcacc | ggctactata | tgcactgggt | gcgacaggcc | 120 |
| cctggacaac | gacttgagtg | gatgggaggg | atcctccctt | tttttggtac | aacaagctac | 180 |
| gcacaaaatt | tccacggcag | actcacaatt | accgcggacg | aatccacgcg | cacagcctac | 240 |
| atggagctga | gcagcctaaa | atctgaagac | acggccgttt | attactgtgc | gagagatgag | 300 |
| tccgcggatc | ccaaaaatgc | ttttgatatc | tggggccgag | ggacaatggt | caccgtctct | 360 |
| tcaggtggag | gcggttcagg | cggaggtggc | agcggcggtg | gcggatcgca | gtctgtgttg | 420 |
| acgcagccgc | ccccagtgtc | tgcggcccca | ggacagaagg | tcaccatttc | ctgctctgga | 480 |
| agcacctcca | acattgggaa | taattatgtc | tcctggtacc | aacagcgccc | aggcaaagcc | 540 |
| cccaaactca | tgatttatga | tgtcagtaag | cggccctcag | gggtccccga | ccgattctct | 600 |
| ggctccaagt | ctggcaactc | agcctccctg | gacatcagtg | ggctccagtc | tgaggatgag | 660 |
| gctgattatt | actgtgcagc | atgggatgac | agcctgagtg | aatttctctt | cggaactggg | 720 |
| accaagctga | ccgtcctagg | t | | | | 741 |

<210> SEQ ID NO 19
<211> LENGTH: 738
<212> TYPE: DNA
<213> ORGANISM: Artificial Sequence
<220> FEATURE:
<223> OTHER INFORMATION: DNA encoding N024B01 scFv

<400> SEQUENCE: 19

| | | | | | |
|---|---|---|---|---|---|
| caggtacagc | tgcagcagtc | agggaatgag | gtgaagaagc | tgggtcctc | ggtgaagatc | 60 |

-continued

```
tcctgcaagg cttccggagc ccccttcaat agttatgtta tcagttgggt gcggcaggcc    120
cctggacaag ggcttgagtg ggtgggaggg gtcgtcccca tctttggcac agcacactac    180
gcacaccagt tccagggcag agtcaccatt atcgcggaca gtcgacgag cacagtctac     240 atggagttgc gcggcctgac atcggacgac acggccgaat attttttgtgc gagacaaggc   300 ccctatggca aacttgacga ttggggccag gggacaatgg tcaccgtctc gagtggaggc    360
ggcggttcag gcggaggtgg ctctggcggt ggcggaagtg cactttccta tgagctgact    420
cagccaccct cagcgtctgg aaccccgggg cagagggtca ccatctcttg ttctggaagc    480
agctccaata tcggaagtaa ttatgtatac tggtaccagc agttcccagg aacgccccc    540 aaactcctca tgtataggaa taatcagcgg ccctcagggg tccctgaccg attctctggc    600
tccaagtttg gcacctcagc ctccctggcc atcagtgggc tccggtccga ggatgaggct    660
gattattact gtgcagcatg ggatgacagc ctgactggtc gggtattcgg cggagggacc    720
aaggtcaccg tcctaggt                                                   738
```

<210> SEQ ID NO 20
<211> LENGTH: 744
<212> TYPE: DNA
<213> ORGANISM: Artificial Sequence
<220> FEATURE:
<223> OTHER INFORMATION: DNA encoding N024F07 scFv

<400> SEQUENCE: 20

```
caggtacagc tgcagcagtc aggggctgag gtgaagaagc ctgggtcctc ggtgaacgtc     60
tcctgcaagg cttctggagg caccttcgac acttttggca tcagctgggt gcggcaggct    120
ccaggcaagg gtctggagtg gatgggagtt atagcacatg atggaagtat ttcatactat    180
gcagactccg tgaagggccg attcaccttc tccagagaca attccaagaa cacggtgtct    240
ctgcaaatga acagcccgag acctgaggac acggctgtgt attactgtgc gaaggggag    300 tatgatagta gtggttacaa tgcttttgat atctggggca agggcaccct ggtcaccgtc    360
tcgagtggtg gaggcggttc aggcggaggt ggcagcggcg gtggcggatc gcagtctgtg    420
ttgacgcagc cgccctcagt gtctgcggcc ccaggacaga aggtcaccgt tcctgctct    480 ggaagcacct ccaacattgg gaataattat gtctcctggt accaacagca cccaggcaaa    540
gcccccaaac tcatgattta tgatgtcagt aagcggccct caggggtccc tgaccgattc    600
tctggctcca gtctggcaa tcagcctcc ctggacatca gtgggctcca gtctgaggat    660
gaggctgatt attactgtgc agcatgggat gacagcctga gtgaatttct cttcggaact    720
gggaccaagc tgaccgtcct aggt                                            744
```

<210> SEQ ID NO 21
<211> LENGTH: 726
<212> TYPE: DNA
<213> ORGANISM: Artificial Sequence
<220> FEATURE:
<223> OTHER INFORMATION: DNA encoding N015D10 scFv

<400> SEQUENCE: 21

```
caggtgcagc tggtgcagtc tggggctgaa gtgaagaagc ctgggtcctc ggtgaggatc     60
tcctgcaagg cttctggggg cagcttcagg acttatgttg tcagctgggt gcgacaggcc    120
cctggacaag ggcttgagtg gatgggaggg atcattcctg tctatggcac accaaactac    180
gcacagaagt tccagggcag agtcacgatt accgcggacg aacctacgag aacaacctac    240
atggagctga gcagcctgag atcagaggac acggccgtgt attattgtgc gagaaatggt    300
```

```
ggggcccttg attactgggg ccaagggaca atggtcaccg tctcgagtgg tggaggcggt    360
tcaggcggag gtggcagcgg cggtggcgga tcgcagtctg tgttgacgca gccgccctca    420
gtgtctgcgg ccccaggaca gaaggtcacc atttcctgct ctggaagcac ctccaacatt    480
gggaataatt atgtctcctg gtaccaacag cacccaggca aagcccccaa actcatgatt    540
tatgatgtca gtaagcggcc ctcaggggtc cctgaccgat tctctggctc caagtctggc    600
aactcagcct ccctggacat cagtgggctc cagtctgagg atgaggccga ttattactgt    660
gcagcatggg atgacagcct gagtgaattt ctcttcggaa ctgggaccaa gctgaccgtc    720
ctaggt                                                                726
```

<210> SEQ ID NO 22
<211> LENGTH: 250
<212> TYPE: PRT
<213> ORGANISM: Artificial sequence
<220> FEATURE:
<223> OTHER INFORMATION: N024C01 scFv

<400> SEQUENCE: 22

```
Gln Val Gln Leu Gln Gln Ser Gly Ala Glu Val Lys Asn Pro Gly Ser
  1               5                  10                  15

Ser Val Lys Val Ser Cys Lys Pro Ser Arg Asp Thr Leu Ser Gly Asp
                 20                  25                  30

Asn Phe Ser Ser Val Phe Ser Trp Val Arg Gln Ala Pro Gly Gln
             35                  40                  45

Gly Leu Glu Trp Met Gly Gly Ile Ile Pro Ile Phe Gly Val Ala Asn
         50                  55                  60

Tyr Ala Gln Lys Phe Gln Pro Arg Val Thr Ile Ser Ala Asp Met Ser
 65                  70                  75                  80

Thr Asn Thr Ala Tyr Met Glu Leu Ser Ser Leu Arg Ser Glu Asp Thr
                 85                  90                  95

Ala Val Tyr Tyr Cys Ala Ser Thr Trp Glu Leu Arg Asn Ala Phe Asp
                100                 105                 110

Ile Trp Gly Lys Gly Thr Leu Val Thr Val Ser Ser Gly Gly Gly Gly
            115                 120                 125

Ser Gly Gly Gly Gly Ser Gly Gly Gly Gly Ser Gln Ser Val Leu Thr
130                 135                 140

Gln Pro Pro Ser Val Ser Ala Ala Pro Gly Gln Lys Val Thr Ile Ser
145                 150                 155                 160

Cys Ser Gly Ser Thr Ser Asn Ile Gly Asn Asn Tyr Val Ser Trp Tyr
                165                 170                 175

Gln Gln His Pro Gly Lys Ala Pro Lys Leu Met Ile Tyr Asp Val Ser
            180                 185                 190

Lys Arg Pro Ser Gly Val Pro Asp Arg Phe Ser Gly Ser Lys Ser Gly
        195                 200                 205

Asn Ser Ala Ser Leu Asp Ile Ser Gly Leu Gln Ser Glu Asp Glu Ala
    210                 215                 220

Asp Tyr Tyr Cys Ala Ala Trp Asp Asp Ser Leu Ser Glu Phe Leu Phe
225                 230                 235                 240

Gly Thr Gly Thr Lys Leu Thr Val Leu Gly
                245                 250
```

<210> SEQ ID NO 23
<211> LENGTH: 251
<212> TYPE: PRT

```
<213> ORGANISM: Artificial sequence
<220> FEATURE:
<223> OTHER INFORMATION: N025B07 scFv

<400> SEQUENCE: 23
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Arg | Val | Ser | Cys | Lys | Ala | Ser | Gly | Tyr | Ser | Phe | Thr | Asn | Phe |
| | | | 20 | | | | | 25 | | | | | 30 | | |
| Tyr | Met | His | Trp | Leu | Arg | Gln | Ala | Pro | Gly | Arg | Gly | Pro | Glu | Trp | Met |
| | | 35 | | | | | 40 | | | | | 45 | | | |
| Gly | Ile | Ile | Asp | Pro | Ser | Asn | Asn | Tyr | Thr | Tyr | Ala | Gln | Lys | Arg | |
| | 50 | | | | | 55 | | | | | 60 | | | | |
| Val | Thr | Val | Thr | Arg | Asp | Thr | Ser | Thr | Ser | Thr | Val | Tyr | Met | Glu | Leu |
| 65 | | | | | 70 | | | | | 75 | | | | | 80 |
| Ser | Ser | Leu | Arg | Ser | Glu | Asp | Thr | Ala | Ile | Tyr | Tyr | Cys | Ala | Arg | Pro |
| | | | | 85 | | | | | 90 | | | | | 95 | |
| Val | Tyr | Tyr | Tyr | Asp | Ser | Ser | Gly | Tyr | Tyr | Tyr | Gly | Leu | Asn | Ala | Phe |
| | | | 100 | | | | | 105 | | | | | 110 | | |
| Asp | Ile | Ser | Trp | Gly | Arg | Gly | Thr | Met | Val | Thr | Val | Ser | Gly | Gly | Gly |
| | | 115 | | | | | 120 | | | | | 125 | | | |
| Gly | Ser | Gly | Gly | Gly | Gly | Ser | Gly | Gly | Gly | Gly | Ser | Gln | Ser | Val | Leu |
| | 130 | | | | | 135 | | | | | 140 | | | | |
| Thr | Gln | Pro | Pro | Ser | Val | Ser | Ala | Ala | Pro | Gly | Gln | Lys | Val | Thr | Ile |
| 145 | | | | | 150 | | | | | 155 | | | | | 160 |
| Ser | Cys | Ser | Gly | Ser | Thr | Ser | Asn | Ile | Gly | Asn | Asn | Tyr | Val | Ser | Trp |
| | | | | 165 | | | | | 170 | | | | | 175 | |
| Tyr | Gln | Gln | His | Pro | Gly | Lys | Ala | Pro | Lys | Leu | Met | Ile | Tyr | Asp | Val |
| | | | 180 | | | | | 185 | | | | | 190 | | |
| Ser | Lys | Arg | Pro | Ser | Gly | Val | Pro | Asp | Arg | Phe | Ser | Gly | Ser | Lys | Ser |
| | | 195 | | | | | 200 | | | | | 205 | | | |
| Gly | Asn | Ser | Ala | Ser | Leu | Asp | Ile | Ser | Gly | Leu | Gln | Ser | Glu | Asp | Glu |
| | 210 | | | | | 215 | | | | | 220 | | | | |
| Ala | Asp | Tyr | Tyr | Cys | Ala | Ala | Trp | Asp | Asp | Ser | Leu | Ser | Glu | Phe | Leu |
| 225 | | | | | 230 | | | | | 235 | | | | | 240 |
| Phe | Gly | Thr | Gly | Thr | Lys | Leu | Thr | Val | Leu | Gly | | | | | |
| | | | | 245 | | | | | 250 | | | | | | |

```
<210> SEQ ID NO 24
<211> LENGTH: 242
<212> TYPE: PRT
<213> ORGANISM: Artificial sequence
<220> FEATURE:
<223> OTHER INFORMATION: N015E08 scFv

<400> SEQUENCE: 24
```

| | | | | | | | | | | | | | | | |
|---|---|---|---|---|---|---|---|---|---|---|---|---|---|---|---|
| Gln | Met | Gln | Leu | Gln | Glu | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Asp | Thr | Phe | Arg | Ser | Tyr |
| | | | 20 | | | | | 25 | | | | | 30 | | |
| Ile | Ile | Ser | Trp | Val | Arg | Gln | Ala | Pro | Gly | Gln | Gly | Leu | Glu | Trp | Met |
| | | 35 | | | | | 40 | | | | | 45 | | | |
| Gly | Gly | Ile | Ile | Pro | Met | Phe | Gly | Thr | Thr | Asn | Tyr | Ala | Gln | Gln | Phe |
| | 50 | | | | | 55 | | | | | 60 | | | | |
| Gln | Gly | Lys | Val | Thr | Ile | Thr | Ala | Asp | Asp | Ser | Thr | Ser | Thr | Ser | Tyr |
| 65 | | | | | 70 | | | | | 75 | | | | | 80 |

-continued

```
Met Glu Leu Arg Ser Leu Arg Ser Asp Asp Thr Ala Val Tyr Tyr Cys
                85                  90                  95

Ala Arg Gly Thr Asn Tyr Met Asp Val Trp Gly Gln Gly Thr Thr Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Val Ser Ala Ala
    130                 135                 140

Pro Gly Gln Lys Val Thr Ile Ser Cys Ser Gly Ser Thr Ser Asn Ile
145                 150                 155                 160

Gly Asn Asn Tyr Val Ser Trp Tyr Gln Gln His Pro Gly Lys Ala Pro
                165                 170                 175

Lys Leu Met Ile Tyr Asp Val Ser Lys Arg Pro Ser Gly Val Pro Asp
            180                 185                 190

Arg Phe Ser Gly Ser Lys Ser Gly Asn Ser Ala Ser Leu Asp Ile Ser
        195                 200                 205

Gly Leu Gln Ser Glu Asp Glu Ala Asp Tyr Tyr Cys Ala Ala Trp Asp
    210                 215                 220

Asp Ser Leu Ser Glu Phe Leu Phe Gly Thr Gly Thr Lys Leu Thr Val
225                 230                 235                 240

Leu Gly

<210> SEQ ID NO 25
<211> LENGTH: 248
<212> TYPE: PRT
<213> ORGANISM: Artificial sequence
<220> FEATURE:
<223> OTHER INFORMATION: N015F10 scFv

<400> SEQUENCE: 25

Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ser Ile Pro Lys Phe Arg Thr Ala Asn Tyr Ala Lys Lys Phe
    50                  55                  60

Gln Gly Arg Val Thr Ile Thr Ala Asp Glu Ser Thr Ser Thr Ala Tyr
 65                 70                  75                  80

Met Glu Leu Ser Ser Leu Arg Ser Asp Asp Thr Ala Val Tyr Tyr Cys
                85                  90                  95

Ala Arg Gly Ser Ala Tyr Asn Leu Arg Asn Ala Phe Asp Ile Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Ala Gln Ser Val Val Thr Gln Pro
    130                 135                 140

Pro Ser Val Ser Ala Ala Pro Gly Gln Arg Val Thr Ile Ser Cys Ser
145                 150                 155                 160

Gly Ser Ser Ser Asn Ile Ala Asn Asn Tyr Val Ser Trp Tyr Gln Gln
                165                 170                 175

Leu Pro Gly Thr Ala Pro Lys Leu Leu Ile Tyr Asp Asn Asn Lys Arg
            180                 185                 190

Pro Ser Gly Ile Pro Asp Arg Phe Ser Gly Ser Lys Ser Gly Thr Ser
```

```
                195             200             205
Ala Thr Leu Gly Ile Thr Gly Leu Gln Thr Gly Asp Glu Ala Asp Tyr
    210             215             220

Tyr Cys Gly Thr Trp Asp Ser Ser Leu Ser Ala Tyr Val Phe Gly Thr
225             230             235             240

Gly Thr Lys Val Thr Val Leu Gly
            245

<210> SEQ ID NO 26
<211> LENGTH: 244
<212> TYPE: PRT
<213> ORGANISM: Artificial sequence
<220> FEATURE:
<223> OTHER INFORMATION: N024D01 scFv

<400> SEQUENCE: 26

Gln Val Gln Leu Gln Gln Ser Gly Gly Val Val Gln Pro Gly Arg
  1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Thr Gly Gly Gly Asn Ser Leu Asp Tyr Trp Gly Arg Gly Thr
            100                 105                 110

Leu Val Thr Val Ser Ser Gly Gly Gly Ser Gly Gly Gly Gly Ser
        115                 120                 125

Gly Gly Gly Gly Ser Gln Ser Val Leu Thr Gln Pro Pro Ser Val Ser
    130                 135                 140

Ala Ala Pro Gly Gln Lys Val Thr Ile Ser Cys Ser Gly Ser Thr Ser
145                 150                 155                 160

Asn Ile Gly Asn Asn Tyr Val Ser Trp Tyr Gln Gln His Pro Gly Lys
                165                 170                 175

Ala Pro Lys Leu Met Ile Tyr Asp Val Ser Lys Arg Pro Ser Gly Val
            180                 185                 190

Pro Asp Arg Phe Ser Gly Ser Lys Ser Gly Asn Ser Ala Ser Leu Asp
        195                 200                 205

Ile Ser Gly Leu Gln Ser Glu Asp Glu Ala Asp Tyr Tyr Cys Ala Ala
    210                 215                 220

Trp Asp Asp Ser Leu Ser Glu Phe Leu Phe Gly Thr Gly Thr Lys Leu
225                 230                 235                 240

Thr Val Leu Gly

<210> SEQ ID NO 27
<211> LENGTH: 247
<212> TYPE: PRT
<213> ORGANISM: Artificial sequence
<220> FEATURE:
<223> OTHER INFORMATION: N015D08 scFv

<400> SEQUENCE: 27

Gln Val Gln Leu Leu Gln Ser Ala Pro Glu Val Lys Lys Pro Gly Ser
```

```
              1               5                  10                 15
Ser Val Arg Val Ser Cys Lys Thr Ser Gly Gly Thr Phe Ser Ser Gln
                      20                 25                 30

Leu Ile Asn Trp Val Arg Gln Pro Pro Gly Gln Gly Pro Glu Trp Met
                      35                 40                 45

Gly Gly Ile Ile Pro Ile Phe Gly Thr Ala Asn Tyr Ala Gln Lys Phe
             50                 55                 60

Gln Gly Arg Val Thr Ile Thr Ala Asp Glu Ser Thr Ser Thr Ala Tyr
 65                    70                 75                 80

Met Glu Leu Ser Ser Leu Arg Ser Glu Asp Thr Ala Val Tyr Tyr Cys
                      85                 90                 95

Ala Arg Asp Leu Thr Ala Gly Arg Phe Asp Ala Phe His Ile Trp Gly
                     100                105                110

Arg Gly Thr Leu Val Thr Val Ser Ser Gly Gly Gly Ser Gly Gly
                     115                120                125

Gly Gly Ser Gly Gly Gly Ser Gln Ser Val Leu Thr Gln Pro Pro
             130                135                140

Ser Val Ser Ala Ala Pro Gly Gln Lys Val Thr Ile Ser Cys Ser Gly
145                   150                155                160

Ser Thr Ser Asn Ile Gly Asn Asn Tyr Val Ser Trp Tyr Gln Gln His
                     165                170                175

Pro Gly Lys Ala Pro Lys Leu Met Ile Tyr Asp Val Ser Lys Arg Pro
                     180                185                190

Ser Gly Val Pro Asp Arg Phe Ser Gly Ser Lys Ser Gly Asn Ser Ala
                     195                200                205

Ser Leu Asp Ile Ser Gly Leu Gln Ser Glu Asp Glu Ala Asp Tyr Tyr
             210                215                220

Cys Ala Ala Trp Asp Asp Ser Leu Ser Glu Phe Leu Phe Gly Thr Gly
225                   230                235                240

Thr Lys Leu Thr Val Leu Gly
                     245

<210> SEQ ID NO 28
<211> LENGTH: 248
<212> TYPE: PRT
<213> ORGANISM: Artificial sequence
<220> FEATURE:
<223> OTHER INFORMATION: N024B07 scFv

<400> SEQUENCE: 28

Gln Val Gln Leu Gln Gln Ser Gly Ala Glu Val Lys Lys Pro Gly Ser
 1               5                  10                 15

Ser Val Lys Val Ser Cys Lys Ala Ser Gly Gly Thr Phe Ser Ser Tyr
                      20                 25                 30

Ala Ile Ser Trp Val Arg Gln Ala Pro Gly Gln Gly Leu Glu Trp Met
                      35                 40                 45

Gly Gly Ser Ile Pro Lys Phe Arg Thr Ala Asn Tyr Ala Lys Lys Phe
             50                 55                 60

Gln Gly Arg Val Thr Ile Thr Ala Asp Glu Ser Thr Ser Thr Ala Tyr
 65                    70                 75                 80

Met Glu Leu Ser Ser Leu Arg Ser Asp Asp Thr Ala Val Tyr Tyr Cys
                      85                 90                 95

Ala Arg Gly Ser Thr Tyr Asn Leu Arg Asn Ala Phe Asp Ile Trp Gly
                     100                105                110

Lys Gly Thr Leu Val Thr Val Ser Ser Gly Gly Gly Gly Ser Gly Gly
```

```
            115                 120                 125
Gly Gly Ser Gly Gly Gly Ser Ala Gln Ser Val Val Thr Gln Pro
            130                 135                 140
Pro Ser Ala Ser Gly Thr Pro Gly Gln Arg Val Thr Ile Ser Cys Ser
145                 150                 155                 160
Gly Gly Ser Ser Asn Ile Gly Arg Asn Thr Val Asn Trp Tyr Gln Gln
                165                 170                 175
Val Pro Gly Thr Ala Pro Lys Leu Leu Ile Tyr Thr Asn Asn Gln Arg
            180                 185                 190
Pro Ser Gly Val Pro Asp Arg Phe Ser Gly Ser Lys Ser Gly Thr Ser
            195                 200                 205
Ala Ser Leu Ala Ile Ser Gly Leu Gln Ser Glu Asp Glu Ala Asp Tyr
            210                 215                 220
Tyr Cys Ala Ala Trp Asp Asp Ser Leu Asn Asp Val Glu Phe Gly Gly
225                 230                 235                 240
Gly Thr Lys Leu Thr Val Leu Gly
                245

<210> SEQ ID NO 29
<211> LENGTH: 243
<212> TYPE: PRT
<213> ORGANISM: Artificial sequence
<220> FEATURE:
<223> OTHER INFORMATION: N024E07 scFv

<400> SEQUENCE: 29

Gln Val Gln Leu Gln Glu Ser Gly Gly Gly Leu Glu Gln Pro Gly Arg
  1               5                  10                  15
Ser Leu Arg Leu Ser Cys Thr Ala Ser Gly Phe Thr Phe Asp Asp Tyr
             20                  25                  30
Pro Met His Trp Val Arg Gln Ala Pro Gly Lys Gly Leu Glu Trp Val
         35                  40                  45
Ser Gly Ile Ser Gly Asn Ser Asp Arg Ile Ala Tyr Ala Asp Ser Val
     50                  55                  60
Lys Gly Arg Phe Thr Ile Ser Arg Asp Asn Ser Lys Asn Thr Leu Trp
 65                  70                  75                  80
Leu Gln Met Asn Ser Leu Arg Ala Glu Asp Thr Ala Ile Tyr Tyr Cys
                 85                  90                  95
Ala Arg Ala Ala Arg Asn Trp Phe Asp Pro Trp Gly Gln Gly Thr Leu
            100                 105                 110
Val Thr Val Ser Ser Gly Gly Gly Ser Gly Gly Gly Gly Ser Gly
        115                 120                 125
Gly Gly Gly Ser Gln Ser Val Leu Thr Gln Pro Pro Ser Val Ser Ala
        130                 135                 140
Ala Pro Gly Gln Lys Val Thr Ile Ser Cys Ser Gly Ser Thr Ser Asn
145                 150                 155                 160
Ile Gly Asn Asn Tyr Val Ser Trp Tyr Gln Gln His Pro Gly Lys Ala
                165                 170                 175
Pro Lys Leu Met Ile Tyr Asp Val Ser Lys Arg Pro Ser Gly Val Pro
            180                 185                 190
Asp Arg Phe Ser Gly Ser Lys Ser Gly Asn Ser Ala Ser Leu Asp Ile
            195                 200                 205
Ser Gly Leu Gln Ser Glu Asp Glu Ala Asp Tyr Tyr Cys Ala Ala Trp
            210                 215                 220
Asp Asp Ser Leu Ser Glu Phe Leu Phe Gly Thr Gly Thr Lys Leu Thr
```

225               230               235               240

Val Leu Gly

<210> SEQ ID NO 30
<211> LENGTH: 255
<212> TYPE: PRT
<213> ORGANISM: Artificial sequence
<220> FEATURE:
<223> OTHER INFORMATION: N023F05 scFv

<400> SEQUENCE: 30

Gln Val Gln Leu Val Gln Ser Gly Ala Glu Val Lys Lys Pro Gly Phe
1               5                   10                  15

Ser Val Lys Val Ser Cys Lys Ala Ser Gly Gly Ser Phe Ser Asn Tyr
            20                  25                  30

Val Ile Ser Trp Leu Arg Gln Ala Pro Gly Gln Gly Leu Glu Trp Met
        35                  40                  45

Gly Gly Ile Met Pro Ile Phe Gly Asn Ala Asn Tyr Ala Gln Lys Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Asp Thr Ala Val Tyr Tyr Cys
                85                  90                  95

Ala Arg Asp Gln Ile Val Val Asp Pro Val Thr Lys Gly Ala Tyr Tyr
            100                 105                 110

Ser Gly Leu Asp Val Trp Gly Arg Gly Thr Met Val Thr Val Ser Ser
        115                 120                 125

Gly Gly Gly Gly Ser Gly Gly Gly Ser Gly Gly Gly Gly Ser Ala
    130                 135                 140

Gln Ser Val Leu Thr Gln Pro Pro Ser Ala Ser Gly Thr Pro Gly Gln
145                 150                 155                 160

Arg Val Thr Ile Ser Cys Ser Gly Ser Ser Asn Ile Gly Ala Asn
            165                 170                 175

Ala Ile Thr Trp Phe Gln Gln Leu Pro Gly Thr Ala Pro Lys Leu Leu
        180                 185                 190

Ile Tyr His Asn Asn Gln Arg Pro Ser Gly Val Pro Asp Arg Phe Ser
    195                 200                 205

Gly Ser Lys Ser Gly Thr Ser Gly Ser Leu Ala Ile Ser Gly Leu Gln
    210                 215                 220

Ser Glu Asp Glu Ala Asp Tyr Tyr Cys Ala Val Trp Asp Asn Ser Leu
225                 230                 235                 240

Asn Ala Met Leu Phe Gly Gly Gly Thr Lys Leu Thr Val Leu Gly
            245                 250                 255

<210> SEQ ID NO 31
<211> LENGTH: 245
<212> TYPE: PRT
<213> ORGANISM: Artificial sequence
<220> FEATURE:
<223> OTHER INFORMATION: N024D08 scFv

<400> SEQUENCE: 31

Glu Val Gln Leu Val Gln Ser Gly Ala Glu Val Lys Arg Pro Gly Ala
1               5                   10                  15

Ser Val Lys Ile Ser Cys Arg Thr Ser Gly Tyr Thr Phe Thr Ser Tyr
            20                  25                  30

Tyr Ile His Trp Val Arg Gln Ala Pro Gly Gln Gly Leu Glu Trp Leu

```
                    35                  40                  45
Ala Ile Ile Asn Pro Thr Ala Gly Asn Thr Tyr Tyr Thr Gln Asp Phe
 50                      55                  60

Gln Asp Arg Val Thr Val Thr Arg Asp Thr Ser Thr Ser Thr Val Tyr
 65                  70                  75                  80

Met Glu Leu Arg Gly Leu Asn Ser Glu Asp Thr Ala Val Tyr Tyr Cys
                 85                  90                  95

Ala Ser Pro Tyr Gly Val Arg Asn Ala Phe Asp Val Trp Gly Gln Gly
            100                 105                 110

Thr Met Val Thr Val Ser Ser Gly Gly Gly Ser Gly Gly Gly
        115                 120                 125

Ser Gly Gly Gly Ser Gln Ser Val Leu Thr Gln Pro Pro Ser Val
130                 135                 140

Ser Ala Ala Pro Gly Gln Lys Val Thr Ile Ser Cys Ser Gly Ser Thr
145                 150                 155                 160

Ser Asn Ile Gly Asn Asn Tyr Val Ser Trp Tyr Gln Gln His Pro Gly
                165                 170                 175

Lys Ala Pro Lys Leu Met Ile Tyr Asp Val Ser Lys Arg Pro Ser Gly
            180                 185                 190

Val Pro Asp Arg Phe Ser Gly Ser Lys Ser Gly Asn Ser Ala Ser Leu
        195                 200                 205

Asp Ile Ser Gly Leu Gln Ser Glu Asp Glu Ala Asp Tyr Tyr Cys Ala
    210                 215                 220

Ala Trp Asp Asp Ser Leu Ser Glu Phe Leu Phe Gly Thr Gly Thr Lys
225                 230                 235                 240

Leu Thr Val Leu Gly
                245

<210> SEQ ID NO 32
<211> LENGTH: 248
<212> TYPE: PRT
<213> ORGANISM: Artificial sequence
<220> FEATURE:
<223> OTHER INFORMATION: N023B03 scFv

<400> SEQUENCE: 32

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gln Gly Ser Gly Ser Tyr Pro Pro Ala Phe Asp Ser Trp
            100                 105                 110

Gly Arg Gly Thr Met Val Thr Val Ser Ser Gly Gly Gly Ser Gly
        115                 120                 125

Gly Gly Ser Gly Gly Gly Gly Ser Ala Gln Ala Val Val Ile Gln
130                 135                 140

Glu Pro Ser Leu Thr Val Ser Pro Gly Gly Thr Val Thr Leu Thr Cys
```

```
                145                 150                 155                 160
Ala Phe Asn Ser Gly Gln Val Thr Ser Gly Phe Tyr Pro Asn Trp Phe
                165                 170                 175

Gln Gln Lys Pro Gly Gln Pro Pro Arg Ser Leu Ile Tyr Asn Thr Asp
            180                 185                 190

Asn Lys His Ser Trp Thr Pro Ala Arg Phe Ser Gly Ser Leu Leu Gly
            195                 200                 205

Gly Lys Ala Ala Leu Thr Leu Ser Gly Val Gln Pro Asp Asp Glu Ala
            210                 215                 220

Asp Tyr Tyr Cys Leu Leu Tyr Tyr Asp Arg Ser Leu Val Phe Gly Gly
225                 230                 235                 240

Gly Thr Lys Leu Thr Val Leu Gly
                245

<210> SEQ ID NO 33
<211> LENGTH: 243
<212> TYPE: PRT
<213> ORGANISM: Artificial sequence
<220> FEATURE:
<223> OTHER INFORMATION: N023E01 scFv

<400> SEQUENCE: 33

Gln Val Gln Leu Val Gln Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
                 20                  25                  30

Ala Met His Trp Val Arg Gln Ala Pro Gly Lys Gly Leu Glu Trp Val
             35                  40                  45

Ser Gly Ile Ser Trp Asn Ser Ala Ser Ile Gly Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Gly Glu Asp Thr Ala Leu Tyr Tyr Cys
                 85                  90                  95

Ala Lys Gly Ala Arg Asp Ala Leu Asp Ile Trp Gly Lys Gly Thr Leu
            100                 105                 110

Leu Thr Val Ser Ser Gly Gly Gly Gly Ser Gly Gly Gly Gly Ser Gly
            115                 120                 125

Gly Gly Gly Ser Gln Ser Val Leu Thr Gln Pro Ser Val Ser Ala
            130                 135                 140

Ala Pro Gly Gln Lys Val Thr Ile Ser Cys Ser Gly Ser Thr Ser Asn
145                 150                 155                 160

Ile Gly Asn Asn Tyr Val Ser Trp Tyr Gln Gln His Pro Gly Lys Ala
                165                 170                 175

Pro Lys Leu Met Ile Tyr Asp Val Ser Lys Arg Pro Ser Gly Val Pro
            180                 185                 190

Asp Arg Phe Ser Gly Ser Lys Ser Gly Asn Ser Ala Ser Leu Asp Ile
            195                 200                 205

Ser Gly Leu Gln Ser Glu Asp Glu Ala Asp Tyr Tyr Cys Ala Ala Trp
            210                 215                 220

Asp Asp Ser Leu Ser Glu Phe Leu Phe Gly Thr Gly Thr Lys Leu Thr
225                 230                 235                 240

Val Leu Gly

<210> SEQ ID NO 34
```

<211> LENGTH: 251
<212> TYPE: PRT
<213> ORGANISM: Artificial sequence
<220> FEATURE:
<223> OTHER INFORMATION: N024C05 scFv

<400> SEQUENCE: 34

```
Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Thr Ala Ala Trp Ser Trp Ile Arg Gln Ser Pro Ser Arg Gly Leu Glu
        35                  40                  45

Trp Leu Gly Arg Thr Tyr Tyr Ser Arg Ser Lys Trp Tyr Lys Asp Tyr
    50                  55                  60

Ala Val Ser Val Lys Ser Arg Ile Thr Ile Asn Pro Asp Thr Ser Lys
65                  70                  75                  80

Asn Gln Phe Ser Leu Gln Leu Asp Ser Val Thr Pro Glu Asp Thr Ala
                85                  90                  95

Val Tyr Tyr Cys Thr Arg Glu Gly Tyr Tyr Asp Tyr Ser Gly Val Val
            100                 105                 110

Asp Tyr Trp Gly Gln Gly Thr Thr Val Ile Val Ser Ser Gly Gly Gly
        115                 120                 125

Gly Ser Gly Gly Gly Gly Ser Gly Gly Gly Gly Ser Gln Ser Val Leu
    130                 135                 140

Thr Gln Pro Pro Ser Ala Ser Gly Ser Pro Gly Gln Ser Val Thr Ile
145                 150                 155                 160

Ser Cys Thr Gly Thr Ser Ser Asp Val Gly Gly Tyr Asn Tyr Val Ser
                165                 170                 175

Trp Tyr Gln Gln His Pro Gly Lys Ala Pro Lys Phe Met Ile Tyr Asp
            180                 185                 190

Val Ser Lys Arg Pro Ser Gly Val Ser Asn Arg Phe Ser Gly Ser Lys
        195                 200                 205

Ser Gly Asn Thr Ala Ser Leu Thr Ile Ser Gly Val Gln Ala Glu Asp
    210                 215                 220

Glu Ala Asp Tyr Tyr Cys Ser Ser Tyr Thr Ser Ala Ser Thr Val Ile
225                 230                 235                 240

Phe Gly Gly Gly Thr Lys Leu Thr Val Leu Gly
                245                 250
```

<210> SEQ ID NO 35
<211> LENGTH: 245
<212> TYPE: PRT
<213> ORGANISM: Artificial sequence
<220> FEATURE:
<223> OTHER INFORMATION: N025E05 scFv

<400> SEQUENCE: 35

```
Gln Val Gln Leu Gln Gln Ser Gly Ala Glu Val Lys Lys Pro Gly Ser
 1               5                  10                  15

Ser Val Lys Val Ser Cys Lys Ala Ser Gly Asp Thr Phe Ser Ser Asn
            20                  25                  30

Thr Ile Ser Trp Val Arg Gln Ala Pro Gly Gln Gly Leu Glu Trp Met
        35                  40                  45

Gly Gly Ile Ile Pro Ile Ile Gly Thr Pro His Tyr Ala Gln Lys Phe
    50                  55                  60

Gln Gly Arg Val Thr Ile Thr Ala Asp Arg Ser Thr Ser Thr Ala Tyr
```

-continued

```
                 65                  70                  75                  80
Met Glu Leu Thr Asn Leu Arg Ser Glu Asp Thr Ala Val Tyr Phe Cys
                         85                  90                  95

Ala Arg Asn Arg Val Gly Thr Ser Ser Phe Asp Phe Trp Gly Gln Gly
                100                 105                 110

Thr Met Val Thr Val Ser Ser Gly Gly Gly Ser Gly Gly Gly Gly
            115                 120                 125

Ser Gly Gly Gly Ser Ala Leu Pro Val Leu Thr Gln Pro Pro Ser
    130                 135                 140

Ala Ser Gly Thr Pro Gly Gln Arg Val Thr Ile Ser Cys Ser Gly Ser
145                 150                 155                 160

Ser Ser Asn Ile Gly Ser Asn Thr Val Asn Trp Tyr Gln Gln Leu Pro
                165                 170                 175

Gly Thr Ala Pro Lys Leu Phe Ile Tyr Ser Asn Asn Gln Arg Pro Ser
                180                 185                 190

Gly Val Pro Asp Arg Phe Ser Gly Ser Lys Ser Gly Thr Ser Ala Ser
                195                 200                 205

Leu Ala Ile Ser Gly Leu Gln Ser Glu Asp Glu Ala Asp Tyr Tyr Cys
            210                 215                 220

Ser Ser Trp Asp Asp Ser Leu Asn Leu Ile Phe Gly Gly Gly Thr Lys
225                 230                 235                 240

Val Thr Val Leu Gly
                245
```

<210> SEQ ID NO 36
<211> LENGTH: 245
<212> TYPE: PRT
<213> ORGANISM: Artificial sequence
<220> FEATURE:
<223> OTHER INFORMATION: N025C01 scFv

<400> SEQUENCE: 36

```
Gln Val Gln Leu Val Gln Ser Gly Ala Glu Val Lys Lys Pro Gly Thr
 1               5                  10                  15

Ser Val Lys Val Ser Cys Lys Ala Ala Gly Asp Thr Phe Arg Ser Tyr
                20                  25                  30

Ile Ile Ser Trp Val Arg Gln Ala Pro Gly Gln Gly Leu Glu Trp Val
            35                  40                  45

Gly Gly Ile Ile Pro Met Phe Gly Thr Ser Asn Tyr Ala Gln Lys Phe
    50                  55                  60

Gln Gly Arg Val Thr Ile Thr Ala Asp Asp Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Ala Gln Gly Gly Ser Tyr Tyr Asn Tyr Trp Gly Gln Gly
                100                 105                 110

Thr Pro Val Thr Val Ser Ser Gly Gly Gly Gly Ser Gly Gly Gly Gly
            115                 120                 125

Ser Gly Gly Gly Gly Ser Gln Ser Val Leu Thr Gln Pro Pro Ser Val
    130                 135                 140

Ser Ala Ala Pro Gly Gln Lys Val Thr Ile Ser Cys Ser Gly Ser Thr
145                 150                 155                 160

Ser Asn Ile Gly Asn Asn Tyr Val Ser Trp Tyr Gln Gln His Pro Gly
                165                 170                 175

Lys Ala Pro Lys Leu Met Ile Tyr Asp Val Ser Lys Arg Pro Ser Gly
```

-continued

```
                180             185              190
Val Pro Asp Arg Phe Ser Gly Ser Lys Ser Gly Asn Ser Ala Ser Leu
            195             200             205

Asp Ile Ser Gly Leu Gln Ser Glu Asp Glu Ala Asp Tyr Tyr Cys Ala
        210             215             220

Ala Trp Asp Asp Gly Leu Ser Glu Phe Leu Phe Gly Thr Gly Thr Lys
225             230             235             240

Leu Thr Val Leu Gly
            245

<210> SEQ ID NO 37
<211> LENGTH: 247
<212> TYPE: PRT
<213> ORGANISM: Artificial sequence
<220> FEATURE:
<223> OTHER INFORMATION: N024F09 scFv

<400> SEQUENCE: 37

Gln Val Gln Leu Gln Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Arg Leu Glu Trp Met
        35                  40                  45

Gly Gly Ile Leu Pro Phe Phe Gly Thr Thr Ser Tyr Ala Gln Asn Phe
    50                  55                  60

His Gly Arg Leu Thr Ile Thr Ala Asp Glu Ser Thr Arg Thr Ala Tyr
65                  70                  75                  80

Met Glu Leu Ser Ser Leu Lys Ser Glu Asp Thr Ala Val Tyr Tyr Cys
                85                  90                  95

Ala Arg Asp Glu Ser Ala Asp Pro Lys Asn Ala Phe Asp Ile Trp Gly
            100                 105                 110

Arg Gly Thr Met Val Thr Val Ser Ser Gly Gly Gly Ser Gly Gly
        115                 120                 125

Gly Gly Ser Gly Gly Gly Ser Gln Ser Val Leu Thr Gln Pro Pro
    130                 135                 140

Pro Val Ser Ala Ala Pro Gly Gln Lys Val Thr Ile Ser Cys Ser Gly
145                 150                 155                 160

Ser Thr Ser Asn Ile Gly Asn Asn Tyr Val Ser Trp Tyr Gln Gln Arg
                165                 170                 175

Pro Gly Lys Ala Pro Lys Leu Met Ile Tyr Asp Val Ser Lys Arg Pro
            180                 185                 190

Ser Gly Val Pro Asp Arg Phe Ser Gly Ser Lys Ser Gly Asn Ser Ala
        195                 200                 205

Ser Leu Asp Ile Ser Gly Leu Gln Ser Glu Asp Glu Ala Asp Tyr Tyr
    210                 215                 220

Cys Ala Ala Trp Asp Asp Ser Leu Ser Glu Phe Leu Phe Gly Thr Gly
225                 230                 235                 240

Thr Lys Leu Thr Val Leu Gly
                245

<210> SEQ ID NO 38
<211> LENGTH: 246
<212> TYPE: PRT
<213> ORGANISM: Artificial sequence
<220> FEATURE:
<223> OTHER INFORMATION: N024B01 scFv
```

<400> SEQUENCE: 38

```
Gln Val Gln Leu Gln Gln Ser Gly Asn Glu Val Lys Lys Pro Gly Ser
  1               5                  10                  15

Ser Val Lys Ile Ser Cys Lys Ala Ser Gly Ala Pro Phe Asn Ser Tyr
             20                  25                  30

Val Ile Ser Trp Val Arg Gln Ala Pro Gly Gln Gly Leu Glu Trp Val
         35                  40                  45

Gly Gly Val Val Pro Ile Phe Gly Thr Ala His Tyr Ala His Gln Phe
     50                  55                  60

Gln Gly Arg Val Thr Ile Ile Ala Asp Lys Ser Thr Ser Thr Val Tyr
 65                  70                  75                  80

Met Glu Leu Arg Gly Leu Thr Ser Asp Thr Ala Glu Tyr Phe Cys
                 85                  90                  95

Ala Arg Gln Gly Pro Tyr Gly Lys Leu Asp Asp Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Ala Leu Ser Tyr Glu Leu Thr Gln Pro Pro Ser
    130                 135                 140

Ala Ser Gly Thr Pro Gly Gln Arg Val Thr Ile Ser Cys Ser Gly Ser
145                 150                 155                 160

Ser Ser Asn Ile Gly Ser Asn Tyr Val Tyr Trp Tyr Gln Gln Phe Pro
                165                 170                 175

Gly Thr Ala Pro Lys Leu Leu Met Tyr Arg Asn Asn Gln Arg Pro Ser
            180                 185                 190

Gly Val Pro Asp Arg Phe Ser Gly Ser Lys Phe Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Ser Leu Thr Gly Arg Val Phe Gly Gly Gly Thr
225                 230                 235                 240

Lys Val Thr Val Leu Gly
                245
```

<210> SEQ ID NO 39
<211> LENGTH: 248
<212> TYPE: PRT
<213> ORGANISM: Artificial sequence
<220> FEATURE:
<223> OTHER INFORMATION: N024F07 scFv

<400> SEQUENCE: 39

```
Gln Val Gln Leu Gln Gln Ser Gly Ala Glu Val Lys Lys Pro Gly Ser
  1               5                  10                  15

Ser Val Asn Val Ser Cys Lys Ala Ser Gly Gly Thr Phe Asp Thr Phe
             20                  25                  30

Gly Ile Ser Trp Val Arg Gln Ala Pro Gly Lys Gly Leu Glu Trp Met
         35                  40                  45

Gly Val Ile Ala His Asp Gly Ser Ile Ser Tyr Tyr Ala Asp Ser Val
     50                  55                  60

Lys Gly Arg Phe Thr Phe Ser Arg Asp Asn Ser Lys Asn Thr Val Ser
 65                  70                  75                  80

Leu Gln Met Asn Ser Pro Arg Pro Glu Asp Thr Ala Val Tyr Tyr Cys
                 85                  90                  95
```

```
Ala Lys Gly Glu Tyr Asp Ser Ser Gly Tyr Asn Ala Phe Asp Ile Trp
            100                 105                 110
Gly Lys Gly Thr Leu Val Thr Val Ser Ser Gly Gly Gly Ser Gly
        115                 120                 125
Gly Gly Gly Ser Gly Gly Gly Ser Gln Ser Val Leu Thr Gln Pro
130                 135                 140
Pro Ser Val Ser Ala Ala Pro Gly Gln Lys Val Thr Val Ser Cys Ser
145                 150                 155                 160
Gly Ser Thr Ser Asn Ile Gly Asn Asn Tyr Val Ser Trp Tyr Gln Gln
                165                 170                 175
His Pro Gly Lys Ala Pro Lys Leu Met Ile Tyr Asp Val Ser Lys Arg
            180                 185                 190
Pro Ser Gly Val Pro Asp Arg Phe Ser Gly Ser Lys Ser Gly Asn Ser
        195                 200                 205
Ala Ser Leu Asp Ile Ser Gly Leu Gln Ser Glu Asp Glu Ala Asp Tyr
    210                 215                 220
Tyr Cys Ala Ala Trp Asp Asp Ser Leu Ser Glu Phe Leu Phe Gly Thr
225                 230                 235                 240
Gly Thr Lys Leu Thr Val Leu Gly
                245

<210> SEQ ID NO 40
<211> LENGTH: 242
<212> TYPE: PRT
<213> ORGANISM: Artificial sequence
<220> FEATURE:
<223> OTHER INFORMATION: N015D10 scFv

<400> SEQUENCE: 40

Gln Val Gln Leu Val Gln Ser Gly Ala Glu Val Lys Lys Pro Gly Ser
  1               5                  10                  15
Ser Val Arg Ile Ser Cys Lys Ala Ser Gly Gly Ser Phe Arg Thr Tyr
            20                  25                  30
Val Val Ser Trp Val Arg Gln Ala Pro Gly Gln Gly Leu Glu Trp Met
        35                  40                  45
Gly Gly Ile Ile Pro Val Tyr Gly Thr Pro Asn Tyr Ala Gln Lys Phe
    50                  55                  60
Gln Gly Arg Val Thr Ile Thr Ala Asp Glu Pro Thr Arg Thr Thr Tyr
65                  70                  75                  80
Met Glu Leu Ser Ser Leu Arg Ser Glu Asp Thr Gly Val Tyr Tyr Cys
                85                  90                  95
Ala Arg Asn Gly Gly Gly Leu Asp Tyr Trp Gly Gln Gly Thr Met Val
            100                 105                 110
Thr Val Ser Ser Gly Gly Gly Gly Ser Gly Gly Gly Gly Ser Gly Gly
        115                 120                 125
Gly Gly Ser Gln Ser Val Leu Thr Gln Pro Pro Ser Val Ser Ala Ala
    130                 135                 140
Pro Gly Gln Lys Val Thr Ile Ser Cys Ser Gly Ser Thr Ser Asn Ile
145                 150                 155                 160
Gly Asn Asn Tyr Val Ser Trp Tyr Gln Gln His Pro Gly Lys Ala Pro
                165                 170                 175
Lys Leu Met Ile Tyr Asp Val Ser Lys Arg Pro Ser Gly Val Pro Asp
            180                 185                 190
Arg Phe Ser Gly Ser Lys Ser Gly Asn Ser Ala Ser Leu Asp Ile Ser
        195                 200                 205
```

```
Gly Leu Gln Ser Glu Asp Glu Ala Asp Tyr Tyr Cys Ala Ala Trp Asp
    210             215                 220

Asp Ser Leu Ser Glu Phe Leu Phe Gly Thr Gly Thr Lys Leu Thr Val
225             230                 235                 240

Leu Gly

<210> SEQ ID NO 41
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 41
caggtgcagc tggtgcagtc tgg                                              23

<210> SEQ ID NO 42
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 42
caggtcaact taagggagtc tgg                                              23

<210> SEQ ID NO 43
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 43
gaggtgcagc tggtggagtc tgg                                              23

<210> SEQ ID NO 44
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 44
caggtgcagc tgcaggagtc ggg                                              23

<210> SEQ ID NO 45
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 45
gaggtgcagc tgttgcagtc tgc                                              23

<210> SEQ ID NO 46
<211> LENGTH: 23
<212> TYPE: DNA
<213> ORGANISM: Artificial sequence
<220> FEATURE:
```

<223> OTHER INFORMATION: PCR primer useful for amplifying VH and VL
      domains

<400> SEQUENCE: 46
caggtacagc tgcagcagtc agg                                          23

<210> SEQ ID NO 47
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 47
tgaggagacg gtgaccaggg tgcc                                         24

<210> SEQ ID NO 48
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 48
tgaagagacg gtgaccattg tccc                                         24

<210> SEQ ID NO 49
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 49
tgaggagacg gtgaccaggg ttcc                                         24

<210> SEQ ID NO 50
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 50
tgaggagacg gtgaccgtgg tccc                                         24

<210> SEQ ID NO 51
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 51
gacatccaga tgacccagtc tcc                                          23

<210> SEQ ID NO 52
<211> LENGTH: 23
<212> TYPE: DNA
<213> ORGANISM: Artificial sequence
<220> FEATURE:
<223> OTHER INFORMATION: PCR primer useful for amplifying VH and VL

```
                              domains

<400> SEQUENCE: 52
gatgttgtga tgactcagtc tcc                                              23

<210> SEQ ID NO 53
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 53
gatattgtga tgactcagtc tcc                                              23

<210> SEQ ID NO 54
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 54
gaaattgtgt tgacgcagtc tcc                                              23

<210> SEQ ID NO 55
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 55
gacatcgtga tgacccagtc tcc                                              23

<210> SEQ ID NO 56
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 56
gaaacgacac tcacgcagtc tcc                                              23

<210> SEQ ID NO 57
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 57
gaaattgtgc tgactcagtc tcc                                              23

<210> SEQ ID NO 58
<211> LENGTH: 23
<212> TYPE: DNA
<213> ORGANISM: Artificial sequence
<220> FEATURE:
<223> OTHER INFORMATION: PCR primer useful for amplifying VH and VL
      domains
```

```
<400> SEQUENCE: 58
cagtctgtgt tgacgcagcc gcc                                              23

<210> SEQ ID NO 59
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 59
cagtctgccc tgactcagcc tgc                                              23

<210> SEQ ID NO 60
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 60
tcctatgtgc tgactcagcc acc                                              23

<210> SEQ ID NO 61
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 61
tcttctgagc tgactcagga ccc                                              23

<210> SEQ ID NO 62
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 62
cacgttatac tgactcaacc gcc                                              23

<210> SEQ ID NO 63
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 63
caggctgtgc tcactcagcc gtc                                              23

<210> SEQ ID NO 64
<211> LENGTH: 23
<212> TYPE: DNA
<213> ORGANISM: Artificial sequence
<220> FEATURE:
<223> OTHER INFORMATION: PCR primer useful for amplifying VH and VL
      domains
```

-continued

```
<400> SEQUENCE: 64
aattttatgc tgactcagcc cca                                           23

<210> SEQ ID NO 65
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 65
acgtttgatt tccaccttgg tccc                                          24

<210> SEQ ID NO 66
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 66
acgtttgatc tccagcttgg tccc                                          24

<210> SEQ ID NO 67
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 67
acgtttgata tccactttgg tccc                                          24

<210> SEQ ID NO 68
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 68
acgtttgatc tccaccttgg tccc                                          24

<210> SEQ ID NO 69
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 69
acgtttaatc tccagtcgtg tccc                                          24

<210> SEQ ID NO 70
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 70
```
cagtctgtgt tgacgcagcc gcc                                              23

<210> SEQ ID NO 71
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 71
cagtctgccc tgactcagcc tgc                                              23

<210> SEQ ID NO 72
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 72
tcctatgtgc tgactcagcc acc                                              23

<210> SEQ ID NO 73
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 73
tcttctgagc tgactcagga ccc                                              23

<210> SEQ ID NO 74
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 74
cacgttatac tgactcaacc gcc                                              23

<210> SEQ ID NO 75
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 75
caggctgtgc tcactcagcc gtc                                              23

<210> SEQ ID NO 76
<211> LENGTH: 23
<212> TYPE: DNA
<213> ORGANISM: Artificial sequence
<220> FEATURE:
<223> OTHER INFORMATION: PCR primer useful for amplifying VH and VL
      domains -continued

```
<400> SEQUENCE: 76
aattttatgc tgactcagcc cca                                              23
```